(12) United States Patent
Walters

(10) Patent No.: US 10,639,019 B2
(45) Date of Patent: May 5, 2020

(54) VASCULAR CLOSURE DEVICES AND METHODS OF USE

(71) Applicant: ESSENTIAL MEDICAL, INC., Malvern, PA (US)

(72) Inventor: Greg Walters, Exton, PA (US)

(73) Assignee: Arrow International, Inc., Wayne, PA (US)

( * ) Notice: Subject to any disclaimer, the term of this patent is extended or adjusted under 35 U.S.C. 154(b) by 821 days.

(21) Appl. No.: 14/777,090

(22) PCT Filed: Mar. 10, 2014

(86) PCT No.: PCT/US2014/022416
§ 371 (c)(1),
(2) Date: Sep. 15, 2015

(87) PCT Pub. No.: WO2014/150154
PCT Pub. Date: Sep. 25, 2014

(65) Prior Publication Data
US 2016/0007977 A1 Jan. 14, 2016

Related U.S. Application Data

(60) Provisional application No. 61/794,776, filed on Mar. 15, 2013.

(51) Int. Cl.
*A61B 17/08* (2006.01)
*A61D 1/00* (2006.01)
(Continued)

(52) U.S. Cl.
CPC .......... *A61B 17/0057* (2013.01); *A61B 17/04* (2013.01); *A61B 17/0469* (2013.01);
(Continued)

(58) Field of Classification Search
CPC . A61B 17/0057; A61B 17/04; A61B 17/0469; A61B 17/0482; A61B 17/0401;
(Continued)

(56) References Cited

U.S. PATENT DOCUMENTS

| 5,282,827 A | 2/1994 | Kensey et al. |
| 5,662,681 A * | 9/1997 | Nash ................. A61B 17/0057 604/285 |

(Continued)

*Primary Examiner* — Melanie R Tyson
(74) *Attorney, Agent, or Firm* — Offit Kurman, P.C.; Gregory A. Grissett

(57) ABSTRACT

A closure device system for sealing a percutaneous puncture in a vessel wall can comprise a toggle configured to engage an interior surface of the vessel wall, a plug configured to engage an exterior surface of the vessel wall, and a suture that extends through the plug and through the toggle along at least a first direction so as to couple the toggle to the plug. The system can further comprise a tube that extends through the plug and through the toggle along the first direction such that a distal end of the tube is disposed distally to the toggle. The tube can define a guidewire lumen that extends therethrough along the first direction. And the guidewire lumen can be configured to receive a guidewire that protrudes from the vessel wall such that the plug, toggle, and tube are slidable along the guidewire toward the vessel wall.

18 Claims, 48 Drawing Sheets

(51) Int. Cl.
- *A61B 17/00* (2006.01)
- *A61B 17/04* (2006.01)
- *A61B 17/22* (2006.01)
- *A61B 17/12* (2006.01)
- *A61B 90/00* (2016.01)

(52) U.S. Cl.
CPC ............ *A61B 17/0482* (2013.01); *A61B 2017/00615* (2013.01); *A61B 2017/00619* (2013.01); *A61B 2017/00623* (2013.01); *A61B 2017/00654* (2013.01); *A61B 2017/00659* (2013.01); *A61B 2017/0474* (2013.01); *A61B 2017/0496* (2013.01); *A61B 2017/12004* (2013.01); *A61B 2017/12127* (2013.01); *A61B 2017/22038* (2013.01); *A61B 2017/22069* (2013.01); *A61B 2090/0811* (2016.02); *A61B 2090/3933* (2016.02); *A61B 2090/3966* (2016.02)

(58) Field of Classification Search
CPC ........... A61B 2017/00615; A61B 2017/00619; A61B 2017/00474; A61B 2017/12004; A61B 2017/12127; A61B 2017/22038; A61B 2017/22069; A61B 2017/0409; A61B 2017/00575; A61B 2017/00654; A61B 2017/00659; A61B 2090/0811; A61B 2090/3933; A61B 2090/3966
USPC ........................................................ 606/213
See application file for complete search history.

(56) References Cited

U.S. PATENT DOCUMENTS

| | | |
|---|---|---|
| 6,056,768 A | 5/2000 | Cates |
| 8,870,917 B2 | 10/2014 | Walters |
| 2004/0267308 A1 | 12/2004 | Bagaoisan |
| 2009/0171387 A1* | 7/2009 | Pipenhagen ....... A61B 17/0057 606/213 |
| 2011/0046665 A1 | 2/2011 | Green et al. |
| 2011/0301619 A1 | 12/2011 | Walters |

* cited by examiner

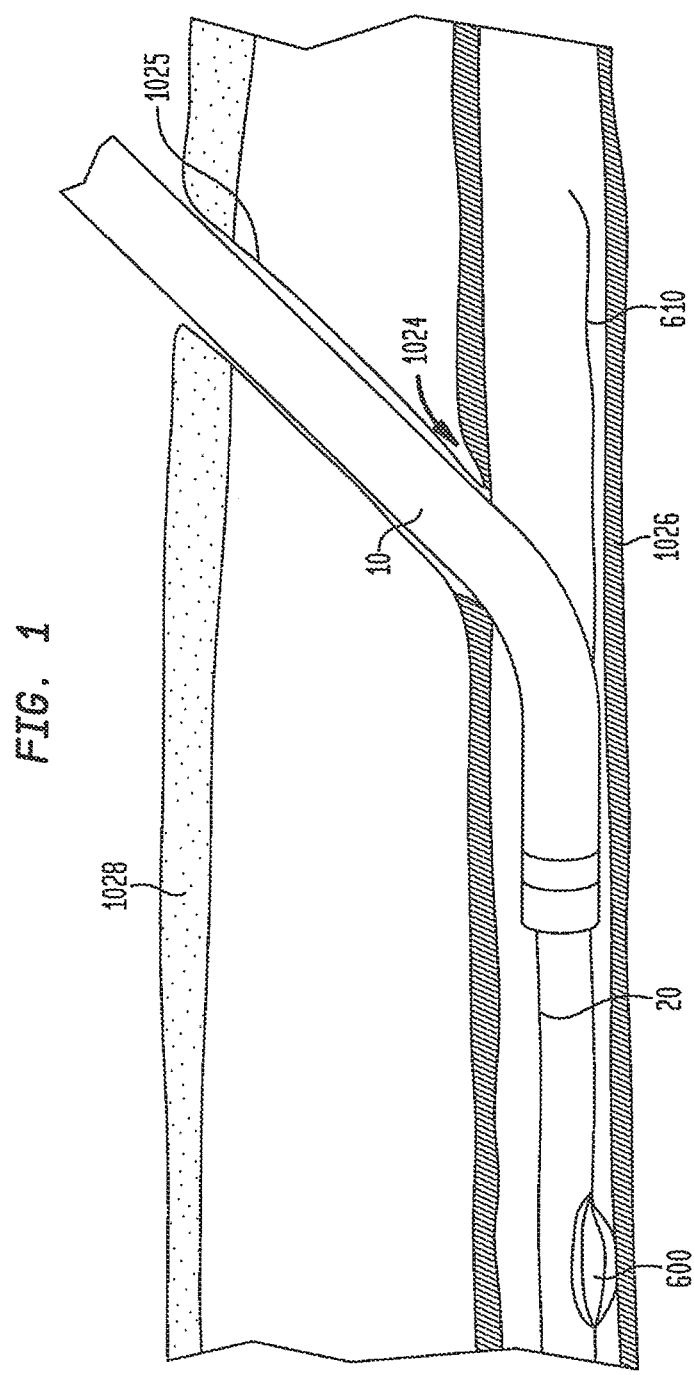

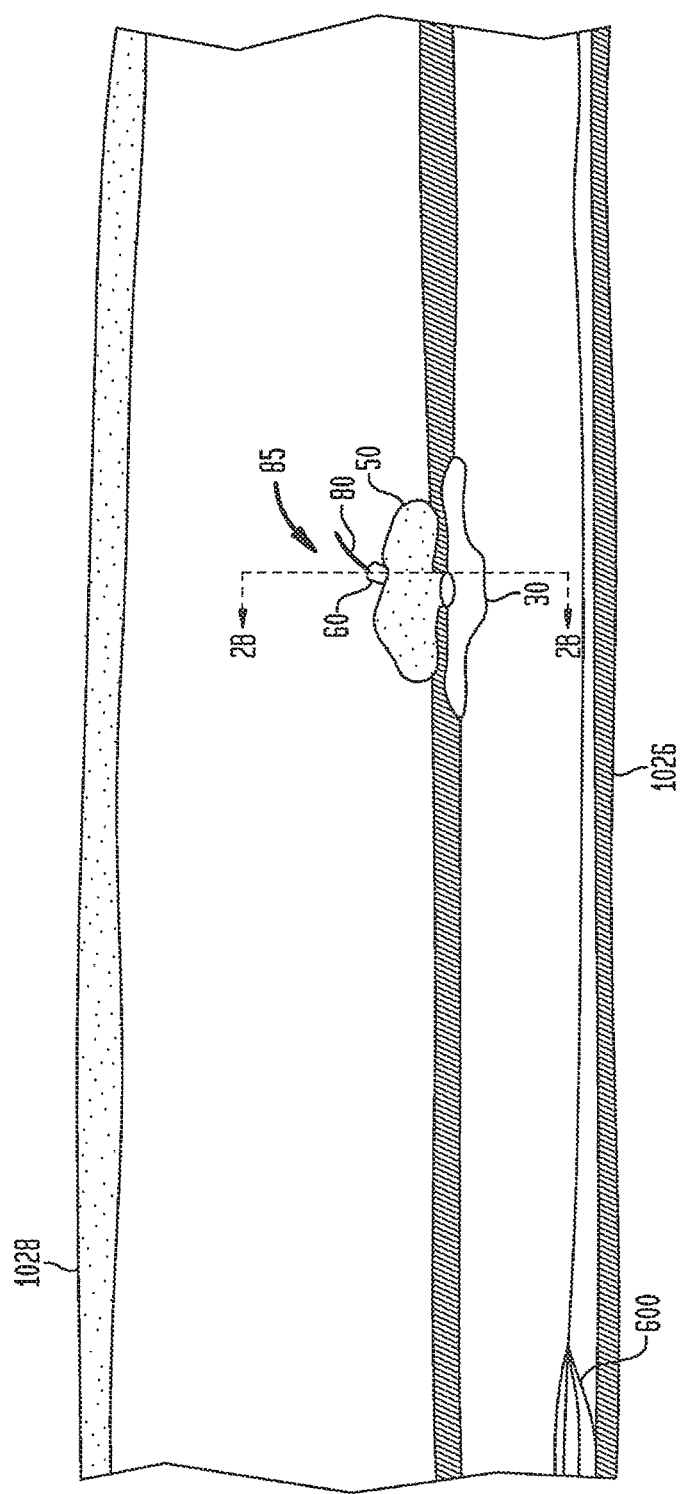

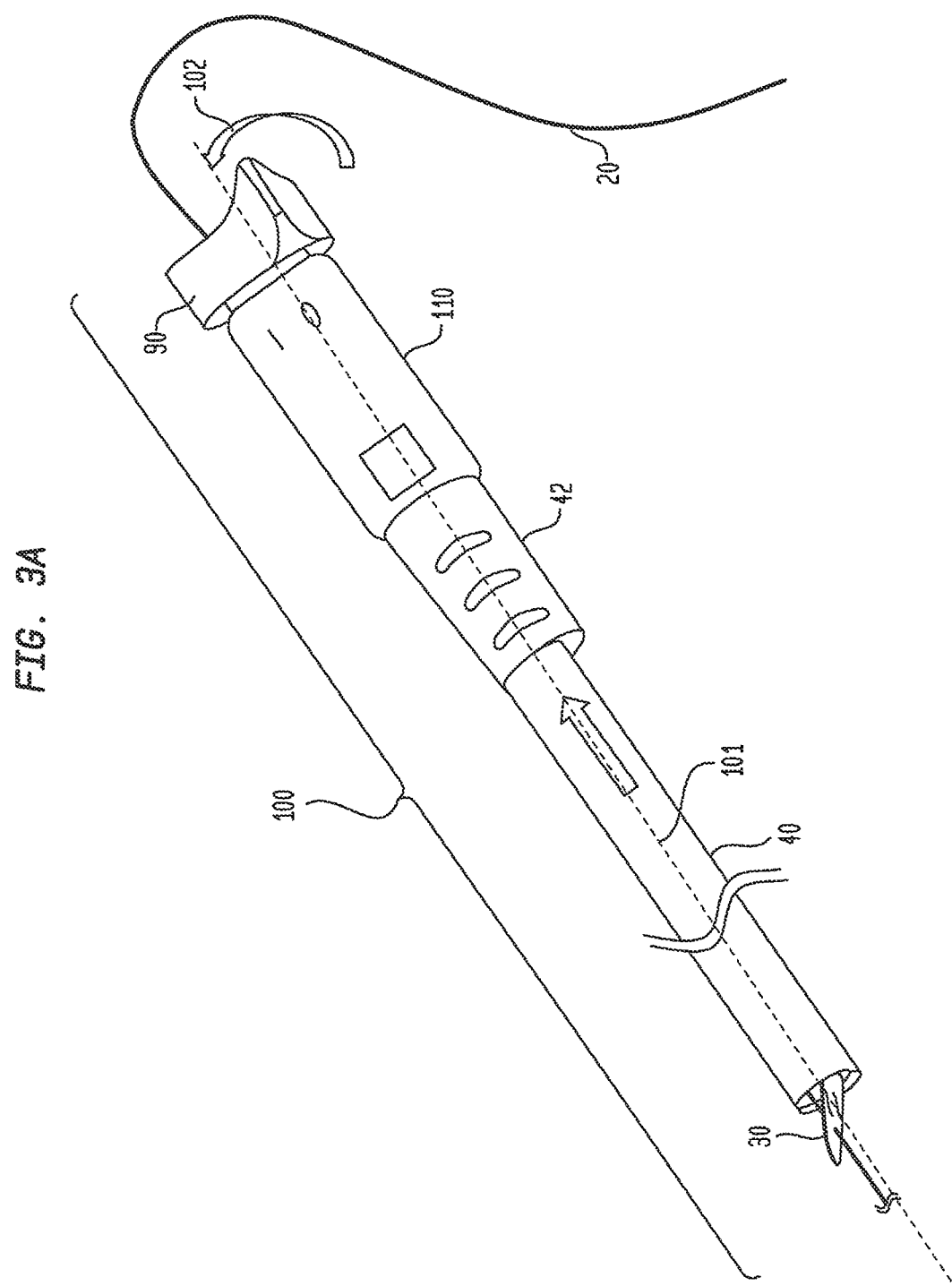

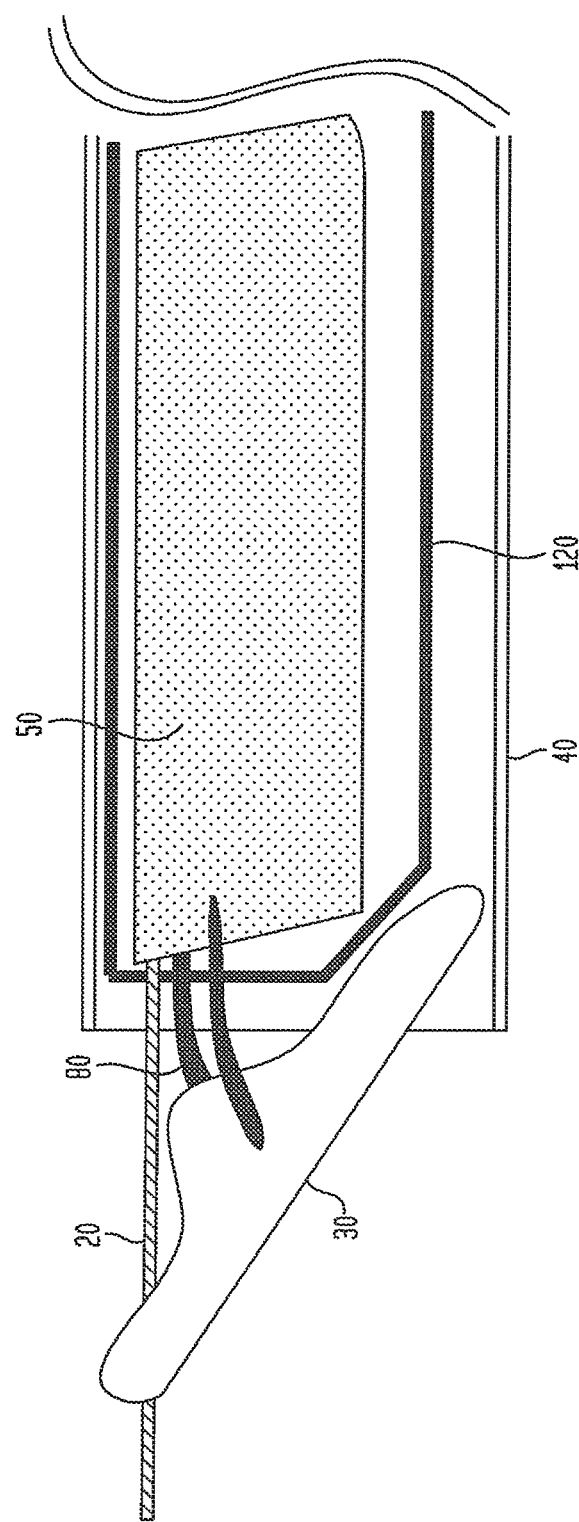

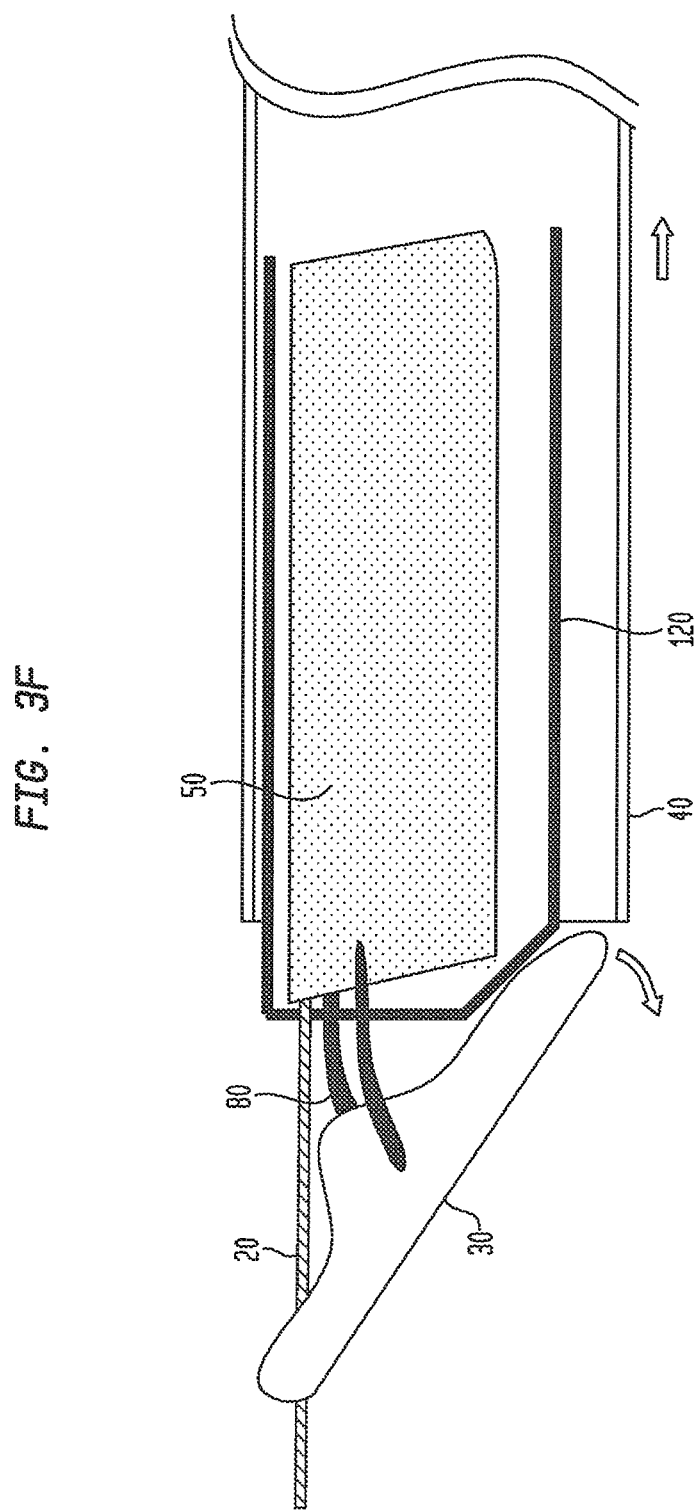

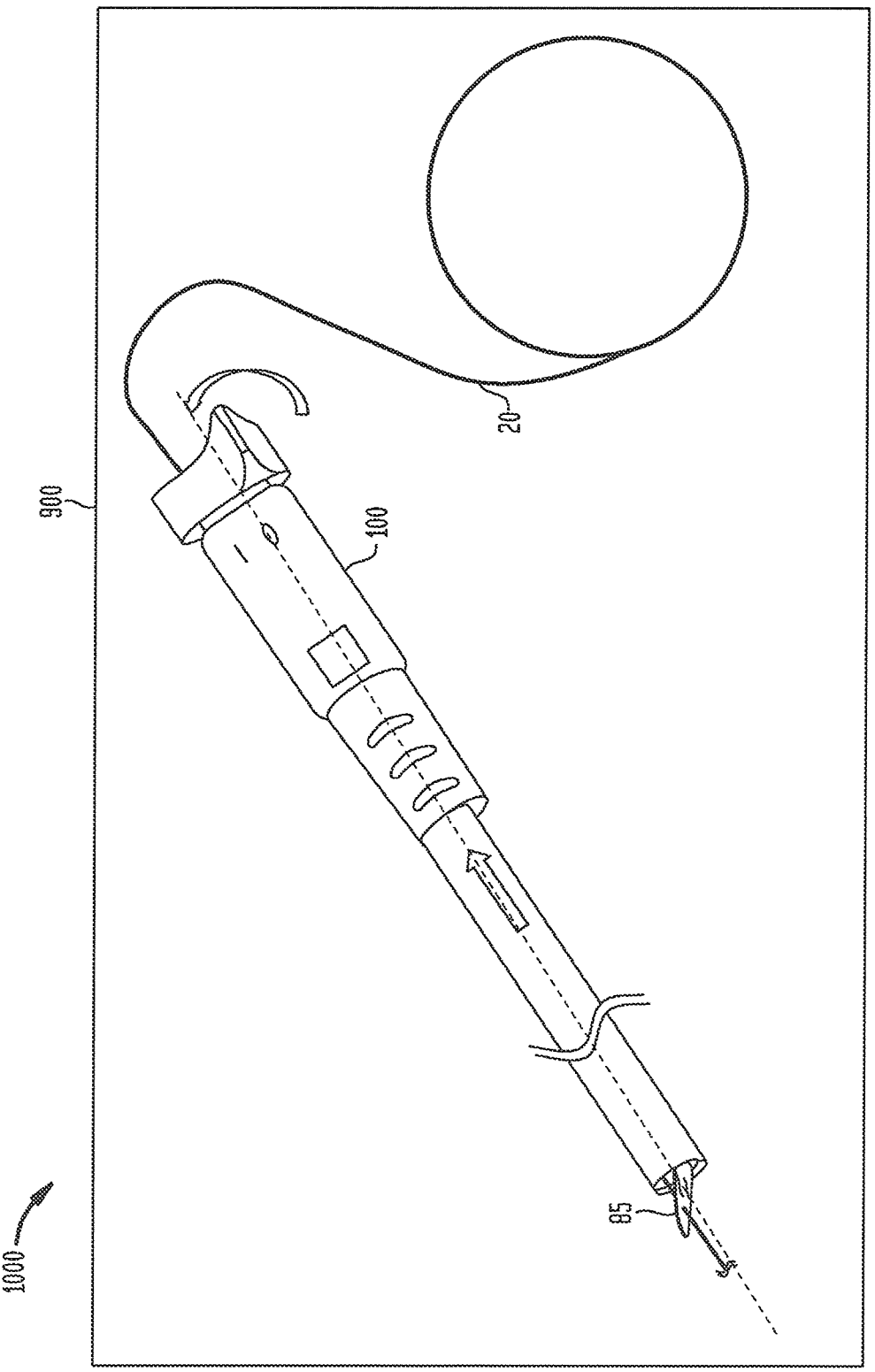

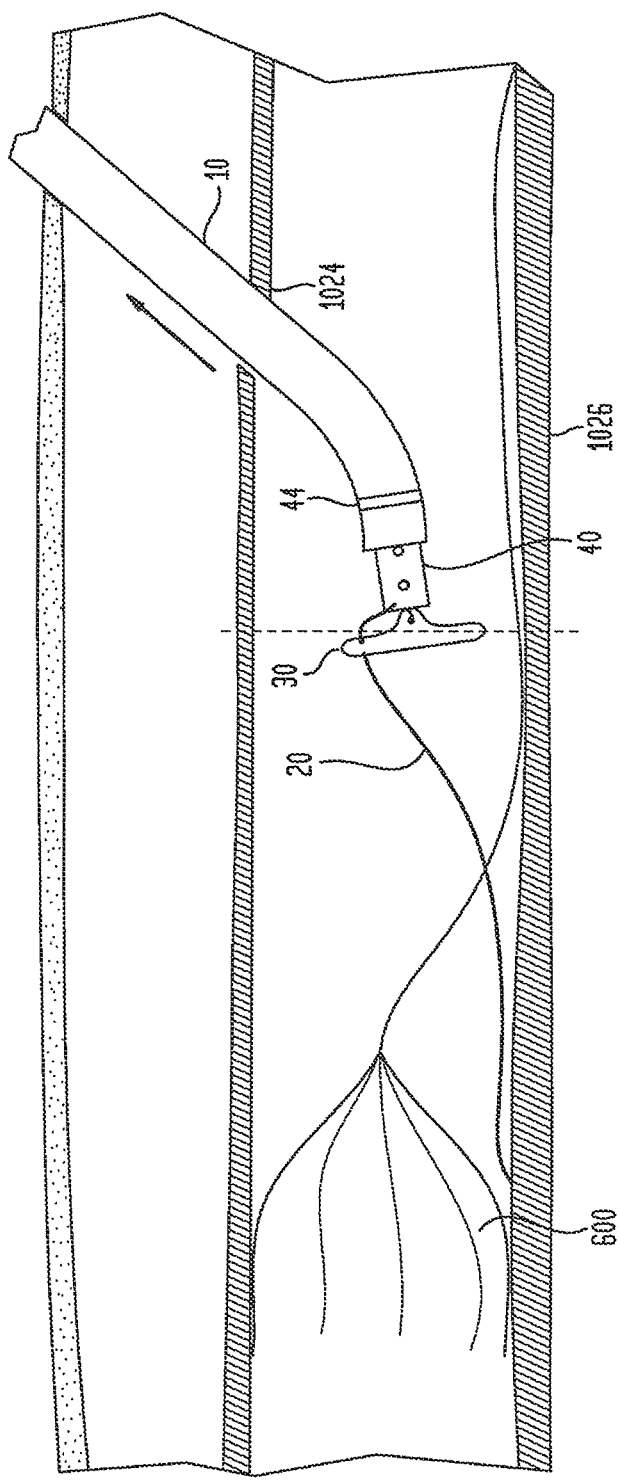

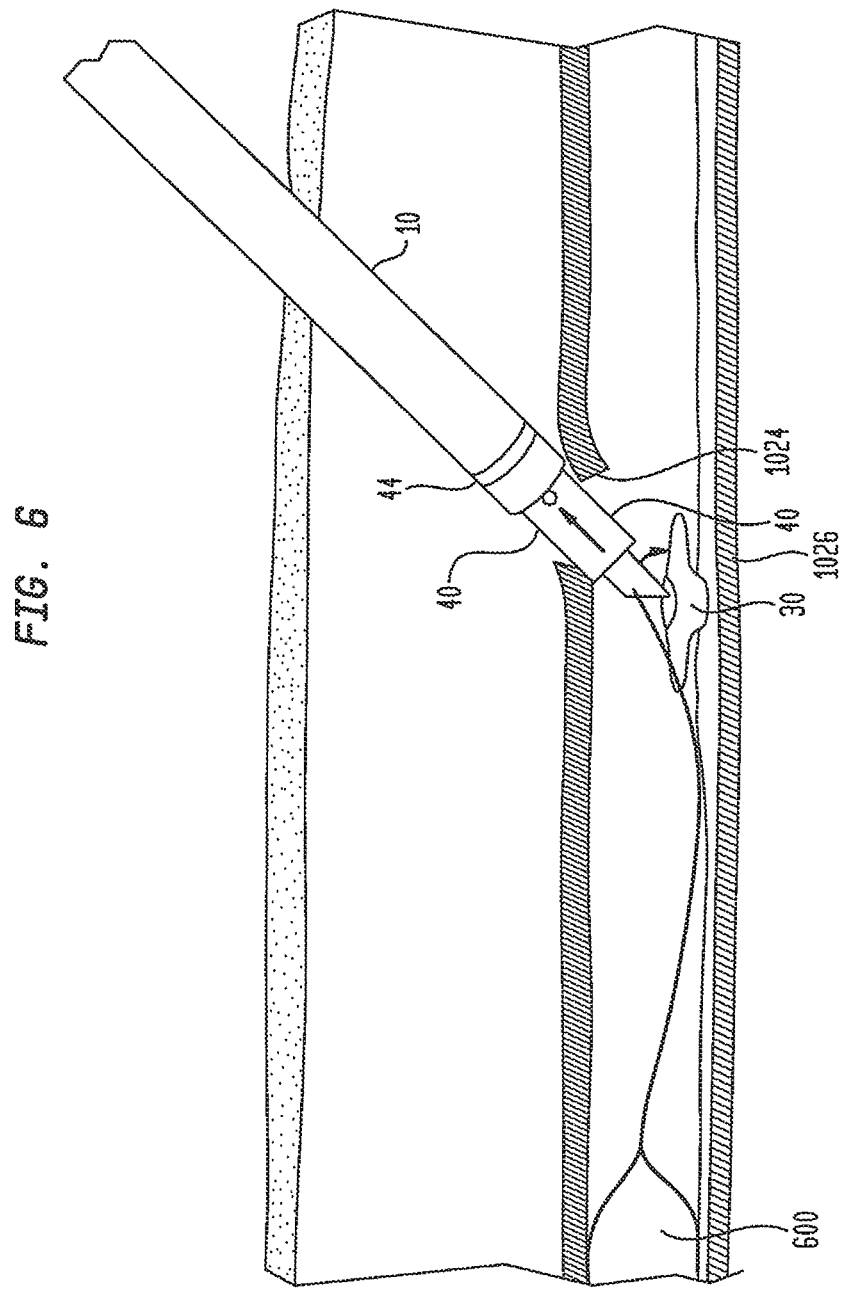

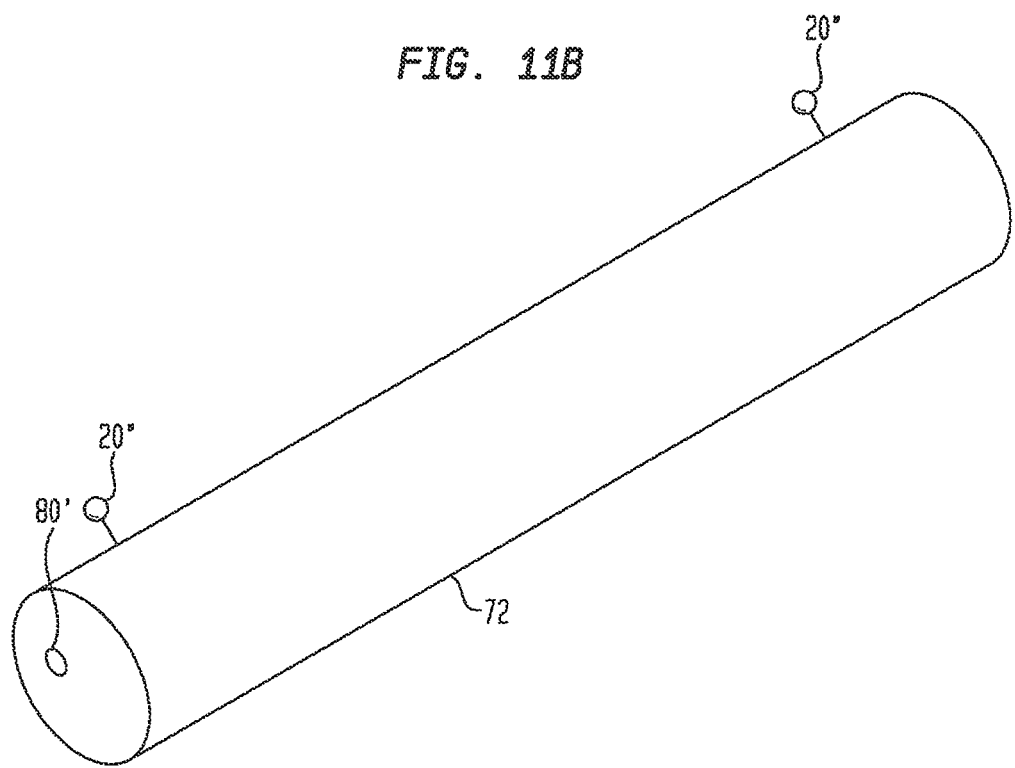

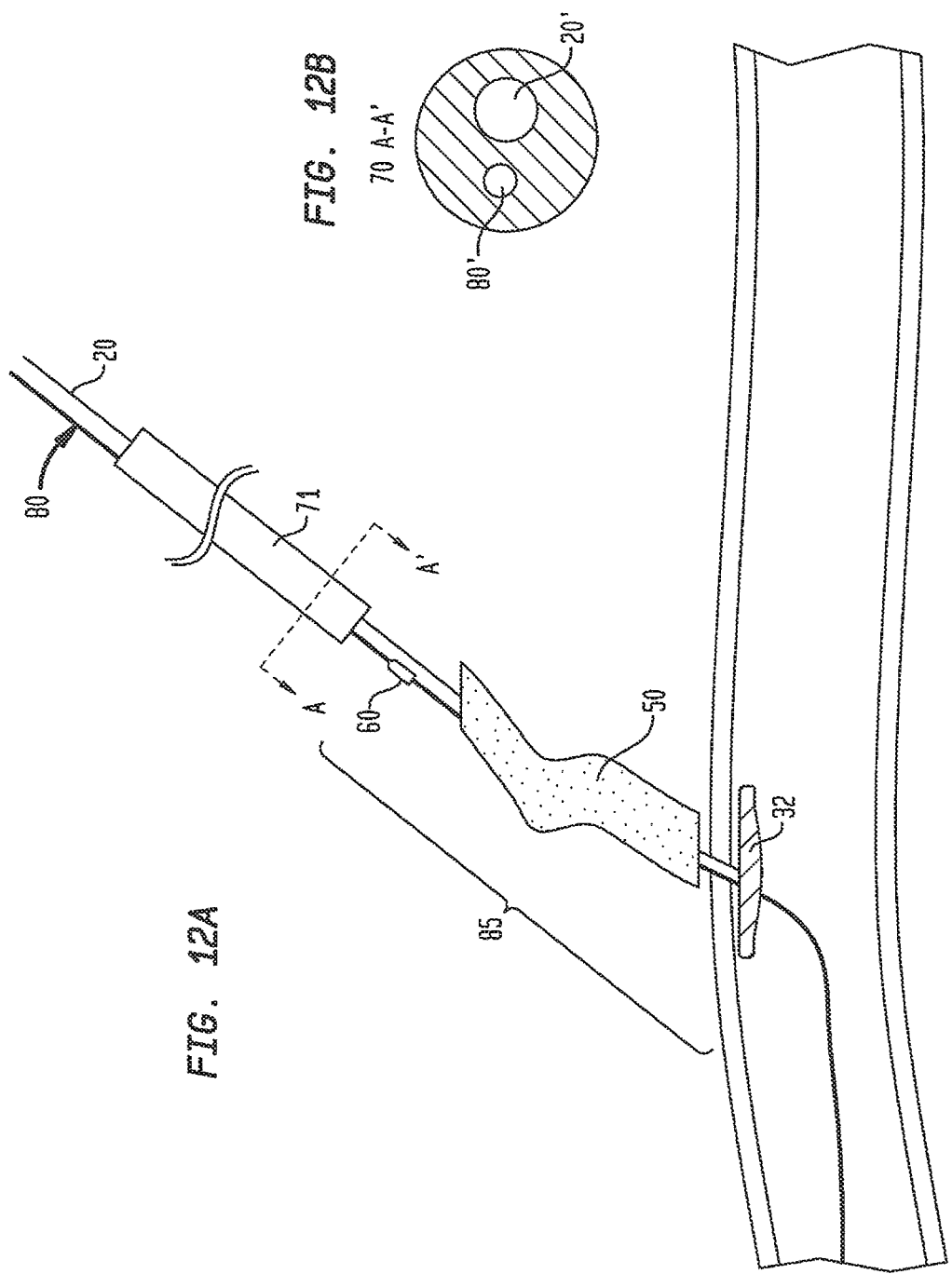

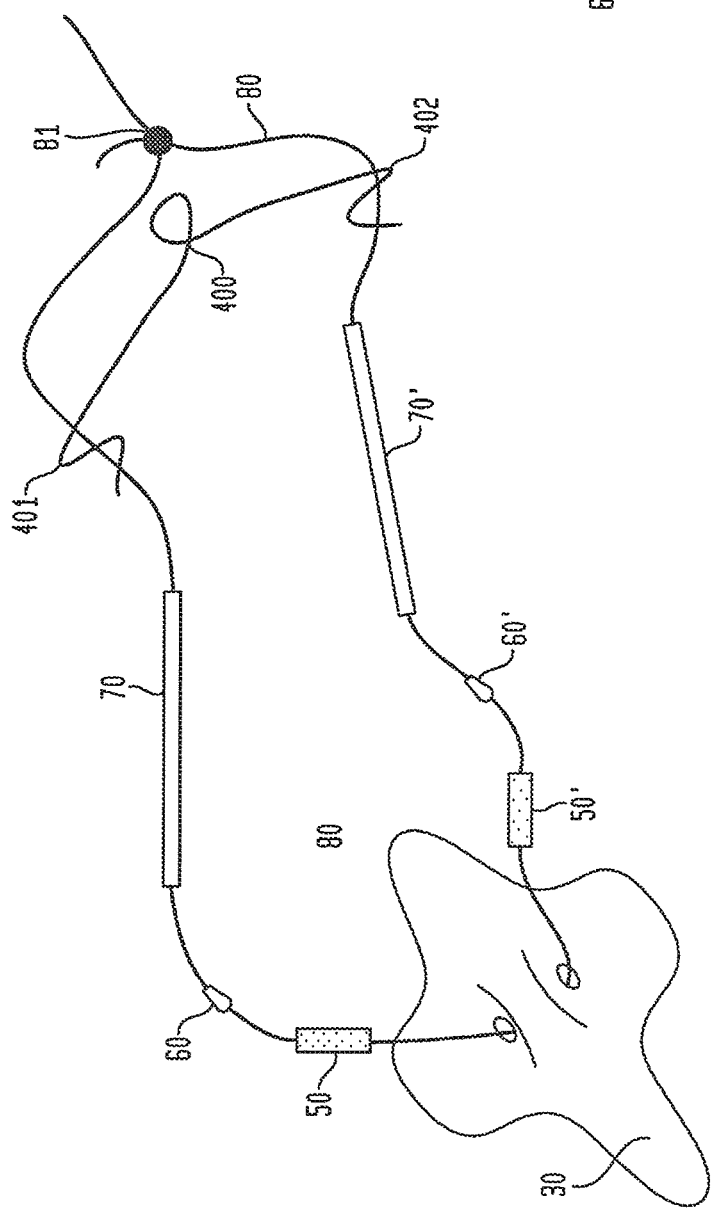
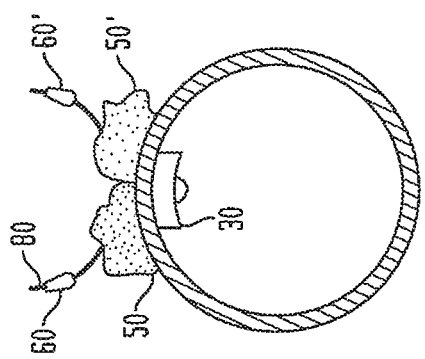

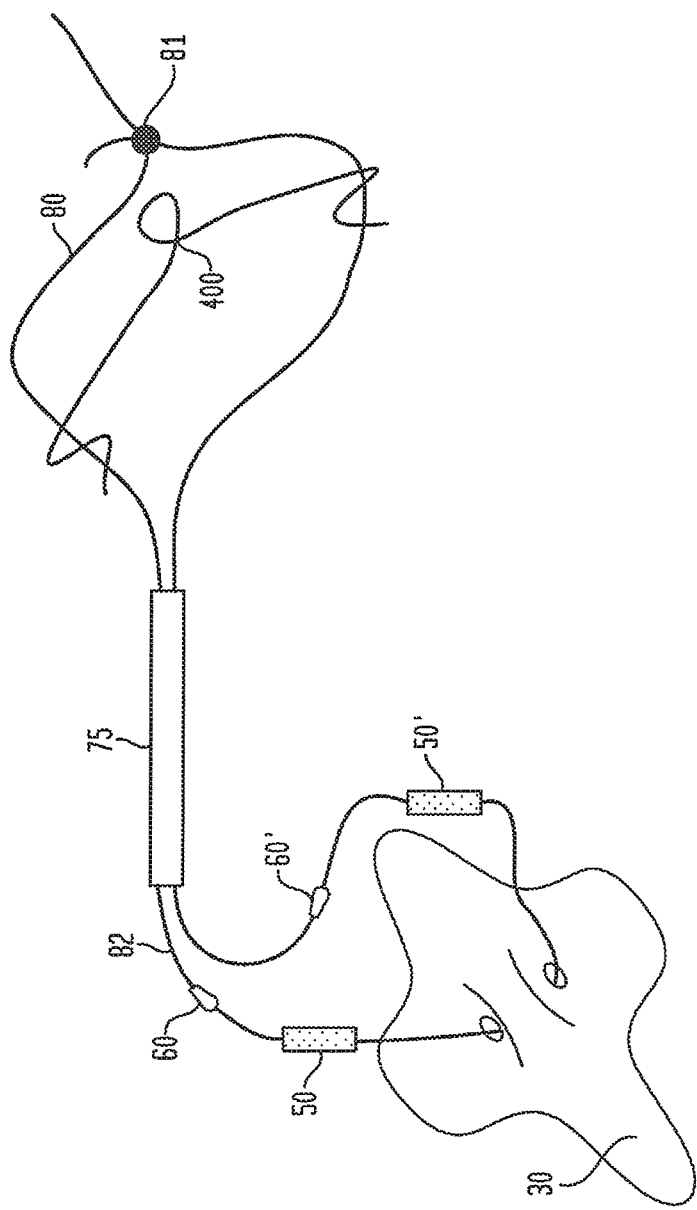

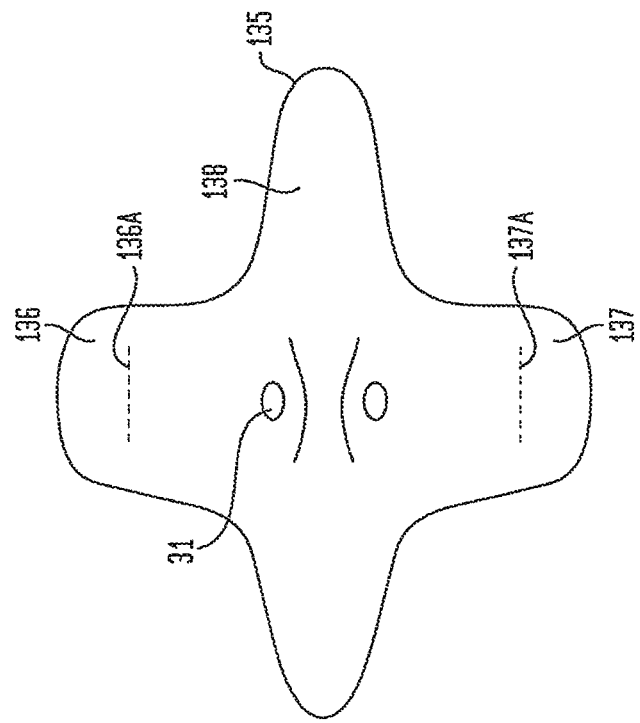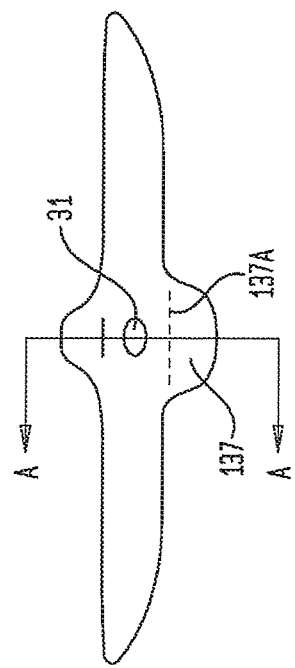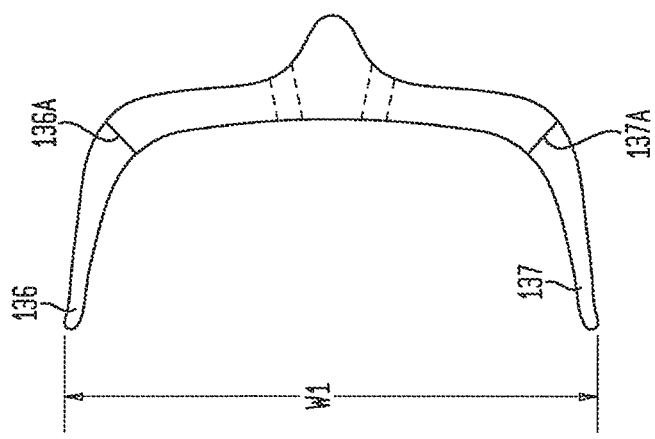

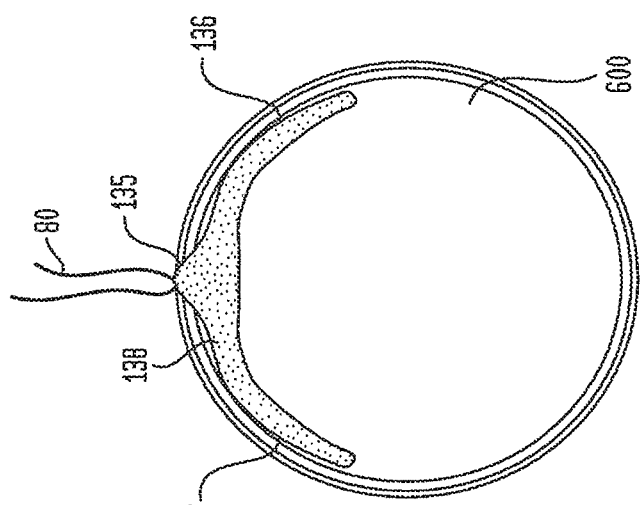
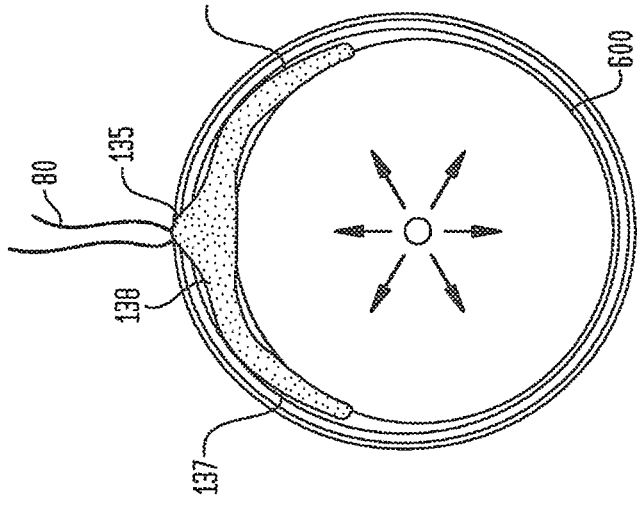
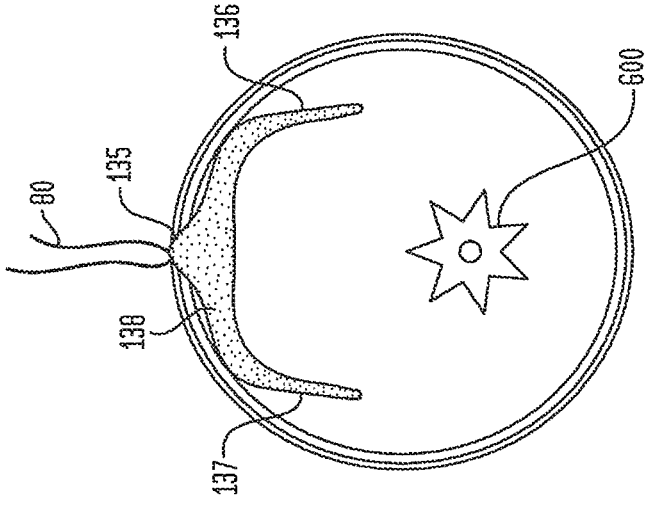

200
VASCULAR CLOSURE DEVICES AND METHODS OF USE

CROSS REFERENCE TO RELATED APPLICATIONS

This application is a National Stage Application filed under 35 U.S.C. 371 of International Application No. PCT/US2014/022416, filed Mar. 10, 2014, which claims priority to U.S. Provisional Application No. 61/794,776, filed Mar. 15, 2013, the contents of which are hereby incorporated by reference as set forth in their entirety herein.

BACKGROUND

U.S. Pat. No. 5,282,827 (hereinafter, the '827 patent), entitled Hemostatic Puncture Closure System and Method of Use, discloses systems for sealing a percutaneous incision or puncture in a blood vessel. The systems of the '827 patent comprise a closure device, an introducer, and a deployment instrument including a carrier for the closure device. The closure device has three basic components, namely, a sealing member, an intra-arterial anchor, and a positioning member.

The sealing member is in the form of an elongate, rod-like plug, e.g., a compressed hemostatic, resorbable collagen sponge or foam. This plug member is arranged for sealing the puncture. The anchor is an elongate, stiff, low-profile member which is arranged to be seated inside the artery against the artery wall contiguous with the puncture. The anchor is molded of non-hemostatic resorbable polymer similar to conventional resorbable sutures.

The positioning member comprises a filament, e.g., a resorbable suture. The filament connects the anchor and the collagen plug (sealing member) in a pulley-like arrangement, and includes a portion extending outside the patient's body. The outwardly located filament portion is arranged to be pulled, i.e., tension applied thereto, after the anchor is located within the interior of the artery and in engagement with the inner wall of the artery contiguous with the incision or puncture. The pulling on the filament causes its pulley arrangement to move the plug in the puncture tract toward the anchor. A tamper forming a portion of the deployment instrument is slid down the filament while the filament is maintained in tension to gently tamp the plug in the puncture tract to cause the plug to deform so that its diameter increases. Tension is maintained on the filament by use of an externally located spring during the tamping procedure.

The expansion of the plug within the tract is enhanced by the fact that it is formed of a compressed collagen so that it expands in the presence of blood within the puncture tract. The expansion of the plug within the puncture tract serves to hold it in place. Moreover, the closure device quickly becomes locked in place through the clotting of the hemostatic collagen plug within the puncture tract. The spring serves to hold the plug in its deformed state until such time that the plug is locked in place by the hemostatic clotting action. Once this has occurred, so that the plug is effectively locked within the puncture tract, the externally located spring can be removed. This typically occurs after approximately 30 minutes. After the spring is removed, the filament is severed at the top of the tamper. The tamper is then removed and the remaining portion of the filament is cut subcutaneously prior to the discharge of the patient. The portion of the filament connecting the anchor to the plug remains in tension, thereby holding the closure device permanently in place until it is eventually absorbed by the patient's body.

U.S. Pat. No. 5,662,681 (hereinafter, the '681 patent), entitled Self-locking Closure for Sealing Percutaneous Punctures, also teaches systems for sealing a percutaneous incision or puncture in a blood vessel.

SUMMARY

In accordance with an embodiment, a closure device system for sealing a percutaneous puncture in a vessel wall can comprise a toggle configured to engage an interior surface of the vessel wall, a plug configured to engage an exterior surface of the vessel wall, and a suture that extends through the plug and through the toggle along at least a first direction so as to couple the toggle to the plug such that the plug is proximal to the toggle. The system can further comprise a tube that extends through the plug and through the toggle along the first direction such that a distal end of the tube is disposed distally to the toggle. The tube can define a guidewire lumen that extends therethrough along the first direction. And the guidewire lumen can be configured to receive a guidewire that protrudes from the vessel wall such that the plug, toggle, and tube are slidable along the guidewire toward the vessel wall.

In accordance with another embodiment, a closure device system for sealing a percutaneous puncture in a vessel wall can comprise a closure device configured to seal the puncture, and a deployment device. The deployment device can include a delivery tube that is elongate along a first direction and is configured to hold the closure device in a pre-deployment state, and a guidewire tube that extends through at least a portion of the closure device within the delivery tube and along the first direction such that the guidewire tube moves relative to the closure device as the closure device is deployed from the delivery tube. The guidewire tube can define a lumen that extends therethrough along the first direction and can be configured to (i) receive a guidewire that protrudes from the vessel wall such that the closure device and deployment device are together slidable along the guidewire toward the vessel wall.

In accordance with another embodiment, a method of sealing a percutaneous puncture in a body passageway of a living being can comprise the steps of inserting a guidewire into the body passageway such that the guidewire extends from outside the body passageway, through the puncture, and into the body passageway; inserting the guidewire into a guidewire lumen defined by a guidewire tube of a closure device system, the closure device system further including a toggle and a plug slidably coupled to the guidewire tube; and moving the closure device system along the guidewire such that the toggle enters the body passageway through the puncture.

BRIEF DESCRIPTION OF THE DRAWINGS

The foregoing summary, as well as the following detailed description of an example embodiment of the application, will be better understood when read in conjunction with the appended drawings, in which there is shown in the drawings example embodiments for the purposes of illustration. It should be understood, however, that the application is not limited to the precise arrangements and systems shown. In the drawings:

FIG. 1 is a diagram showing the clinical setting of a large bore sheath and a guide wire;

FIG. 2A is a diagram depicting a closure device;

FIG. 3A is diagram of an exemplary deployment instrument according to an exemplary embodiment;

FIGS. 3B-3F depicts additional details of the deployment instrument of FIG. 3A;

FIG. 3G depicts an exemplary kit according to an exemplary embodiment;

FIG. 5 is a diagram showing how the sheath and the closure device are positioned in the large arteriotomy;

FIG. 6 a diagram showing how the toggle is released in preparation for deployment;

FIGS. 11A-11C depict exemplary tampers;

FIG. 12A-12B depict exemplary features of a tamper;

FIGS. 20A-20B depict an embodiment utilizing a plurality of plugs;

FIG. 21 depicts an embodiment utilizing a dual-lumen tamper;

FIGS. 24A-24D depict an alternate embodiment of a toggle;

FIGS. 25A-25C depict an end view of use of a balloon to hold a toggle against an artery;

DETAILED DESCRIPTION OF ILLUSTRATIVE EMBODIMENTS

Figure 2B:
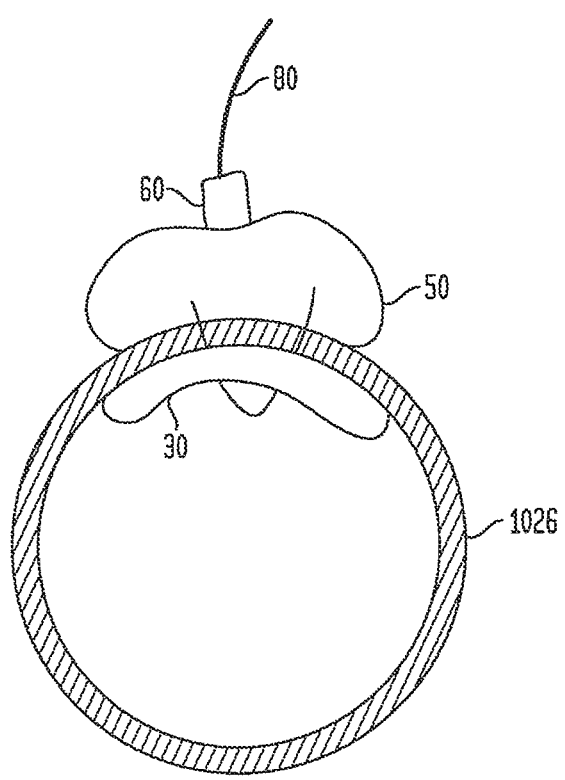
FIG. 2B is a cross-sectional view of the closure device of FIG. 2A.

Some exemplary embodiments are directed towards wound (puncture) closure devices, systems and methods, and wound (puncture) closure device deployment instruments and methods and systems of utilization thereof, associated with closing a relatively large puncture (wound) of an artery, such as by way of example, a femoral artery. Such a large puncture may exist as a result of a balloon aortic valvulopasty (BAV) and/or percutaneous aortic valve replacement (PAVR) procedure and/or a related procedure, which utilize access sheaths from the 18 to 24 F size. Hereinafter, these procedures (BAV, PAVR and related procedures) may be referred to as the "referenced vascular treatment procedures."

An exemplary embodiment of the wound closure system detailed below and some variations thereof interface with an intravascular guide wire. Accordingly, some exemplary embodiments of use of thereof will first be detailed, followed by a discussion of some specific features to the wound closure system of some exemplary embodiments.

In an exemplary embodiment, a needle cannula usable in a valvulopasty and/or percutaneous aortic valve replacement procedure is inserted into an artery. Such a needle may correspond to, by way of example and not by way of limitation, a needle usable in the Seldinger method.

While the needle cannula is in place (extending into the artery), a guide wire is passed through the cannula of the needle a desired distance into the artery (sufficient for the teachings detailed herein and/or variations thereof to be practiced, and/or other procedures to be practiced). In an exemplary embodiment, the guide wire is a so-called thirty-five thousandths of an inch guide wire. In an exemplary embodiment, the guide wire is an access guide wire. Once the guide wire is in place, the needle cannula is removed by pulling the needle away from the artery over the guide wire. This leaves the guide wire in place, with a portion thereof extending the desired distance (or thereabouts) into the artery. This further leaves an incision through which the guide wire extends. As will be detailed below, in an exemplary embodiment, the guide wire is part of a wound closure device deployment instrument, although in other exemplary embodiments, the guide wire is a separate element.

An introducer sheath, such as a large bore sheath, is passed over the guidewire, through the incision and into the artery, as depicted in FIG. 1, where element 10 is a large bore sheath, element 20 is a guide wire, element 1026 is a femoral artery (depicted in cross-sectional view), element 1024 is the puncture in the artery (wound in the artery), element 1025 is the tract leading to the puncture 1024 and element 1028 is the skin. By tract it is meant the passageway in the tissue located between the artery 1026 and the skin 1028 of the being, and which is formed when the artery is punctured percutaneously.

It is noted that the scene depicted in FIG. 1 may be achieved through other steps than those just depicted by way of example. Any method or methods that result in the human tissue-medical device interface regime depicted in FIG. 1 and/or variations thereof, which enable the teachings herein and/or variations thereof and/or result in the utility of the teachings detailed herein and/or variations thereof, may be used in some embodiments. Indeed, the aforementioned actions may be part of or be substituted by actions that are part of the referenced vascular treatment procedures. In any event, after executing such actions, a large bore sheath 10 remains in a vessel, such as the common femoral artery, as depicted by FIG. 1 and/or a variation thereof.

As can be understood by the diagram of FIG. 1 and attention to the sizing (unless otherwise noted, the drawings herein are drawn to scale), the sheath 10 is relatively large in relation to the inner diameter of the vessel (e.g., it has an inner diameter and/or an outer diameter of about 0.4, 0.5, 0.6, 0.7 and/or 0.8 or more times the size of the inner diameter of the artery, as measured on a plane lying normal to the longitudinal axes of these tubular structures). In this regard, the sheath 10, as it is a large bore sheath, requires a transverse slit (i.e., a slit extending axially) in the artery, which will be relatively large (sufficient to receive the sheath 10 therethrough, after the elastic nature of the artery is taken into account).

In an exemplary embodiment, the guidewire 20 is utilized for advancement of a wound closure device deployment instrument through the sheath 10 in general, and movement of a wound closure device in particular along the guide wire. It is noted that some exemplary details of the deployment instrument and closure device are provided below. However, in some embodiments, the deployment instrument and/or closure device may correspond to the deployment instrument and/or wound closure device of any of the above referenced applications as modified to interface with the large bore sheath 10 and/or closure device and/or deployment instrument detailed below, wherein the closure device may correspond to the closure device of any of the above referenced applications as modified to close such a large opening in the artery (e.g., an opening large enough to permit a sheath of 18 F to fit through as depicted in the FIGS.).

Also shown in FIG. 1 is a PTA balloon 600 inserted proximally or from a contralateral puncture site. This balloon is utilized to block blood flow proximal to the large bore puncture site (i.e., the site depicted in FIG. 1), and as an entry for contrast dye. Balloon 600 is depicted in an uninflated or semi-inflated state coupled to guidewire 610 or a balloon shaft. In use, inflation fluid is pumped to the balloon, to inflate the balloon 600. It is noted that some embodiments may not include the balloon 600/may not utilize the balloon 600.

An exemplary embodiment of a closure device will now be briefly described in the context of the environment of FIG. 1, with some additional details of the closure device being provided further below.

At some point during the aforementioned procedure, the incision in the artery is utilized for whatever medical purposes associated with the utility of the incision. After such utilization, there is utilitarian value in closing the incision. An exemplary embodiment of a closure device for closing the incision will now be described in the context of the artery 1026.

FIG. 2A depicts an exemplary closure device 85 closing puncture 1024. The closure device 85 includes toggle 30, plug 50 (often referred to in the art and herein as a sealing member or collagen pad, or simply collagen), lock 60, and suture (also referred to in the art and herein as filament) 80, in the fully deployed state with the suture 80 cut below the skin level 1028 (the occlusion balloon is depicted in the uninflated/deflated condition. FIG. 2B depicts a cross-sectional view of the artery 1026, which details the fit of the toggle 30 to the internal diameter of the artery, and also depicts the profile of the toggle 30 with respect to the longitudinal axis of the artery 1026.

FIGS. 2A and 2B depict by way of example the closure unit 85 (comprising toggle 30, collagen 50, lock 60, and suture 80) in the fully deployed state with the suture 80 cut below the skin level, and the occlusion balloon deflated to re-establish blood flow in the vessel and depict the fit of the toggle 30 to the internal diameter of the vessel, highlighting the low profile of the toggle design, as seen along the longitudinal axis of the vessel.

In an exemplary embodiment, the closure device 85 can correspond to any of the above referenced applications as modified to close such a large opening in the artery (e.g., an opening large enough to permit a sheath of 18 F to fit through as depicted in the FIGS.) and/or to provide an alternate access pathway if needed during the procedure in which the method is executed.

For example, suture (filament) 80 can correspond to filament 34 of U.S. patent application Ser. No. 13/111,653 (hereinafter, the '653 application) filed on May 19, 2011, entitled DEPLOYMENT INSTRUMENT FOR CLOSURE DEVICE FOR PERCUTANEOUSLY SEALING PUNCTURES, the teachings of the '653 application relating to the construction and features of the filament being incorporated by reference herein for use in an embodiment herein. Lock 60 can correspond to lock 36 of the aforementioned '653 application (or any other lock detailed therein and variations thereof), the teachings of the '653 application relating to the construction and features of the lock being incorporated by reference herein for use in some embodiments herein. Collagen 50 can correspond to plug 30 of the aforementioned '653 application, although it is noted that the size of plug 30 may vary from that disclosed in the '653 application, the teachings of the '653 application relating to the construction and features of the plug 30 being incorporated by reference herein for use in an embodiment herein.

While the toggle 30 is different in size and geometry from that explicitly disclosed in the '653 application with respect to that anchor 32 detailed therein, in an exemplary embodiment, the toggle 30 corresponds to the anchor 32 of the '653 application in a modified form in accordance with the teachings detailed herein and/or variations thereof, the applicable teachings of the '653 application relating to the construction and features of the anchor 32 being incorporated by reference herein for use in an embodiment herein.

In an embodiment, the suture 80 is a braided multifilament size 2-0 PLLA suture. The suture 80 can be made from any synthetic absorbable plastic material that degrades as needed.

The plug 50 comprises a strip of a compressible, resorbable, collagen foam which includes one or more apertures through which portions of the suture 80 extend. In an embodiment, the plug 50 is a collagen pad made of a fibrous collagen mix of insoluble and soluble collagen that is cross linked for strength. In an embodiment, the collagen may be obtained from the connective tissue of animals. The collagen may be purified from the subdermal layer of cowhide.

The lock 60 comprises a cylindrical piece of resorbable iron and/or stainless steel crimped in a manner to provide a limited amount of resistance to movement along the suture 80.

An embodiment of the toggle 30 is constructed of a 50/50 polylactic-cogycolic acid or other synthetic absorbable polymer that degrades in the presence of water into naturally occurring metabolites (e.g., water and $CO2$). In an embodiment, the toggle 30 is a monolithic structure formed by a bio-absorbable polymer.

It is noted that the aforementioned closure device 85 is an exemplary closure device, and alternate embodiments of such may be used in some embodiments. By way of example only and not by way of limitation, the aforementioned crimped lock may not be present, and instead, the filament is looped and/or suturing is utilized to hold the relative locations of the elements of the closure device 85 (e.g., plug 30 and toggle 30). By way of example and not by way of limitation, the closure device may correspond to, scaled for application with large bore application or unscaled, that detailed in U.S. Pat. No. 5,282,827 (hereinafter, the '827 patent) and/or variations thereof, the contents of which are incorporated herein by reference in their entirety with respect to the closure device taught therein. Further by way of example and not by way of limitation, the closure device may correspond to, scaled for application with large bore application or unscaled, that detailed in U.S. Pat. No. 5,662,681 (hereinafter, the '681 patent) and/or variations thereof, the contents of which are incorporated herein by reference in their entirety with respect to the closure device taught therein. Any device, system and/or method of closing the puncture that utilizes a component that fits into the artery to provide a reaction element (e.g., toggle 30) against a force applied thereto associated with closing the puncture and/or any device, system and/or method of closing the puncture that utilizes a plug (e.g., collagen plug 50) may be used in some embodiments. In some other embodiments, any device, system and/or method of closing the puncture may be utilized.

An exemplary puncture (wound) of which the teachings detailed herein and/or variations thereof can be utilized to close or otherwise be associated with is a puncture in an artery having a diameter (inner or outer) of about 10 mm, although such teachings can also be applicable to such having a diameter (inner or outer) of about 5, 6, 7, 8, 9, 10, 11, 12 and/or about 13 mm or more, or any value in between these values and/or any ranges encompassing some or all of these values (including ranges being bounded by the in between values). In an exemplary embodiment, the puncture extends over an arc, transverse to a longitudinal axis of the artery (about the circumference normal to the longitudinal axis) of about 90 degrees, although in some embodiments, the arc extends 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175 and/or about 180 degrees, or any value in between these values and/or any ranges encompassing some or all of these values (including ranges being bounded by the in between values). By way of example, the puncture may extend along an arc having a length of 8 mm, although in some embodiments, the length is about 3, 4, 5, 6, 7, 8, 9, 10, 11, 12, 13, 14 and/or about 15 mm or any value in between these values and/or any ranges encompassing some or all of these values (including ranges being bounded by the in between values).

As noted above, some additional exemplary features of the components that make up the closure device 85 are further detailed herein. Prior to that, however, a brief discussion of an exemplary deployment instrument is provided (with additional details pertaining to the deployment instrument being provided further below) for deploying a closure device such as closure device 85 and/or other equivalents thereof and/or variations thereof.

FIG. 3A depicts an exemplary deployment instrument 100 according to an exemplary embodiment, configured to deploy the closure device 85. As described herein, deployment instrument 100 includes a closure device 85 and a guide wire 20. However, in other embodiments, the deployment instrument may not include one or both of these elements.

Briefly, deployment instrument 100 is configured to be inserted into sheath 10. Deployment instrument 100 includes a release tube 40 and a handle 110. Release tube 40 is configured to move relative to handle 110 and release tube support 42 along longitudinal axis 101 via actuation of lever 90 clockwise or counter-clockwise relative to the handle, as depicted by arrow 102. That is, movement of lever 90 moves release tube 40 (sometimes referred to herein as restraining tube 40) inward/proximal to release the toggle 30.

More particularly, FIG. 3B depicts a cross-sectional view of the distal end of the deployment instrument 100, depicting additional components of the deployment instrument 100. As may be seen, deployment instrument 100 includes a delivery tube 120 that is located within release tube 40. The plug 50 of closure device 85 is located in the delivery tube 120, with filament 80 extending past plug 50 to toggle 30. It is noted that plug 50 may partially extend outside of tube 120. In an exemplary embodiment, delivery tube 120 corresponds to a carrier assembly (which can include only the delivery tube or can include additional components).

Figure 3C:
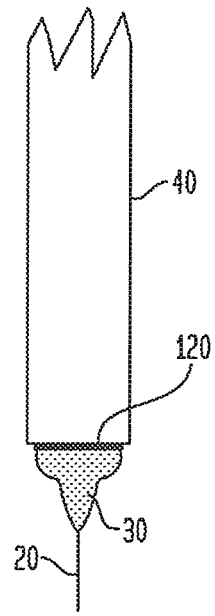
Figure 3D:
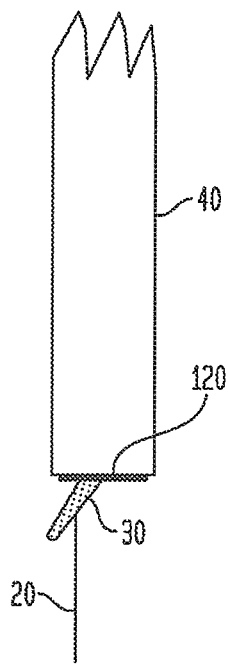

As may be seen, toggle 30 is located such that it is at least partially located in the release tube 40. In some embodiments, it may be fully located in the release tube 40 (i.e., no part of the toggle 30 extends past the distal tip of the tube 40. Toggle 30 is held in place by filament 80. As will be described in more detail below, guide wire 20 extends through delivery tube 120 and release tube 40, as well as through toggle 30 and/or plug 50. In this regard, FIG. 3C depicts a top view of the distal end of deployment instrument 100, with FIG. 3D depicting a side view thereof for comparison purposes. As may be clearly seen in FIG. 3C, the guide wire 20 extends through toggle 30 (through the longitudinal center of the toggle 30). In an exemplary embodiment, the association of the guide wire 20 with the toggle 30 as detailed herein and/or variations thereof can have utility in that such may ensure or otherwise effectively and/or substantially increase the statistical probability (at least with respect to that in the absence of the guide wire association) that the toggle is at least generally if not substantially or about perfectly centered relative to the incision in the artery.

In an exemplary embodiment, irrespective of the presence or absence of the guide wire 20, the plug 50 is held within delivery tube 120 in a manner that is similar to and/or a manner that is the same as that associated with the plug 30 tubular carrier 102 of the '653 application, the teachings thereof relating to such being incorporated by reference herein for use in an embodiment herein.

Figure 3E:
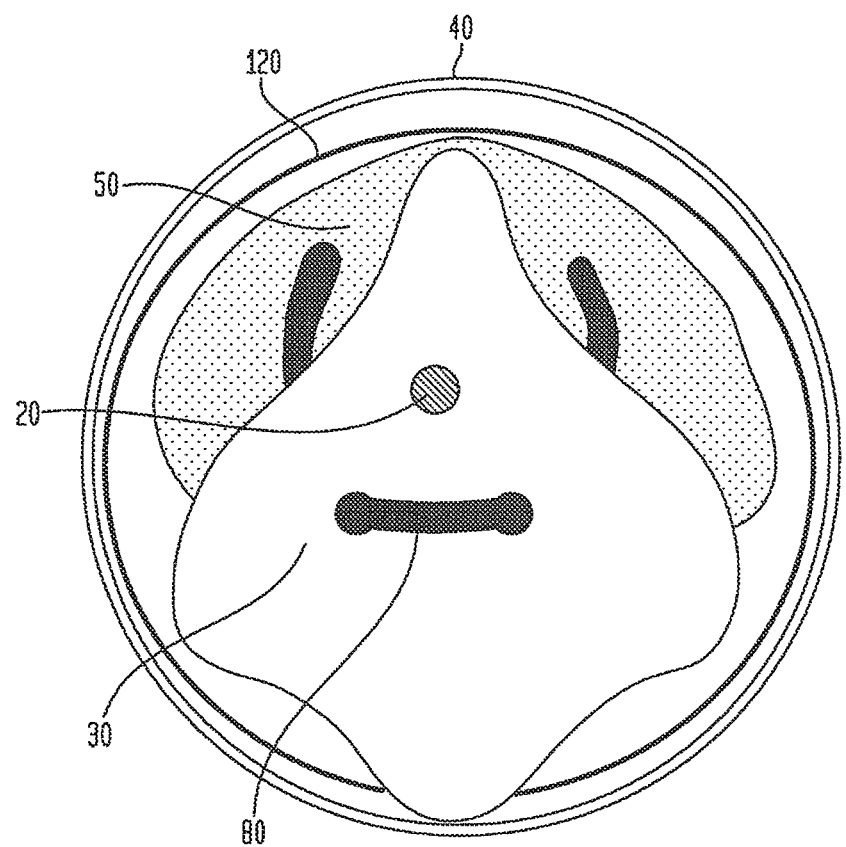

FIG. 3E depicts an end view of the deployment instrument 100 looking at the distal end thereof.

In operation, movement of lever 90 on the delivery handle 110 of the deployment instrument 100 in the direction of arrow 102 moves the release tube 40 in the proximal direction to about the location depicted in FIG. 3F (although the tube 40 may be moved to other locations in other embodiments, such as to a more distal location). As may be seen, the toggle 30 is now completely outside the release tube 40, and is thus "released."

In an exemplary embodiment, the deployment instrument 100 is a fully integrated system that includes the deployment device 85 and the guide wire 20. In an exemplary embodiment, it is packaged (in, by way of example, a sterilized manner). In an exemplary embodiment, it is packaged in a hermetically sealed package. The guide wire 20 may be wound in a winding with a relatively large radius to avoid kinking the guide wire. FIG. 3G depicts an exemplary closure device kit 1000, including deployment instrument 100, closure device 85 and guide wire 20 sterilized and hermetically sealed in package 900. In an exemplary embodiment, kit 1000 may further include an insertion sheath 10 in package 900 and/or in a separate package attached thereto.

It is noted that in an alternate embodiment, the guide wire 20 is not part of the kit and/or the delivery instrument 100. Instead, it is a separate component that is threaded through the toggle 30 and/or the plug 50 after access to the delivery instrument 100 (and thus the closure device 85) is obtained. Accordingly, an exemplary embodiment includes a method whereby a user, such as a physician or an operation room nurse or other professional passes an end of a guide wire through a hole in the toggle 30 or otherwise associates the toggle 30 with the guide wire, followed by deployment of the closure device 85. The guidewire can also be associated with collagen, tamper, and tensioner.

Use of the deployment instrument 100 will now be detailed with respect to an exemplary deployment method of deploying the closure device 85.

Figure 4:
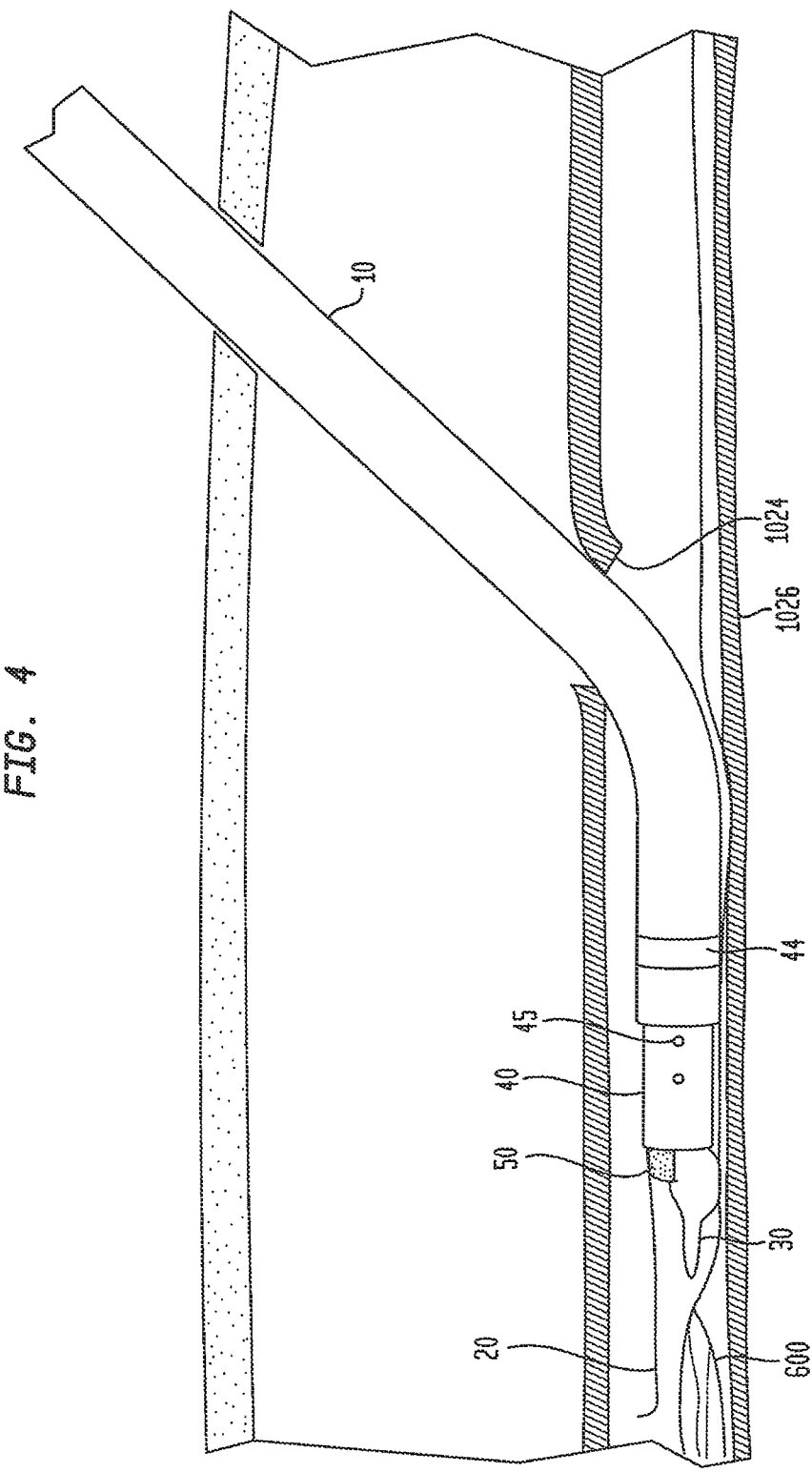
FIG. 4 diagram showing how an exemplary closure device is inserted into the sheath and artery.
Figure 4A:
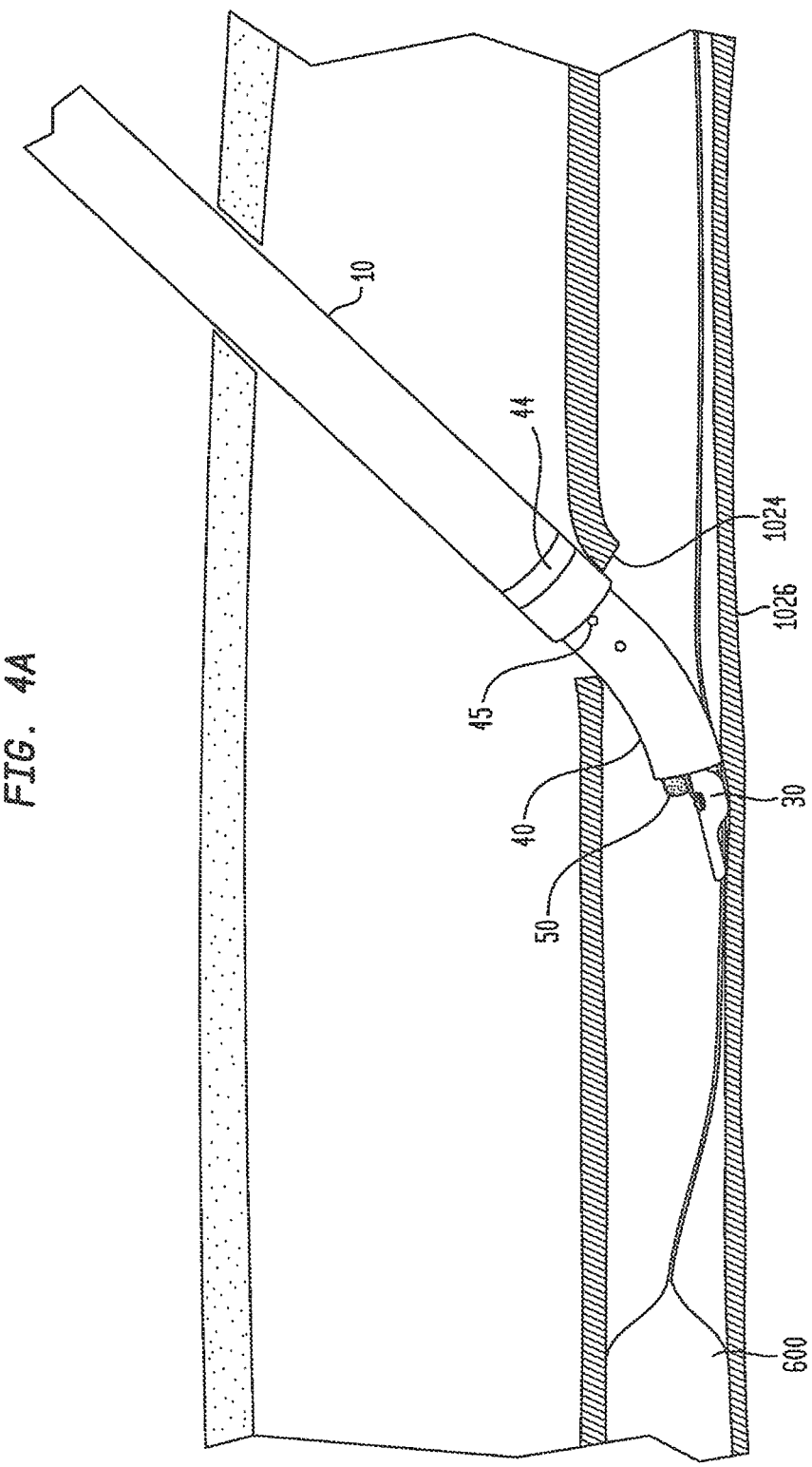

With the sheath 10 in place as seen in FIG. 1, the deployment instrument 100 is inserted into a proximal end (not shown) of sheath 10, and moved through the sheath 10 until the distal end of the instrument 100 end extends out of the distal end of the sheath 10, approximately as shown in FIG. 4. In an exemplary embodiment, the guide wire 20 extends through the deployment instrument 100, and the deployment instrument 100 slides along the guide wire 20 (guide wire 20 and sheath 10 are generally held stationary, relative to artery 1026, while deployment instrument 100 is moved through the sheath 10). In an alternate embodiment, the guide wire 20 moves with the deployment instrument 100, at least to a certain extent.

More particularly, FIG. 4 depicts the relative locations of toggle 30, the end of the delivery tube 120, and the release tube 40 of the deployment instrument 100 with respect to the distal end of the sheath 10. This positioning is achieved by driving the deployment instrument 100 through sheath 10, over the guide wire 20 and/or with the guide wire 20, until the release tube 40, along with the closure device 85 in general and the toggle 30 in particular, as detailed herein and/or variations thereof (where toggle 30 and plug 50 and some of filament 80 is visible in FIG. 4), is positioned as shown. The positioning can be determined via the use of one or more radiopaque markers 44 and/or 45 on the release tube 40. The user, utilizing fluoroscopic methods, can determine the position of radiopaque marker 45, and thus the release tube 40, relative to the end of the sheath 10. In an exemplary embodiment, the user stops driving the deployment instrument 100 into the sheath 10 upon the marker 45 emerging from the sheath 10 (imaged using fluoroscopic methods). It is noted that other devices, systems and/or methods may be utilized to determine or otherwise estimate the position of the end of the release tube 40 relative to the insertion sheath 10. For example, a channel which permits blood to follow through/along the instrument 100 to a location that is visible by the user upon the instrument 100 being so positioned may be used in some embodiments. An exemplary embodiment utilizes some and/or all of the teachings associated with determining or otherwise positioning introducer sheath 28 and/or device 28 of U.S. Pat. No. 5,282,827, the contents of which associated with such teachings are incorporated herein by reference for use in some embodiments. Any device, system and/or method that will enable the position of the instrument 100 to be determined or otherwise estimated may be used in some embodiments. In an alternate embodiment, the sheath 10 is sized and dimensioned and/or the delivery instrument 100 is sized and dimensioned such that movement of the deployment instrument 100 through the sheath 10 stops at a certain point (e.g., a wall of the deployment instrument 10 abuts the sheath 10)) such that the distal end of the deployment instrument 10 extends a distance past the distal end of the sheath 10 a distance having utilitarian value.

As may be seen in FIG. 4, the toggle 30, which in this exemplary embodiment, is smoothly shaped, is partially covered by the release tube 40 upon its emergence from the sheath 10. Because it is exposed, the smoothness has utility in that it can permit relatively smooth entry into the artery and can allow for rearward movement of the closure device within the artery without risk of the toggle 30 catching on any plaque or other obstruction. Given the anatomical nature of the access site and puncture, the release tube 40 (and the delivery tube 100, sheath 10 and guidewire 20 will be slightly curved as may be seen in FIG. 5. This curvature provides a biasing force on the toggle 30 for the release actions.

Upon positioning of the deployment instrument 100 at the desired position relative to the distal end of the sheath 10 (i.e., at the position depicted in FIG. 4), the lever 90 is rotated relative to the rest of the instrument 100 in a direction and by a sufficient amount to retract the release tube 40 a utilitarian distance relative to delivery tube 120, thereby entirely exposing the toggle 30. FIG. 5 depicts such an exemplary retraction. As may be seen, guide wire 20 extends through toggle 30 after retraction of the release tube 40 (and may also extend through the collagen, tamper and tensioner).

Next, sheath 10 is withdrawn from the approximate position depicted in FIG. 5. However, prior to this, balloon 600 optionally can be inflated as shown in FIG. 5. Because the sheath 10 may exit the puncture 1024 when the sheath 10 is withdrawn from the artery, the balloon is inflated under a low pressure to block blood flow from a proximal position at least prior to fully withdrawing the distal end of the sheath 10 from the artery (where blood flow flows from left to right with respect to the frame of reference of FIG. 5).

As just noted the insertion sheath 10 is withdrawn from its previous position, either partially and/or fully out of the artery 1026. FIG. 6 depicts withdrawal of the insertion sheath 10. While the sheath 10 is withdrawn, the relative position of the deployment instrument 100 relative to the artery can change, either by the same amount or by a lesser or greater amount, although in other embodiments, its location relative to the artery may remain the same. Any movement or lack thereof of the instrument 100 relative to the artery may exist in some embodiments providing that it does not negate the utilitarian value of the embodiment. Some such movement may be seen by comparing FIG. 6 to FIG. 5. In this regard, FIG. 6 depicts the deployment instrument 100 in general, and the closure device 85 carried thereby, in a position relative to the puncture 1024 having utilitarian value. (ok, but so what?)

It is noted that in an exemplary embodiment, plug 50 can be withdrawn from tube 120 without contacting the sheath 10 and/or at least without contacting the interior of the sheath 10. This may, in some embodiments, eliminate the possibility that the plug 30 might become stuck in the sheath 10—during the deployment procedure as it expands once leaving the tube 120.

In an exemplary embodiment, a contrast agent is injected distal to the balloon 600. Contrast agent can indicate any leakage at the puncture site and can additionally provide for an outline of the toggle 30 using fluoroscopic methods (The balloon shaft may also be a shaft, and should be coming in from the left, with the wire extending right, and a shaft outlet on the right of the balloon).

The sheath 10 and/or the tube 40, are retracted (moved in the direction that would withdraw them from the patient). The marker is aligned before release as is shown in FIG. 6.

Still referring to FIG. 6, FIG. 6 depicts how the toggle 30 will be released from the biased state with retraction of the release tube 40. The release orients the toggle 30 parallel to the vessel axis. Release is confirmed by the alignment of the distal radiopaque marker 44 with the end of the sheath 10 and/or markings on the handle (not shown). Note that vessel occlusion is maintained during this action, and an outline of the toggle will be visible to the user on the fluoroscope (as will be detailed below, the toggle 30 may include material that is readily apparent through fluoroscopy. Note further that, in an exemplary embodiment, the contact of the most distal portion of the toggle 30 with the artery wall forces the toggle 30 to rotate clockwise upon sufficient movement of the release tube 40, thus aligning the toggle 30 in a manner that will statistically improve the chances that the toggle 30 will be sufficiently aligned so as to statistically reduce the likelihood (at least in comparison to the absence of such alignment), if not substantially eliminate or completely eliminate the likelihood that it will be pulled out of the artery during subsequent actions. It is noted that in some embodiments, radiopaque marker(s) may be located on the sheath 10, such as, by way of example, at the distal end/tip of the sheath 10. Such may be used, in some exemplary embodiments, to determine the position of the sheath 10. For example, a sheath marker may be utilized to determine the position/estimate the position of the distal end of the sheath relative to the puncture. Such may have utility in determining whether or not to further retract the sheath 10 from the artery based on the location of the marker. Still further by example, such may be used to determine the location of certain components of the deployment instrument 100 (e.g., the release tube 40 and/or the deployment tube 120, such as, by way of example, based on radiopaque markers thereon, etc.), relative to the sheath 10.

Figure 7:
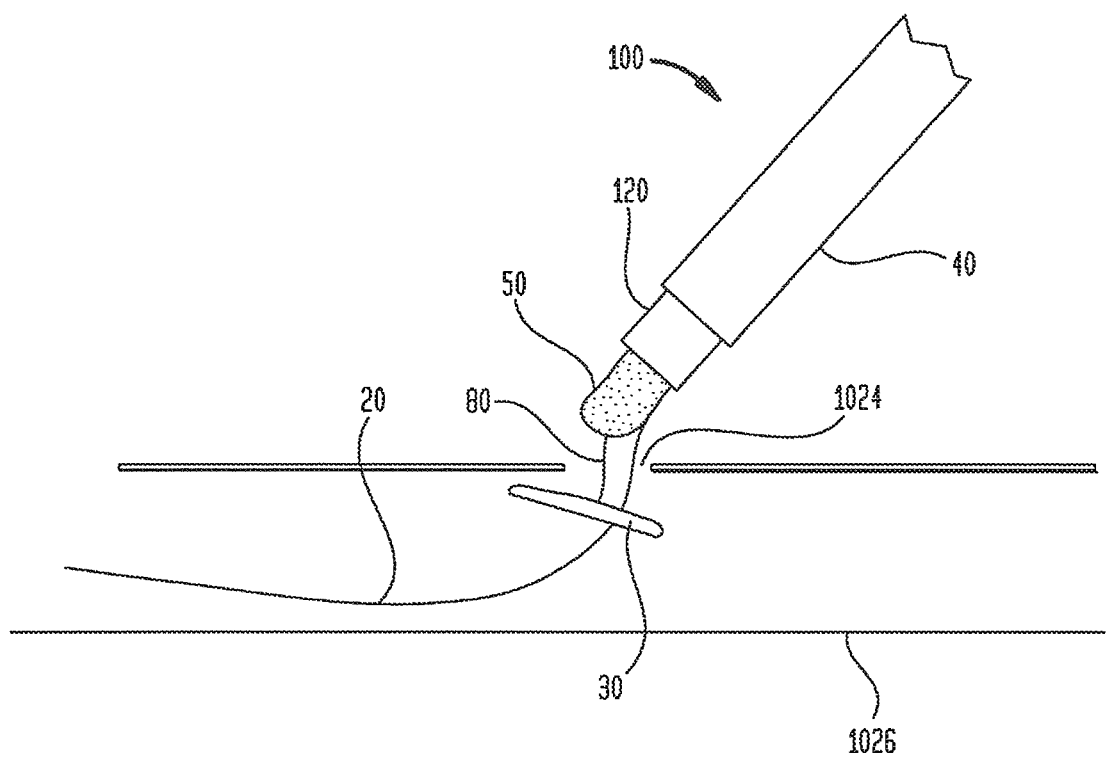
FIGS. 7 and 8A-8B are diagrams showing how the device is deployed to seal the puncture.

Next, the delivery instrument 100 is moved proximally such that the distal tip thereof is moved from the location depicted in FIG. 6 to at least about the location depicted in the functional schematic of FIG. 7 (with sheath 10 not shown for clarity). This results in plug 50 being completely withdrawn from the artery and toggle 30 being drawn closer to the puncture 1024 and/or substantially or completely against the puncture 1024. Guide wire 20 may move along with delivery instrument 100 partially and/or fully, or may remain stationary while the delivery instrument 100 is moved to the location of FIG. 7 and locations thereabouts. Continued movement of the delivery instrument 100 away from the puncture, to a location such as that depicted by way of example in FIG. 8A, pulls toggle 30 closer to the puncture and/or completely against the puncture, and also pulls plug 50 out of the delivery tube 120 and, as a result of a pulley action/synching action/lassoing action between the filament 80, the toggle 30 and the plug 50, the plug is pulled towards the toggle 30 and thus the puncture 1024 (in some embodiments such that it contacts the artery wall), with guide wire 20 having the movements or lack of movements detailed above. Below, an exemplary device that has utilitarian value in moving the plug 50 relative to the toggle 30 is described.

Next, the delivery instrument 100 is moved further away from the puncture to expose some additional components therein, such as, for example, a tamper, the lock if not already exposed, and additional filament 80 (by exposed, it is meant that the delivery tube 120 (or other component of the delivery instrument 100) is pulled past these components such that the components emerge from the distal end of the tube 120 (or other component that carries these components)). It is noted that such exposure may be achieved by pulling the handle 110 of the delivery instrument 100, which results in pulling of the delivery tube 120 (and the release tube 40), and other components.

Figure 8A:
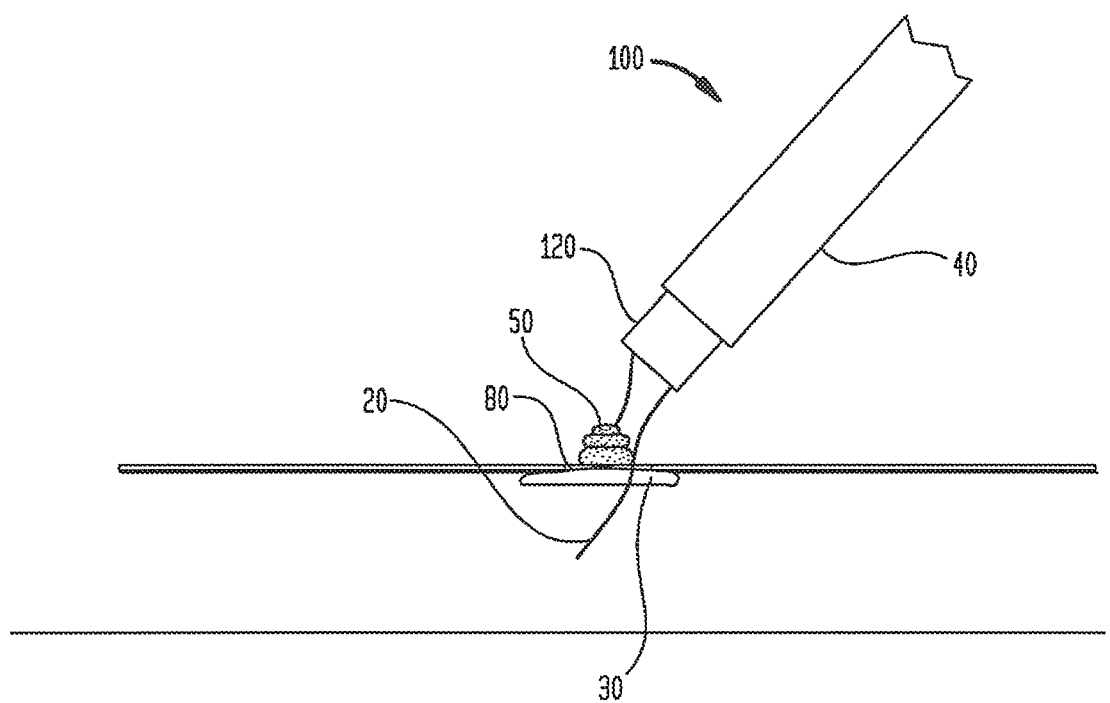
Figure 8B:
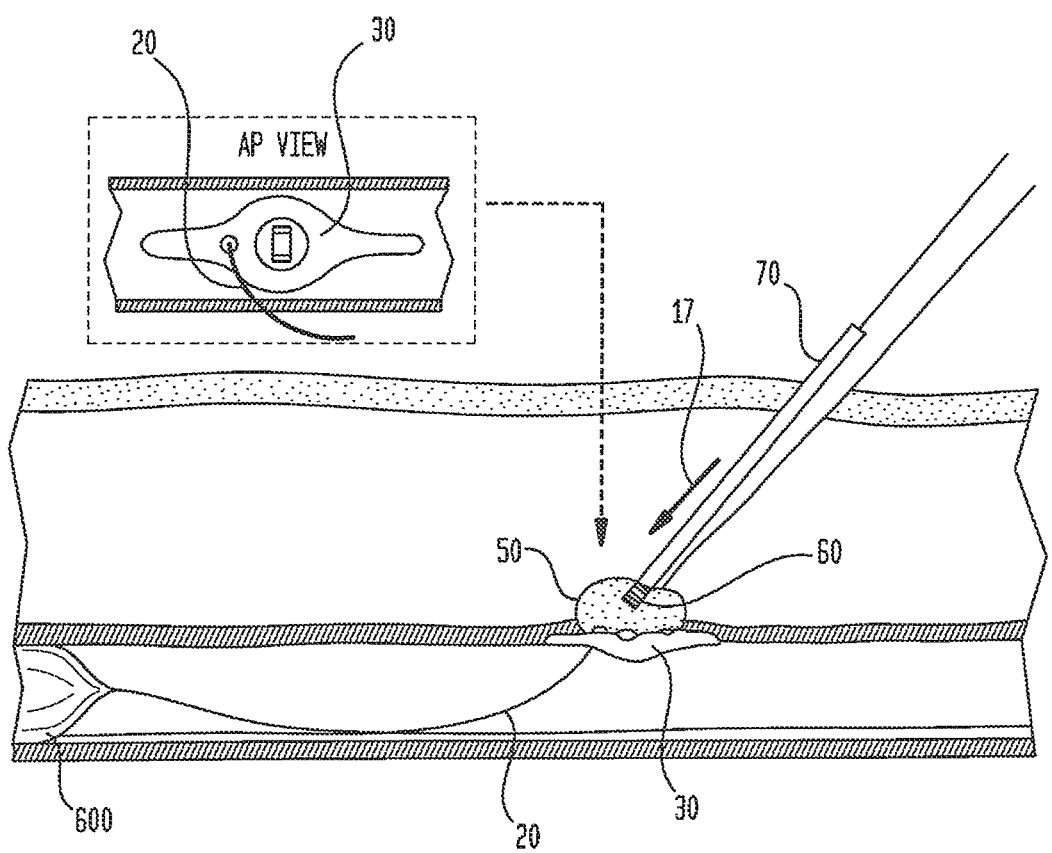

FIG. 8B depicts an exemplary result of such movement of delivery instrument 10, where tamper 70 has been exposed from the delivery tube 100 (not shown in FIG. 8B, as it is exemplary moved out of the field represented by FIG. 8B). It is noted that the procedure for exposing the tamper 70 and the tamper 70 itself may correspond to the teachings of such exposure and the tamper detailed in the '827 patent, the '681 patent and/or the '653 application, the contents of which related to such exposure and the tamper being incorporated by reference herein for use in some embodiments (although it is noted that below, an alternate tamper and an alternate method of exposure and an alternate device for achieving such exposure is detailed).

More particularly, FIG. 8A represents by way of example how the retracting the sheath 10 and deployment instrument 100 can position the toggle 30 to cover the interior of the puncture. FIG. 8B represents how further retraction of the deployment instrument 100 will deploy the contents of the delivery tube 100, namely the collagen 50, lock 60, and tamper tube 70, which will allow the user to compress the collagen 50 in place and deploy the lock 60 (in embodiments that utilize such a lock). In an exemplary embodiment, these components correspond to those disclosed in the '827 patent, the '681 patent and/or the '653 application, and variations thereof, as might be scaled for use to procedures disclosed herein. Moreover, the steps of achieving the results depicted in these FIGS. may include some and or all of the method steps disclosed in any of the '827 patent, the '681 patent and/or the '653. As noted above and is further detailed below, toggle 30 position can be confirmed fluoroscopically.

After utilitarian placement of the plug 50 relative to the toggle 30 and/or puncture 1024, the plug 50 is locked in place by tamping lock 60 with tamper 70 in the distal direction (as represented by arrow 17) as described by way of example in the '653 application. Again, an exemplary device that has utilitarian value in tamping lock 60 is described below.

It is noted that in an exemplary embodiment, some or all of the features associated with the methods of delivering the closure device 85 (including securing the closure device in place) can correspond to those variously taught in the '681 patent, the '827 patent and/or the '653 application as implemented utilizing the teachings detailed herein in general and/or the teachings applicable to the delivery instrument 100 and sheath 10 in particular, the applicable teachings of those patents and applications being incorporated by reference herein for use in some embodiments. By way of example, the teachings of the '653 application associated with pulling the plug towards the toggle prior to locking the plug in place may be used in some embodiments.

As detailed above, an exemplary embodiment utilizes a toggle that maintains an association with a guide wire. Some exemplary associations will now be described.

Figure 9A:
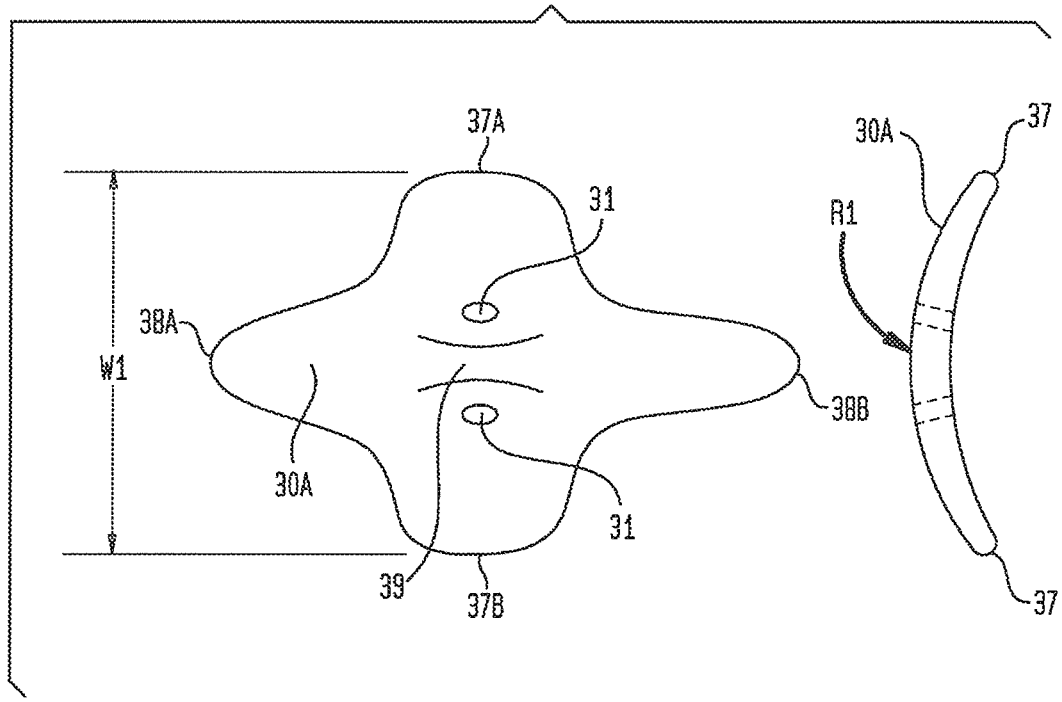
FIGS. 9A-9F depict exemplary toggle-guide wire associations.

FIG. 9A depicts an exemplary embodiment of a toggle 30A, which can be in some embodiments a large bore toggle, usable in at least some embodiments herein and methods herein. As may be seen, toggle 30A includes two holes 31 through which filament 80 may extend, as described in greater detail below. (Additional features of the structural arrangement of the toggle are also described below.) Toggle 30A may be utilized in an embodiment where there is no association between the toggle and the guide wire.

In an exemplary embodiment, toggle 30A and/or the other toggles detailed herein and/or variations thereof are configured to utilitarianly fit to a 10 mm diameter (interior) artery. The toggle 30A has a curved profile, as may be seen in FIG. 9A, which depicts both a top view and a side view of the toggle 30A. In an exemplary embodiment, the top profile of the toggle 30A has a generally circular profile having a radius of R1, which can be about 5 mm, in an unrestrained configuration, although in some embodiments, the profile may be a radius of about 4 mm, 5 mm, 6 mm, 7 mm, 8 mm, 9 mm, 10 mm, 11 mm and/or about 12 mm, or any value in between these values and/or any ranges encompassing some or all of these values (including ranges being bounded by the in between values). It is noted that in an exemplary embodiment, the aforementioned radii encompass a profile that is not exactly circular, but instead is elliptical (hence the use of the term "about", which, as used herein with respect to any teaching herein, unless otherwise noted, does not exclude exact values and the use of about also includes embodiments not so qualified (i.e., includes exact numbers, tolerance as would be understood in the art). In an exemplary embodiment, the toggle has an unrestrained width W1 of about 6 mm, although in some embodiments, the width W1 may be about 2 mm, 3, 4, 5, 6, 7, 8, 9 and/or about 10 mm, or any value in between these values and/or any ranges encompassing some or all of these values (including ranges being bounded by the in between values).

In an exemplary embodiment, the radius R1 and/or the width W1 and/or other pertinent dimensions are such that when applied to a given artery, the wing tips 37A and 37B, as opposed to the longitudinal tips 38A and 38B, which run parallel to the longitudinal axis of the artery) contact the artery wall prior to the center 39 of the toggle 30A. In an exemplary embodiment, the toggle 30A is made of elastomeric material and/or is of a material such that, when sized and dimensioned for use, allows the toggle 30A to flex (elastically and/or plastically) such that the radius R1 and/or width W1 decreases slightly (to about the interior diameter of the artery—with or without expansion of the artery (in some cases, the artery is about a zero elasticity tissue, such as may be the case for statistically very elderly patients for a population in the United States of America or Europe)) to conform to or about conform to the interior diameter, upon tensioning of the filament as detailed herein and/or variations thereof. In this regard, the upper surface may be characterized as being slightly less curved and/or slightly flatter than the interior surface of the artery (as taken on a plane normal to the longitudinal axis of the toggle and the artery, which in some embodiments, will be parallel or substantially parallel and/or effectively parallel during application).

In an exemplary embodiment, the longitudinal distance of the toggle 30A (tip 38A to tip 38B) is about 16 mm, although in some embodiments, this distance may be about 6 mm, 7, 8, 9 10, 11, 12, 13, 14, 15, 16, 17, 18, 19, 20, 21, 22, 23, 24, 25, 26 and/or about 27 mm, or any value in between these values and/or any ranges encompassing some or all of these values (including ranges being bounded by the in between values).

Figure 9B:
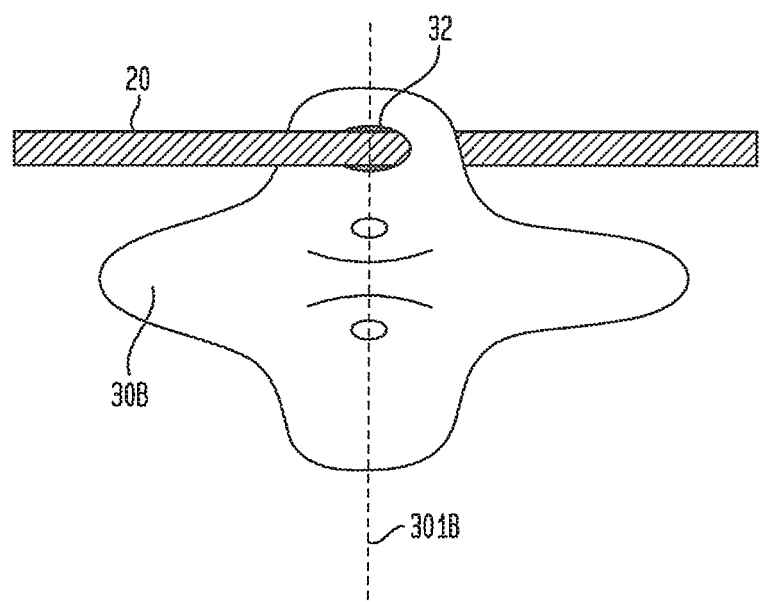

FIG. 9B depicts an alternate toggle, toggle 30B, which includes a hole 32, as may be seen, which accommodates the guide wire 20. Particularly, guide wire 20 extends through hold 32, and hole 32 permits guide wire 20 to slide or otherwise move therethrough. As may be seen, Hole 32 is located at about the lateral center of the toggle 30B (lateral center being on the lateral axis 301B, as may be seen) as well as or in the alternative, centered along the axis of the suture holes 31, which may be slightly offset from the lateral axis 301B.

Figure 9C:
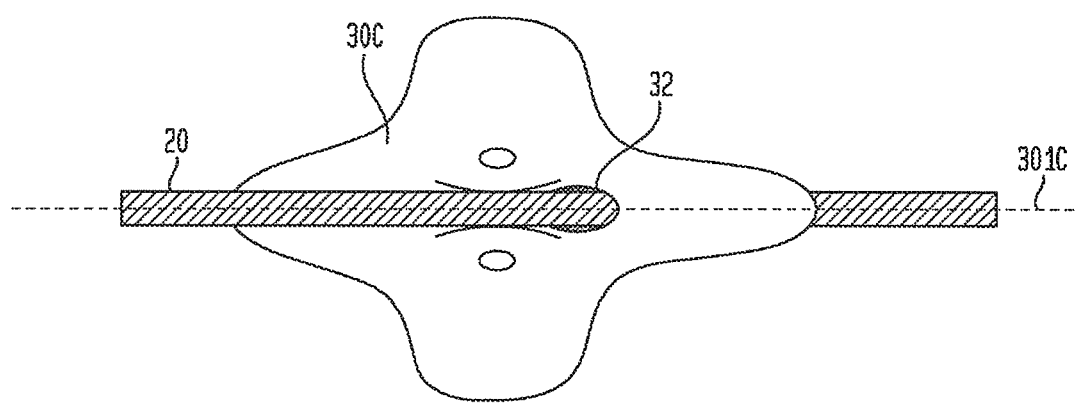
Figure 9D:
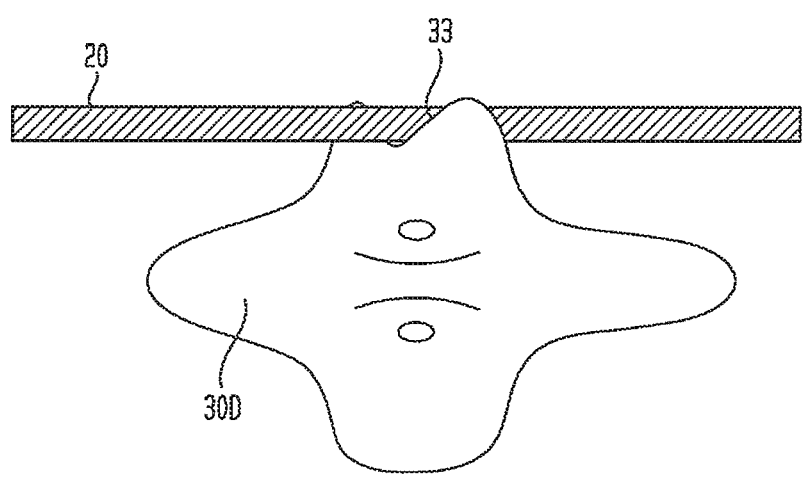

In an exemplary embodiment, the location of hole 32 is different than that depicted in FIG. 9B. For example, FIG. 9C depicts hole 32 located in the longitudinal center of the toggle 30C (longitudinal center being on the longitudinal axis 301C, as may be seen), and/or, the hole 32 is longitudinally in between the holes 31 in the toggle. Any placement of hole 32 in the toggle that will enable the teachings detailed herein and/or variations thereof to be practiced or otherwise to have utilitarian value may be implemented in some embodiments. Also, in some embodiments, association of the toggle with the guide wire is achieved not by a hole through the toggle, but via a notch on the edge of the toggle, as may be seen in FIG. 9D, where toggle 30D has a notch 33. Such an embodiment can further include one or more holes through which the guide wire extends. An exemplary embodiment that achieves association with the guide wire and the tamper?? toggle? via a notch that has a C-Shaped cross-section (or other equivalent cross-section that achieves the following functional result) such that the guide wire is "trapped" or otherwise retained therein. For example, if the C-shaped interior of the notch is such that the distance between the ends of the C is less than the maximum diameter of the guide wire 20, the guide wire should be retained therein. Alternatively, the notch exists, but the guide wire is not trapped or otherwise retained in the notch. Any device, system and or method of achieving and/or maintaining an association between the guide wire and the toggle may be practiced in some embodiments detailed herein and/or variations thereof.

Figure 9E:
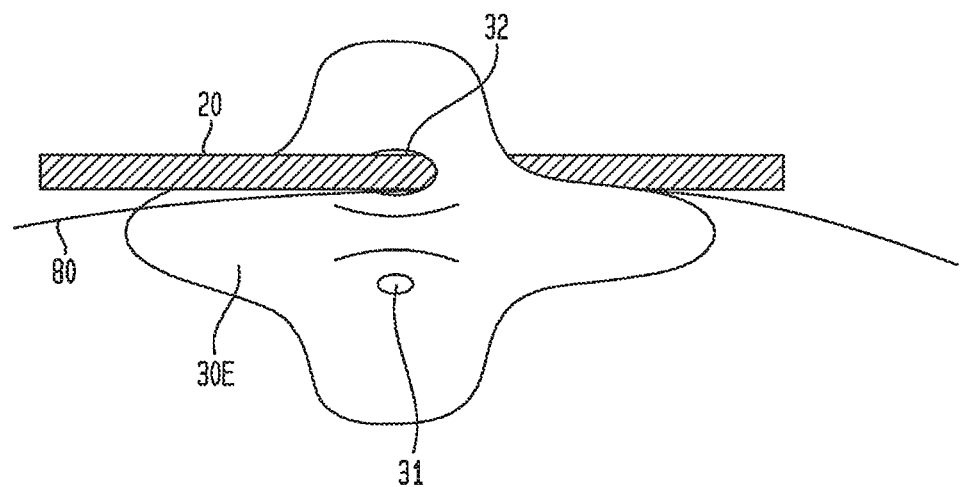

In an alternate embodiment, a suture hole may be utilized as a hole to achieve association between the toggle and the guide wire/a hole for the guide wire may be utilized to pass a filament 80 therethrough. FIG. 9E depicts such an exemplary toggle 30E. Such may be achieved by making a suture hole with a larger diameter than that which is would otherwise be the case for association with a suture alone.

Figure 9F:
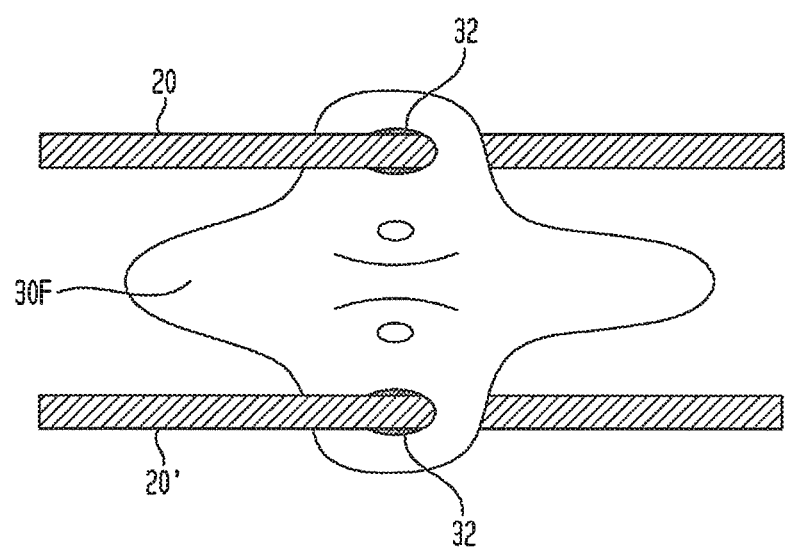

FIG. 9F depicts an alternate embodiment where two holes 32 are utilized to respectively associate two guide wires 20 with the toggle 30F. Accordingly, such an exemplary embodiment may utilize two guide wires. In some embodiments, three or more guide wires and a corresponding number or different number of association devices (e.g., holes, notches, etc.) are utilized.

Figure 10A:
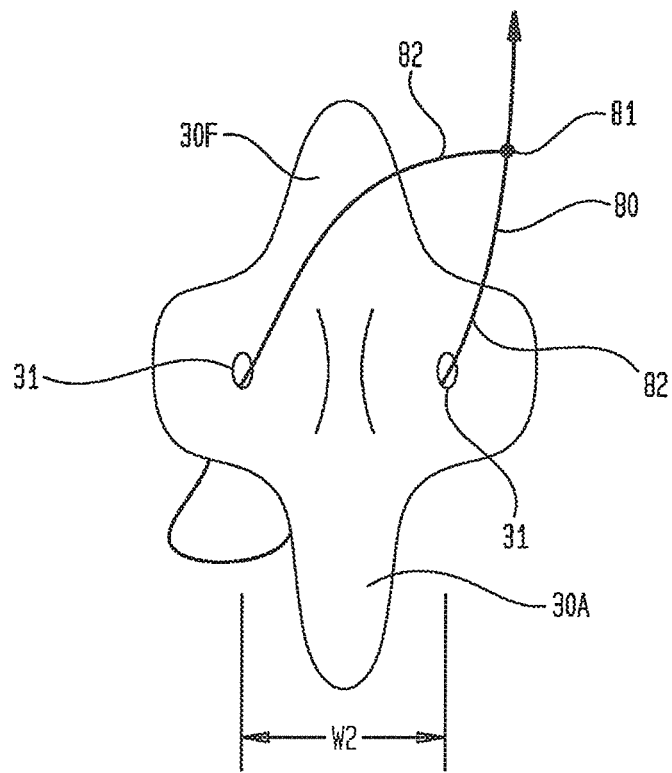
FIGS. 10A-10C depict exemplary toggle-filament associations.

FIG. 10A depicts an exemplary filament 80 weave through holes 31 of an exemplary toggle 30F, with element 81 corresponding to, for example, loop 50A and winding 52 as detailed in the '653 application, the contents of which related to the loop and winding thereof being incorporated herein by reference in an exemplary embodiment. It is noted that the exemplary embodiment of FIG. 10A includes a suture hole 31 spacing width W2 that is wider than that depicted in the exemplary toggle of FIG. 9A. In an exemplary embodiment, the holes 31 are about 4 mm from one another (W2 equals about 4 mm), although in some embodiments, W2 is about 2 mm, 2.5, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm and/or about 10 mm or any value in between these values and/or any ranges encompassing some or all of these values (including ranges being bounded by the in between values). It is noted that the spacing between the holes 31 of the toggle of FIG. 9A correspond to about 1.5 mm. In an exemplary embodiment, the hole spacing is sized so as to provide sufficient structure that provides utilitarian value with respect to providing sufficient material to react against the tension applied to the filament (e.g., it will not break the toggle during tensioning).

It is noted that the weave depicted in FIG. 10A is applicable to the toggles detailed above and/or below. In exemplary embodiment, element 81 is a collar as detailed in the '653 application. Any device system and or method of achieving the utilitarian value of element 81 (e.g., its use as a collar), which can include permitting the loop 82 established by filament 80 to reduce in diameter (like a lasso or the like) can be used in some embodiments.

Figure 10B:
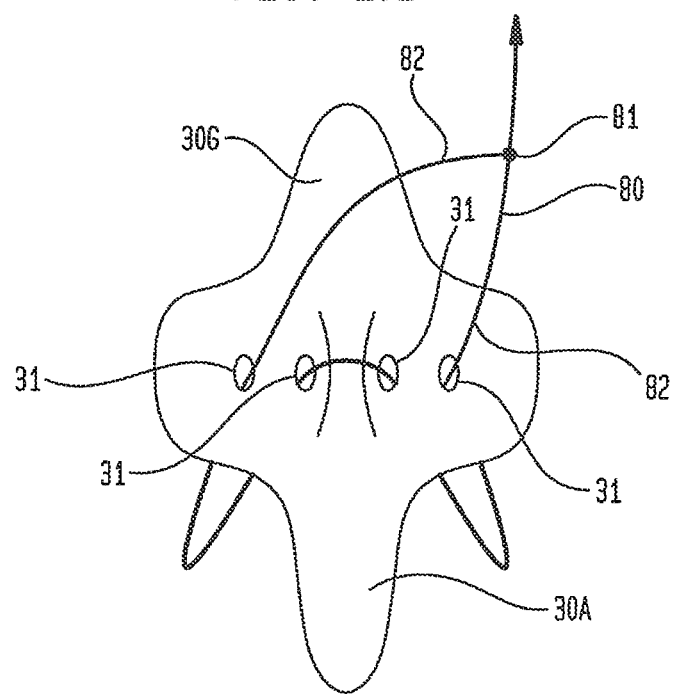

FIG. 10B depicts an alternate embodiment utilizing more than two toggle holes 31. As may be seen, four holes 31 are used, through which filament 80 is threaded. Such an exemplary embodiment can have utility by improving pulley action for compressing the plug 50 (not shown in FIGS. 10A and 10B), as compared to that resulting from the configuration of FIG. 10A and/or FIG. 9A.

Figure 10C:
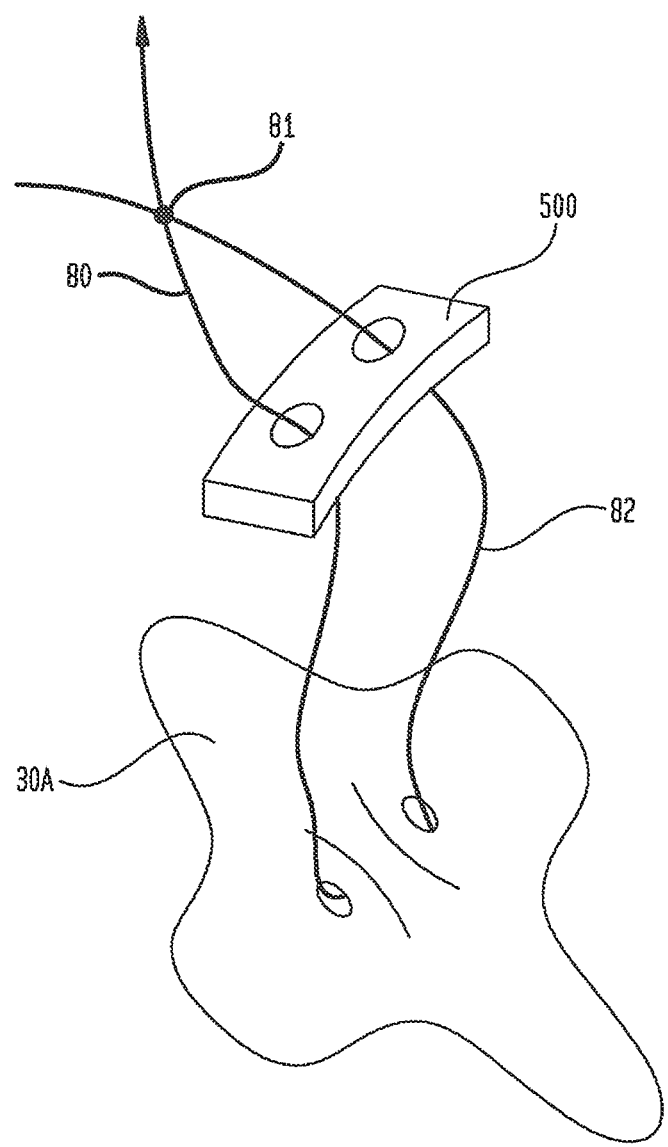

FIG. 10C depicts an alternate embodiment including a washer (resorbable and/or nonresorbable washer) 500 interposed as seen in the loop 82 formed with toggle 30A (or any other toggles described herein and/or variations thereof). Such may provide for utilitarian management of the wound/puncture at the access site. In an exemplary embodiment, washer 500, upon deployment of the closure device 85, becomes located between the vessel wall and the plug 50 (which is interposed in the loop between the toggle 30A and washer 500, but not shown in FIG. 10C), or, alternatively, proximally of the plug 50. In an exemplary embodiment, the distance between the holes of the washer 500 corresponds to the distance between the holes of the toggle 30A, although in an alternate embodiment, the holes have a different spacing than that of the toggle. (It is noted that the aforementioned hole spacings for the toggle and/or the washer are centerline to centerline dimensions.)

In an exemplary embodiment, the holes of the washer are about 4 mm from one another (W2 equals about 4 mm), although in some embodiments, the distance is about 1 mm, about 2 mm, 2.5, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm and/or about 10 mm or any value in between these values and/or any ranges encompassing some or all of these values (including ranges being bounded by the in between values). It is noted that the spacing between the holes 31 of the toggle of FIG. 9A correspond to about 1.5 mm. In an exemplary embodiment, the hole spacing is sized so as to provide sufficient structure that provides utilitarian value with respect to providing sufficient material to react against the tension applied to the filament (e.g., it will not break the toggle during tensioning).

It is noted that an exemplary embodiment includes a toggle having three holes 81 or more holes. In an exemplary embodiment, the three holes are utilized with a threaded double suture. The aforementioned toggle varieties also may have holes through which a guidewire may run.

As noted above, delivery instrument 100 includes a tamper 70 therein. While some embodiments include a tamper and are otherwise configured according to the tamper of the '827 patent, the '681 patent and/or the '653 application, an exemplary embodiment includes a tamper 71 that provides association between the tamper and the guide wire 20, as will now be described.

An exemplary embodiment of tamper 71 is depicted in FIG. 11, and includes a double-lumen. Specifically, tamper 71 includes lumen 80', through which filament 80 extends, and lumen 20', through which guide wire 20 extends. Lumen 80' is sized and dimensioned, relative to the guide wire 20 and the filament 80, to permit movement of the tamper 71 relative to the filament 80, and lumen 20', in some embodiments, is sized and dimensioned to permit movement of the tamper relative to the guide wire 20, while in other embodiments, it does not permit movement relative thereto.

Figure 11A:
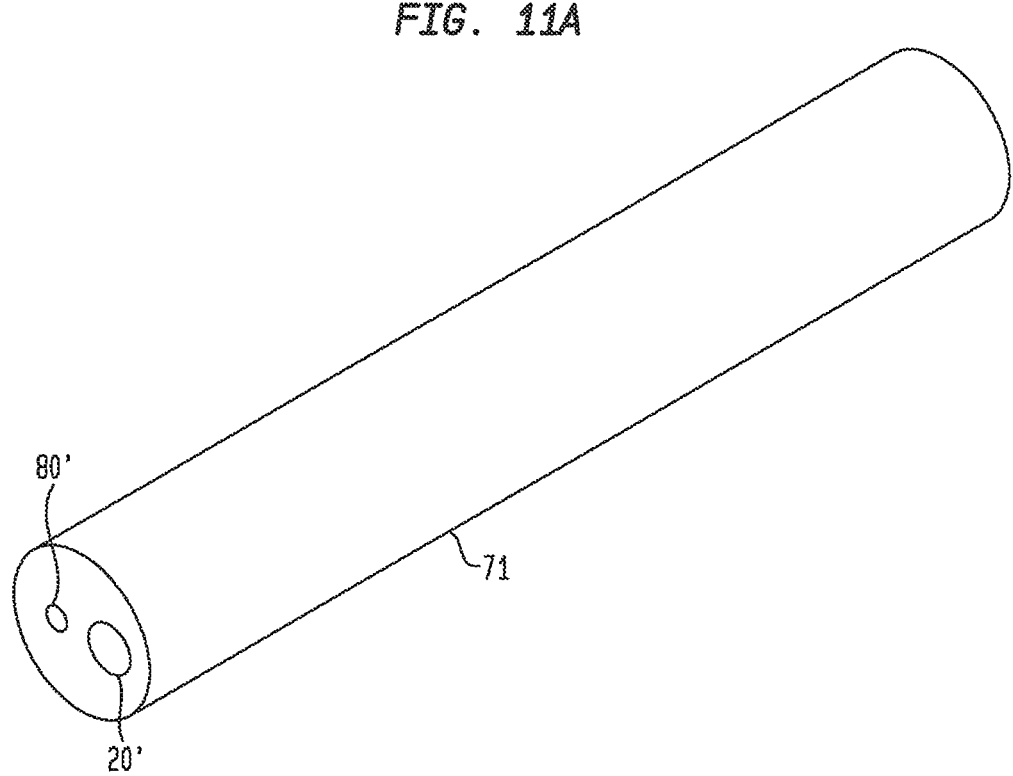
Figure 11C:
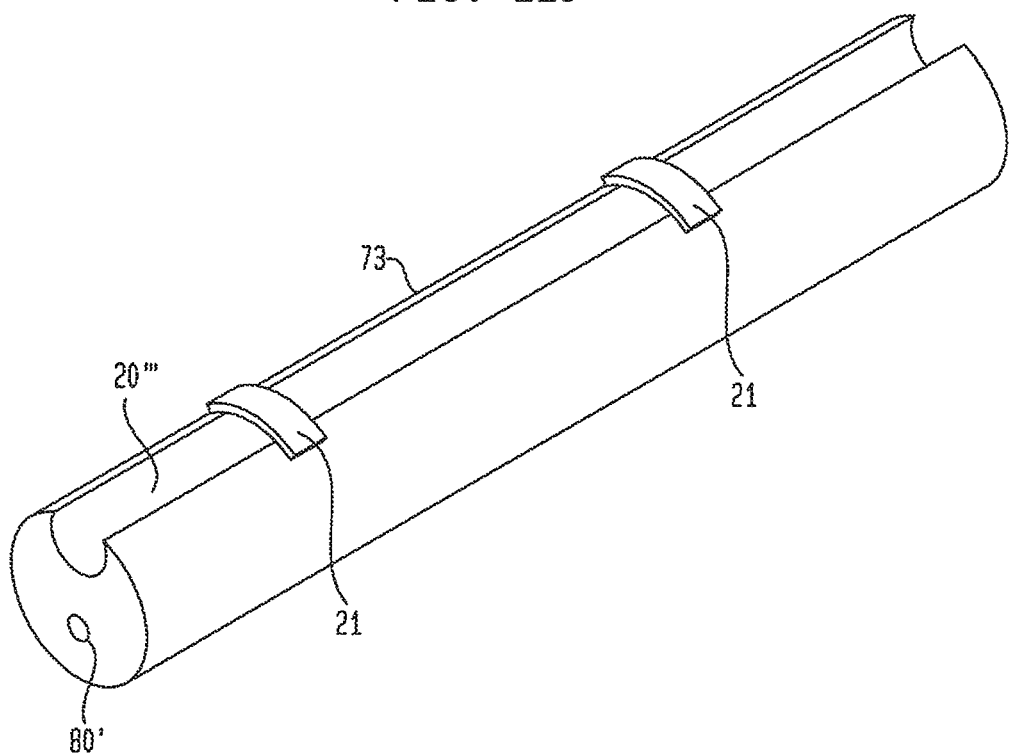

FIG. 11B depicts an alternate embodiment of a tamper, tamper 72, which achieves association with the guide wire via the use of guide wire carriers 20", through which guide wire 20 extends, the functional features of tamper 72 being the same as and/or similar to that of tamper 71. FIG. 11C depicts another alternate embodiment of a tamper, tamper 73, which includes guide wire slot 20''', through which guide wire 20 extends, and is retained therein (slidably or otherwise) via bridges 21 attached to the body of the tamper, the functional features of tamper 73 being the same as and/or similar to that of tamper 71. An exemplary embodiment that achieves association with the guide wire and the tamper does not include the bridges 21, while including the slot. The slot may have a C-shaped cross-section (or other equivalent cross-section that achieves the following functional result) such that the guide wire is "trapped" or otherwise retained therein even in the absence of the bridges 21. For example, if the C-shaped interior of the slot is such that the distance between the ends of the C is less than the maximum diameter of the guide wire 20, the guide wire should be retained therein. Alternatively, the slot exists, but the guide wire is not trapped or otherwise retained in the slot. Any device, system and or method of achieving and/or maintaining an association between the guide wire and the tamper may be practiced in some embodiments detailed herein and/or variations thereof. It is noted that the embodiment of FIG. 11A can have utility in that it provides a level of safeguard against a user inadvertently gripping the guide wire or the like during tamping, where in an exemplary embodiment, the tamper slides relative to the guidewire during tamping.

FIG. 12 functionally depicts the environment in which tamper 71 is utilized. More particularly, after the delivery instrument 100 is withdrawn as detailed above to expose the tamper and the other components, tamper 71 is exposed as depicted in FIG. 12A. In the exemplary embodiment depicted in FIG. 12, guide wire 20 and filament 80 extend through respective lumens 20' and 80'. (FIG. 12B depicts a cross-section of tamper 71 taken at line A-A—of FIG. 12B, where the guide wire 12 and the filament 80 have been removed for clarity.)

In an exemplary embodiment, the tamper 71 (or 72 or 73 or variations thereof) enables tamping action over/along the guide wire 20 and suture 80, running through separate lumens 20' and 80' in the double lumen tamper, until the tamper 71 contacts the lock 60. Upon contact, the user pushes down (continues to push down) on the lock 60 to compress the plug 50 in place/to lock the already compressed plug 50 in place (such as is done by way of example and not by way of limitation, as detailed in the '827 patent, the '681 patent, the '653 application, at least with respect to movement along the filament thereof), without affecting the placement of the guide wire 20. The double lumen tamper 71 enables utilitarian support of the guide wire 20, as compared to the absence of the lumen for the guide wire (or the absence of the alternate components to achieve association with the guide wire) during the deployment of the device and and/or can statistically improve user experience when tamping as compared to tamping without such an association feature.

Figure 13:
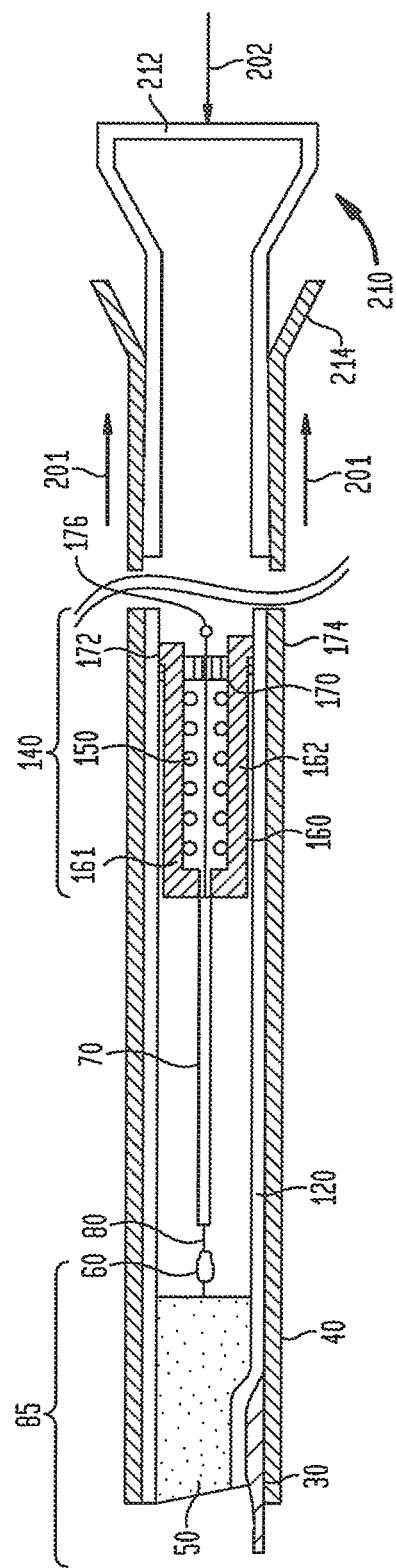
FIG. 13 depicts an alternate embodiment of a deployment instrument.

FIG. 13 functionally depicts an alternate embodiment of a delivery instrument 200. It is noted that some and/or all of the additional features (e.g., the tensioner apparatus, described below) described with respect to instrument 200 may be included in instrument 100. It is further noted that an exemplary embodiment of deployment instrument 200 includes some or all of the features of instrument 100 detailed above.

Briefly, movement of the release tube 40 relative to the delivery tube 120 is achieved by applying force to section 214 of the release tube 40 in the proximal direction of the deployment instrument 100 (200??), as indicated by arrow 201, while applying a reaction force to the delivery tube 120 at section 212 in the direction of arrow 202. Application of sufficient force thereto drives the release tube 40 towards the proximal end of the instrument 200, and moves it relative to the deployment tube 120, until section 214 abuts section 212 or until the force is reduced/eliminated. In this regard, the exemplary embodiment of FIG. 13 is such that there is a slight friction fit between the tubes 40 and 120, although in an alternate exemplary embodiment, the fit is a slip fit. Alternatively or in addition to this, additional components, such as an O ring or the like, may be interposed between the tubes to generate a modicum of friction. Any device system and/or method of moving the tubes relative to one another may be practiced in some embodiments.

In an exemplary embodiment, aside from the different mechanisms utilized to move the tubes relative to one another, the functionality of the deployment instrument 200 corresponds to that of the deployment instrument 100, as well as its use.

An exemplary embodiment includes a device, system and/or method of gauging or controlling the application of tension on filament 80 while deploying the closure device 85 described herein. Specifically, the application of high tension on filament 80 may result in the toggle pulling out. Alternatively, insufficient tension will not compress the plug 50 onto the exterior vessel wall.

Prior to describing an exemplary embodiment of a tensioner assembly of the delivery instrument 100, some actions associated with deployment of the closure device 85 by the deployment instrument 100 will be briefly described (some of which includes redescription and/or variations of the description above) in the context of the function of the tensioner assembly.

As detailed above, movement of the deployment instrument 100 in the proximal direction causes toggle 30 to engage the artery wall. As the toggle 30 catches/engages, resistance will be felt by the user with increased movement of the deployment instrument 100 in the proximal direction.

With increased movement of the deployment instrument 100 away from the puncture, the plug 50 is deployed into the puncture tract with the toggle 30 engaging or catching the inner surface of the artery wall contiguous with the puncture. The instrument 100 is then pulled further outward. Inasmuch as the toggle 30 trapped against the interior of the artery wall, the continued retraction of the deployment instrument 100 causes the filament 80 to pull the plug 50 out of the delivery tube 120 of the deployment instrument 100 and into the puncture tract. As the deployment instrument comes out of and/or is moved further away from the puncture tract, continuous steady resistance will be felt as the tensioner assembly of the deployment instrument controls the force on the filament 80 during the retraction procedure.

Continued retraction of the instrument 100 brings the tamper 70 out of the distal end of the deployment instrument 100 (thus exposing the tamper 70).

The retraction of the deployment instrument 100 carries the plug 50 into engagement with the exterior of the artery wall immediately adjacent the puncture. Continued retraction causes the filament 80 to deform the plug 50, i.e., cause it to deform radially outward, in an exemplary embodiment, as detailed by way of example in the '827 patent, the '681 patent and/or the '653 application, the contents of which relating to such deployment/expansion/positioning of the plug incorporated by reference herein for use in embodiments associated with deployment of the closure device 85. In an embodiment, the plug 50 (which may be a collagen pad, as noted above) is forced to fold down after exiting the delivery tube 120 (in some embodiments, it begins to fold down immediately upon exiting the delivery tube 120). The existence of blood within the puncture tract can further contribute to the deformation of the plug 50, because, in some embodiments, it is collagen foam that expands and softens in the presence of blood. The retraction procedure continues to pull the deployment instrument 100 up the filament 80 until the user stops pulling. At this point the plug 50 should be located in the puncture tract contiguous with the opening in the artery, and the lock 60 (if utilized) located immediately proximally of the plug.

The plug 50 is now ready to be positioned in the tract. To achieve that end, the user compacts the plug 50 by gently tensioning the filament by, for example, pulling on the handle 110 of the delivery instrument 100 in the proximal direction with one hand. This moves loop element 81 down along the filament as a result of tension on filament. Here, toggle 30 acts in an analogous manner to a pulley as described in, for example, the '653 application, the contents of which associated with that pulley action being incorporated herein by reference for use in an exemplary embodiment utilizing such pulley action. This has the effect of tightening the loop 82. As element 81 moves down filament section to tighten loop 81, it compacts plug 50. This forces plug 50 to conform to the artery contiguous with the puncture in the artery.

Next, the tamper 71 is manually slid down the filament 80 by the user's other hand so that it enters the puncture tract and engages the proximal side of the lock 60, if present. A force is applied to tamper 71 sufficient to overcome the resistance to movement of the lock 71 relative to the filament, at least if the lock 60 corresponds to the lock of the '653 application. This causes the lock 60 to slide down filament section until it abuts element 81. An exemplary embodiment of the lock 60 is configured, when used in conjunction with filament 80, to provide a certain amount of resistance to movement along filament 80. This locks element 81 in place, as, for example, taught in the '653 application, thus preventing loop 82 from expanding. This feature causes the plug 50 to be secured in the compact position until hemostasis occurs (which happens relatively very quickly, thereby locking the closure device in place). That is, because the plug 50 is compressed between the toggle 30 and the lock 60, plug 50 is retained or locked in position within the puncture tract and cannot move away from the toggle, even before the blood clots in the plug.

In an exemplary instrument the deployment instruments detailed herein and/or variations thereof include a tensioner assembly. Such a tensioner assembly will be described in terms of deployment instrument 200, but are readily applicable to deployment instrument 100, as will now be described.

FIG. 13 depicts a cross-sectional view of deployment instrument 200, including tensioner assembly 140 in the form of a tensioner cartridge 160. Tensioner cartridge 160 configured to gauge/measure and/or to control the forces (e.g., tension in filament 80) resulting from deployment of closure device 85. The tensioner cartridge 160 provides the user with visual and/or tactile and/or auditory feedback during deployment. The construction of the tensioning cartridge includes a spring 150 located inside a retractable tube 162 that allows for the passage of filament 80 therethrough. The cartridge 160 includes a retractable member 170. In an exemplary embodiment, the retractable member 170 is fixedly attached to the filament 80, such that tension on the filament 80 imparts a force onto the retractable member 170, and thus spring 150. In an alternate embodiment, the filament 80 is attached to one or more of the coils of spring 150 (e.g., the most proximal coil/last coil), such that tension on the filament 80 imparts a force onto the spring 150. In an alternate embodiment, the retractable member 170 may include a soft tensioning member 172 through which the filament 80 extends. The tensioner assembly 140 one or more utilitarian functions. For example, it controls the force applied to the filament 80 (and thus the tension) by holding the filament taut during pull back of the instrument 200 (or 100) while providing a system for allowing the user to guard against the application of too much force. By utilizing the tensioner assembly 140 as detailed below, a user may apply adequate filament tension for compressing the plug 50 and/or during tamping the lock 60 or other component.

The tensioner assembly may also provide tactile and/or visual and/or auditory indication for the user to stop pulling back and/or to stop applying additional (increasing) force to the deployment instrument in the distal direction when the end of suture length has been reached through change in color, shape, etc., visible on the instrument. In an exemplary embodiment, this can prevent or otherwise enable safeguarding against excessive force being applied to the toggle, preventing the toggle from pulling out of the blood vessel.

During use, application of a force onto deployment instrument 100 that results in a first tension on the filament is sufficient to withdraw the cartridge 160 out of the delivery tube 120, exposing the cartridge 160 such that the user may handle the cartridge 160 with his or her hand. In particular, cartridge 160 is carried within delivery tube 120 such that there is a slight friction fit between the two components. This may be achieved, by way of example, via, elastomeric O-ring 174, as may be seen. Application of the first tension (by applying a sufficient withdrawal force on the instrument 200 in the proximal direction) is sufficient to overcome the friction forces and pull the cartridge 160 out of the tube 120. Alternatively or in addition to this, a snap fit is utilized to retain the cartridge, and a sufficient force applied to the instrument resulting in sufficient tension on the filament is sufficient to release the snap fit. In yet another alternative embodiment, a positive retention mechanism, such as an actuating cylinder or box beam, etc., that extends into the tube 120, and thus blocks the cartridge 160 until it is moved out of the tube 120, or at least from in front of the cartridge 160, may be utilized to retain and then release the cartridge. Any device, system and/or method that can provide the modicum of friction between the cartridge 160 and the delivery tube 120 and/or that provides the modicum of securement so as to releasably retain the cartridge 160 in the delivery tube 120 until it should be exposed can be utilized in some embodiments. In this regard, it is noted that the first tension may vary between embodiments. By way of example, the tension associated with overcoming the friction fit utilizing, for example, the O-ring, may be different from that associated with overcoming the snap-fit. Moreover, the tension may be variable or generally constant. For example, the tension during withdrawal of the cartridge 160 from the delivery tube 120 will be generally constant during the withdrawal process with respect to the friction fit utilizing the O-ring, whereas the tension may vary during withdrawal with respect to the snap-fit or the like. Embodiments where the tension is relatively constant, or at least moderately increases within a range that does not result in damage to the artery wall and/or dislodgement of the toggle, can have utility in that this results in a tension that generally maintains the toggle in place against the puncture on the interior of the artery.

Figure 14:
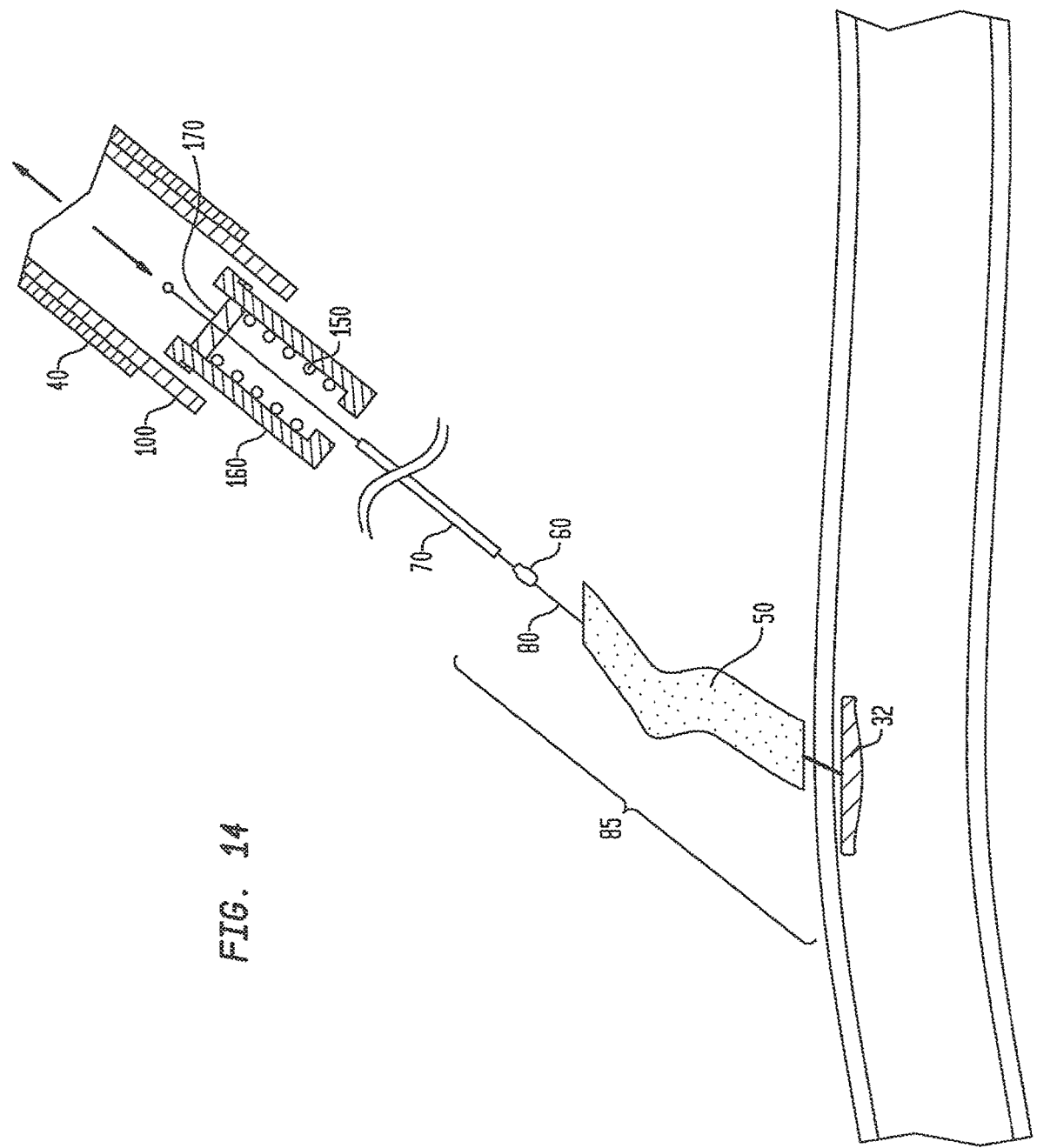
FIG. 14 depicts use of the embodiment of FIG. 13.

With respect to the embodiment of FIG. 13, where the O-ring results in a friction fit between the tube 120 and the cartridge 160, application of the first tension results in the ejectment/exposure of the cartridge 160. This is schematically represented by way of example in FIG. 14. Upon sufficient exposure of the cartridge 160, the user grips the cartridge 160 with a free hand and gradually or abruptly begins to apply force to the cartridge in the proximal direction at a level that is in equilibrium, in an exemplary embodiment, to that applied to the instrument 200, until the cartridge 160 is completely free of the delivery tube 120, at which point the tension in the filament 80 is a result of force applied to the cartridge 160 in the proximal direction.

Figure 15:
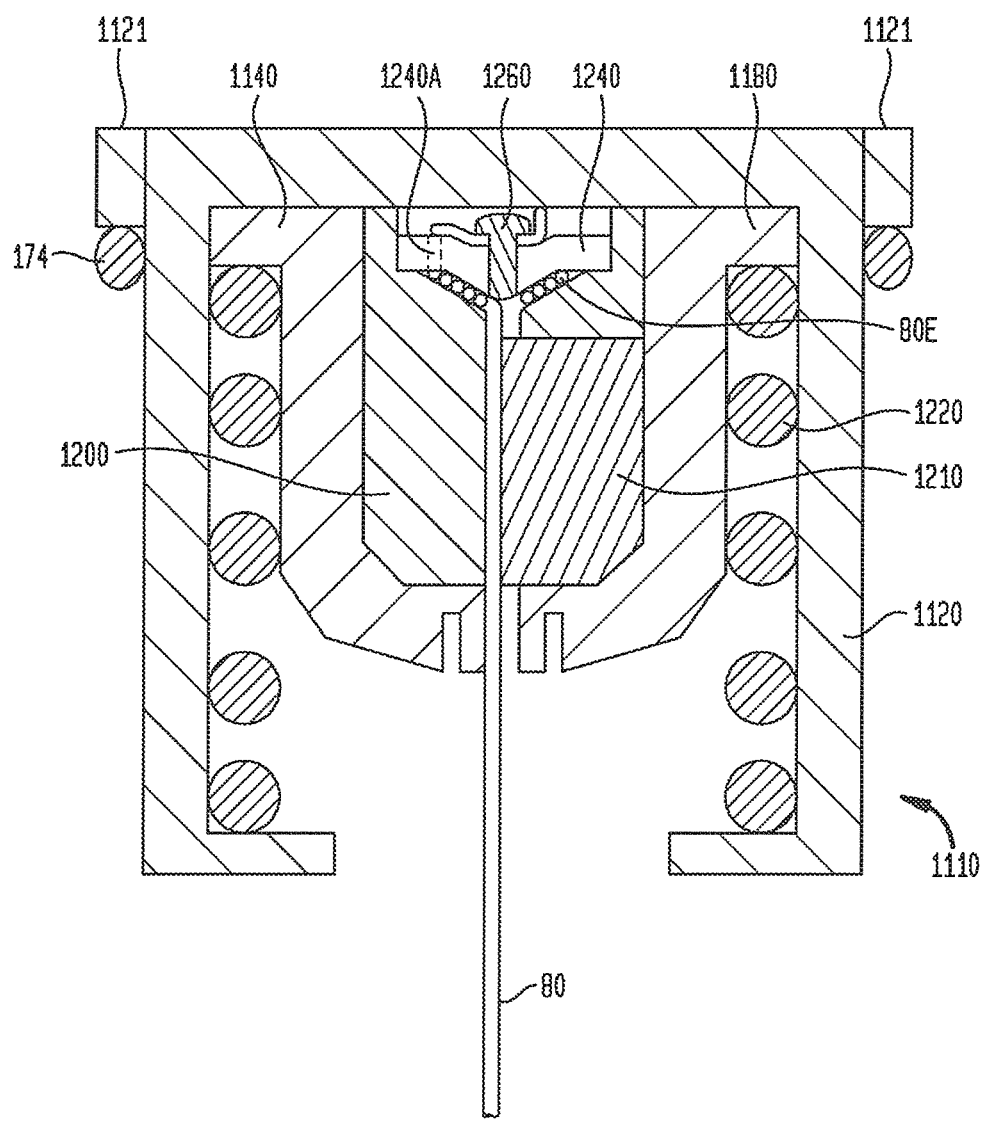
FIGS. 15-18 depict features of an exemplary tensioner according to an embodiment.

An exemplary embodiment of the present invention includes a deployment instrument 100 including an exemplary tensioner assembly 1110 as may be seen conceptually in FIG. 15. In an exemplary embodiment, the tensioner assembly 1110 conceptually corresponds to the cartridge 160 detailed above, although as will be detailed below, in an exemplary embodiment of the cartridge 160, there are different features between the two.

A portion of the procedure involving deployment of the closure device 80 in a recipient using the exemplary tensioner assembly 1110 of FIG. 15 will now be described. As may be seen in FIGS. 15 and 16, the tensioner assembly 1110 includes a frame 1120 in which a hub assembly 1140 is slidably retained. Frame 1120 includes protrusions 1121 that interact with O-ring 174. In this regard, frame 1120 corresponds to element 161 of FIG. 13. The frame 1120 serves as a handle that the user may grasp during application of the closure device 85 to the recipient. In some embodiments, the handle is provided with knurling or tread grips or the like to facilitate grasping by the user. The hub assembly 1140 includes a hub 1180 and a tensioner insert 1200 (and silicone tension block 1210, which provides constant friction to the filament as it uncoils). The hub assembly is spring loaded by spring 1220 (which corresponds to spring 150 of the device of FIG. 13) in the proximal direction of the deployment instrument 200. That is, with respect to FIG. 15, the spring 1220 forces the hub assembly 1140 upward, relative to the frame 1120. Another way of describing this is that the spring 1220 forces the frame 1120 downward, relative to the hub assembly 1140.

It is noted that alternate embodiments include structure that is different from that detailed herein. Indeed, a visual comparison between the embodiment of FIG. 13 and that of FIG. 15 reveals that there are differences. It is thus again noted that the structure detailed herein is exemplary and conceptual, and can and/or will vary in implementation. In this regard, while the embodiment of FIG. 15 depicts a hub 1140 that extends into the interior of spring 1220, the embodiment of FIG. 13. Hub 1140 corresponds to retractable member 170 of FIG. 13. However, retractable member 170 does not so extend into the spring 150, as may be seen.

In an exemplary embodiment, the spring 1220 permits the tension on filament 80 to be controlled/ensures that sufficient tensioning and not too much tensioning is applied to the filament during deployment of the closure device 85, as will now be detailed.

Referring to FIG. 15, the tensioner assembly 1110 includes a filament recess between the tensioner insert 1200 and a filament cap 1240 in which filament 85 is wound in a coil section 80E, from which the filament 80 travels to the closure device 85. The end of the filament 80E is threaded through a hole 1240A in the filament cap 1240 and is trapped between the filament cap 1240 and a filament lock 1260 to hold the end of the filament 80 in place. Filament lock 1260 may be held to filament cap 1240 via a screw fit or a snap fit or through the use of an adhesive or a weld, etc. That said, in an alternate embodiment, the filament 80 extends completely from one side of the hub 1140 (or the retractable member 170) to the other side thereof, and further proximally out of the frame 1120 (or element 161).

As may be seen in FIG. 15, a friction block 1210 is located in a cut-out section of the tensioner insert 1200. In an exemplary embodiment, the friction block 1210 is a silicon block that is dimensioned such that when inserted in the hub 1180 along with tensioner insert 1200, a compressive force on filament 80 is applied by the friction block 1210 and the hub 1140. In some exemplary embodiments, as will be described in greater detail below, as the filament 80 (filament from section 80E) is drawn from the spool of the tensioner assembly 1110, the user feels a relatively constant resistance and/or a relatively consistent resistance as compared to other deployment instruments 100 (i.e., the resistance felt with one deployment instrument 100 used during a given procedure will be about the same as that felt during a prior procedure with another deployment instrument 100). That is, the friction block 1210 in combination with the tensioner insert 1200 and hub 1140 function to control the force required to at least initially withdraw the filament 80 from the spool.

In an exemplary embodiment, friction block 1210 corresponds to soft tensioning member 172 detailed above with respect to FIG. 13. As has been noted above, the specific structure of various embodiments can vary, while utilizing the principles detailed herein.

Figure 16:
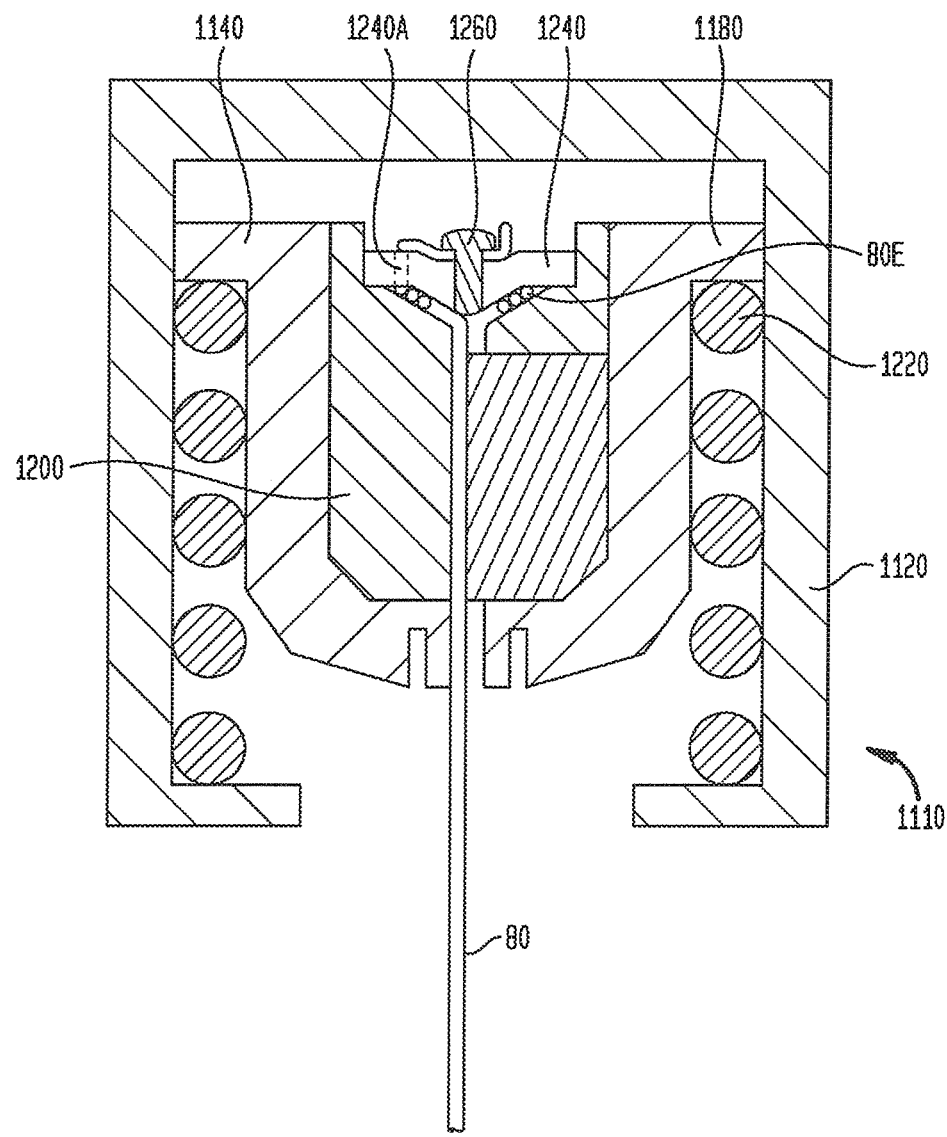
Figure 17:
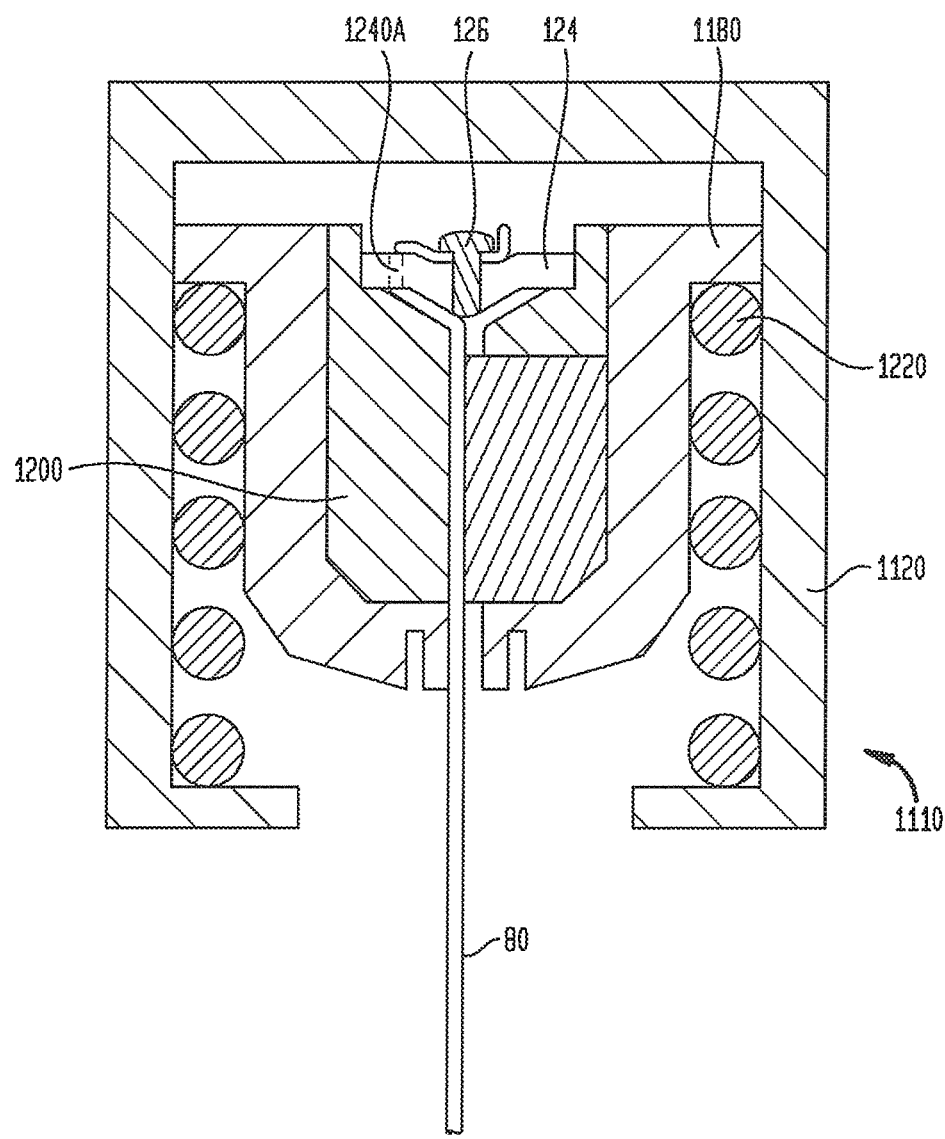

As noted above, a force applied to deployment instrument 200 sufficient to result in a first tension in the filament can result in the cartridge 160 (or tensioner assembly 1110) being exposed (withdrawn/released from inside delivery tube 120). As noted above, inasmuch as the toggle 30 is trapped (anchored) against the interior of the artery wall, the continued retraction of the deployment instrument 200 causes the filament 80 to pull the plug 50 out of the deployment tube 120 of the deployment instrument 200. Also, once the toggle 30 catches on the wall of the artery, the filament 80 (filament from section 80E or other location where the filament is stored) will be drawn from the spool of the tensioner assembly 1110. Some resistance will be felt, at least in embodiments utilizing the friction block 1210 (or its corresponding structure 172) described above (as opposed to other embodiments where no drag force is applied to the filament as a result of compression of the filament by the friction block, such as in the case where no friction block 1210/structure 172 is used and a bore or other space of the tension insert 1200 through which the filament 80 passes is oversized relative to the filament 80). This resistance may require the user to apply about ¾ths of a pound of force to the deployment instrument 200 to pull the filament 80 out of/through hub 1180/structure 170. The user continues to pull the deployment instrument 200 away from the recipient with a force sufficient to overcome the friction resulting from the compressive force applied to the filament 80 by the friction block 1210. At a given distance of the deployment instrument 200 from the recipient/from the puncture, the filament 80 will be completely unwound from the spool (or otherwise withdrawn through structure 172 until stop 176 strikes structure 172 in the case of cartridge 160). FIG. 16 depicts the tensioner assembly 1110 in the state where the filament 80 is about ½ way unwound from the spool and FIG. 17 depicts the tensioner assembly 1110 in the state where all of the filament 80 has been unwound from the spool. The tension on filament 80 is high enough to unwind the filament from the spool, and potentially compresses spring 1220 by a corresponding amount.

At this point, with increasing force applied to the deployment instrument 200, the tension in filament 80 reaches a high enough value (the first amount detailed above) to overcome the friction forces between the O-ring and delivery tube 120, and thus the cartridge 160 (or tensioner assembly 1110) becomes exposed (withdrawn/released from inside delivery tube 120).

At this point, the user grips the cartridge 160 or frame 1120, and continues to withdraw the cartridge 160 or frame 1120 away from the recipient with a steady or increasing force. When the tensioner assembly 140 1110 is located a first linear distance from the vessel wall, because the end of the filament 80 (or other part of the filament 80) is trapped between filament cap 1240 and the filament lock 1260 (or element 176 abuts structure 172), continued pulling of the tensioner assembly away from the recipient (past the first distance), when the user holds the frame 1120 (or element 162) causes the filament 80 to become more tensioned because the "unwinding" of the filament 80 from the spool has stopped (there is no more filament from section 80E to be unwound) and the end of the filament 80 is held in place as it is attached to the tensioner assembly. Accordingly, this increase in tension as the user moves the deployment tensioner assembly from the first distance from the vessel wall causes frame 1120 (or element 162) to move relative to hub assembly 1140 and thus causes spring 1220 (or spring 150) to compress or further compress. The force compressing the spring is substantially equal to the tension in the filament 80. As the tension of the filament 80 progressively increases as the user continues to pull the tensioner assembly 200 away from the recipient (via pulling on the frame 1120 or element 162), the spring 1220 continues to be compressed, thus resulting in a gradual increase in the tension of the filament 80 as the tensioner assembly is continued to be pulled away from the recipient. This as compared to the relatively sudden increase in tension that would exist if the hub assembly 1140 were instead rigidly fixed to the tensioner assembly 1110 and/or the spring 1220 were not present (or if structure 170 were instead rigidly fixed to the tensioner assembly 140 and/or the spring 150 were not present. In this regard, the spring 1220/spring 150 provides a dampening or cushioning effect with respect to the force applied to the inner wall of the blood vessel or other body passageway which reacts against the toggle 30 at the time that the filament 80 is fully unwound from the spool. Thus, there should be no sudden increase in the force/pressure on the wall at the location of the toggle 30. Instead, there should be a gradual increase in the force/pressure on the wall at the location of the toggle 30. In an exemplary embodiment, the hub assembly 1140 may travel about eight (8) millimeters upon the application of about two (2) pounds of tension force in the filament 80 before bottoming out (i.e., the hub assembly 1140 cannot move further downward/frame 1120 cannot move further to the upward with respect to FIG. 15). Thus, an embodiment provides a mechanically induced increasing tension force applied to the filament that increases with increasing distance of the tensioner assembly away from the puncture at a rate of less than about 1.5 pounds per 4 mm of increased distance of the deployment instrument away from the puncture. Accordingly, in an exemplary embodiment, pulling the tensioner assembly away from the puncture while the filament is connected thereto results in an initial contact of the anchor to the wall of the body passageway followed by a gradual increase in pressure applied to the wall by the anchor while tension in the filament is less than about two (2) pounds. Thus, via a mechanical device of the deployment instrument 200, a sudden increase in pressure applied to the wall of a body passageway by the toggle 30 is avoided.

Figure 18:
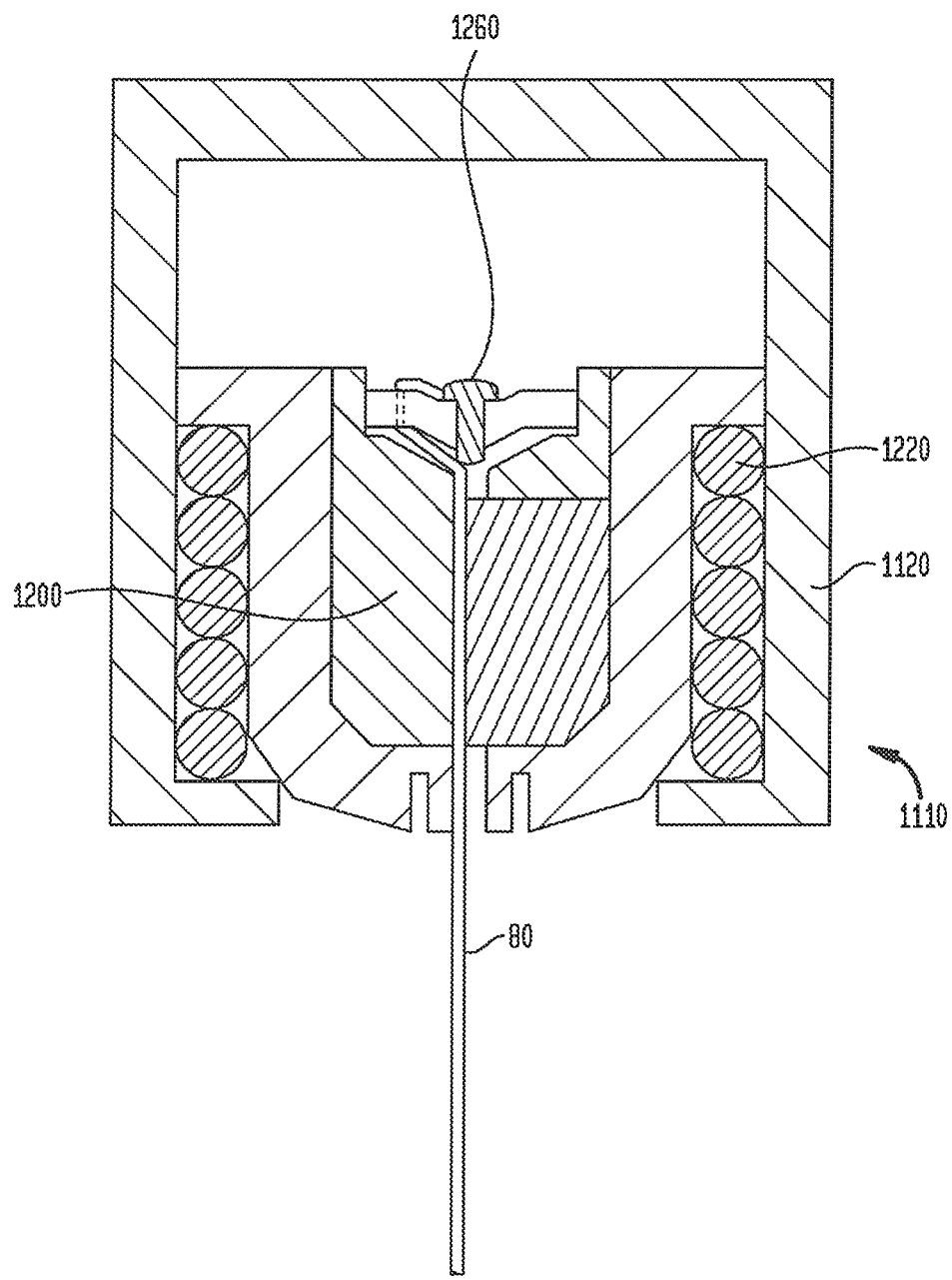

FIG. 18 depicts spring 1120 fully compressed upon the application of two (2) pounds of tension force in the filament 80 by the user while filament 80 is connected to toggle 30 (which, as noted above, is lodged in the artery). By bottoming out the hub assembly 1140, and not pulling on the tensioner assembly too much more after that, the user can ensure that he or she has applied about two (2) pounds of tension force on the filament 80, and not too much more. This ensures that sufficient tension has been applied to the filament to properly deploy the closure device 85, and not too much more. Also, the spring 1220/spring 150 at least partially reduces what otherwise might be a spike in the force applied to the wall of the artery upon the filament 80 becoming completely unwound from the spool and becoming unslackened due to movement of the tensioner assembly away from the recipient.

In an exemplary embodiment, the user feels/senses the gradual increase in tension as the spring 1220/spring 150 is compressed (as compared to the relatively static tension resulting from friction block 1210/element 174), and thus is provided an indication that the tensioner assembly will soon reach the mechanical limits of its withdrawal away from the recipient, after which any further withdrawal will be due to the plastic and/or elastic nature of the filament and the recipient. In some embodiments, the spring 1220 is a linearly compressible spring, and thus the gradual increase in tension as the spring 1220 is compressed is linear. Non-linear compressible springs may also be used, in which case the gradual progressive increase in tension is not linear. In an exemplary scenario of use, the user continues pulling the tensioner assembly away from the recipient until the spring 1220/spring 150 bottoms out, and then halts further movement of the tensioner assembly away from the recipient. Alternatively, the user can continue to pull the tensioner assembly away from the recipient, thereby further increasing the tension in the filament 80. Even with respect to this latter scenario, the indication afforded to the user by the spring 1220/spring 150 provides the user with an opportunity to adjust the deployment procedure to avoid injury to the recipient and/or damage to the closure device, etc.

It is noted that as the tensioner assembly 100 is pulled away from the recipient, and by the time that the spring 1220 has bottomed out, the pulley arrangement of the filament 80 connecting toggle 30 and the plug 50 causes the plug 50 to be moved into engagement with the exterior of the artery wall contiguous with the puncture. The tension in the filament 80 resulting from pulling the tensioner assembly away from the recipient causes the filament 80 to somewhat deform the plug, i.e., cause it to deform radially outward and, in some embodiments, twist. Because the spring 1220/spring 150 permits the tension on filament 80 to be controlled/ensures that sufficient tensioning and not too much tensioning is applied to the filament during deployment of the closure device 20, the user is provided with some reassurance that the proper amount of tensioning has been applied to the filament 80 to deform the plug and properly deploy the closure device 20.

It is noted that in an exemplary embodiment, plug 50 can be withdrawn from tube 120 without contacting the sheath 10 and/or at least without contacting the interior of the sheath 10. This may, in some embodiments, eliminate the possibility that the plug 30 might become stuck in the sheath 10—during the deployment procedure as it expands once leaving the tube 120.

It is noted that an exemplary embodiment includes an indicator that provides an indication to the user that the hub assembly 1140 has bottomed out within the frame 1120 (or corresponding structure). In an exemplary embodiment, the indicator corresponds to, at least conceptually and/or functionally, to the indicator taught in the '653 application, the contents of which pertaining to the indicator being incorporated herein by reference in their entirety for use in an embodiment.

Figure 19:
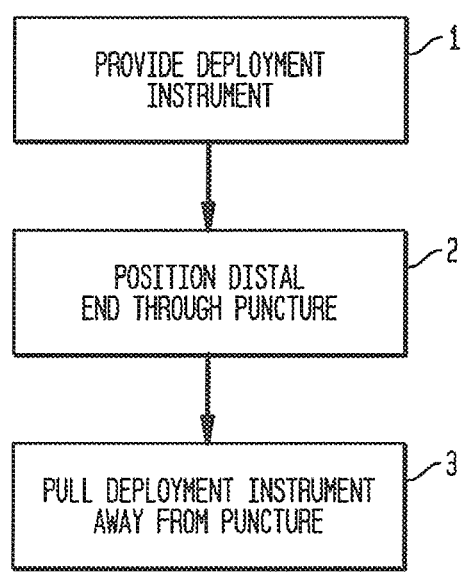
FIG. 19 is a flowchart of an exemplary method.

Accordingly, in an exemplary embodiment, referring to the flowchart of FIG. 19, there is a method of sealing a percutaneous puncture in a wall of a body passageway, comprising, at step 1, providing a deployment instrument 100 including a tensioner assembly 1110/140 and carrying a closure device 80, the closure device 80 including a toggle, a plug 50 and a contiguous elongate filament 80 configured to draw the plug 50 towards the toggle 30 upon the application of tension to the filament 80 in a direction away from the toggle 30. At step 2, the distal end of the deployment instrument 100 is positioned through the puncture into the body passageway such that the toggle 30 is located in the body passageway. At step 3 the deployment instrument 100 is pulled away from the puncture while the filament 80 is connected to the deployment instrument. This results in the application of a mechanically induced increasing tension force to the filament 80 that increases with increasing distance of the deployment instrument 100 away from the puncture, thereby drawing the toggle 30 and the plug 50 towards each other and into engagement with the wall of the body passageway at respectively opposite sides of the wall. In an exemplary embodiment, the mechanically induced increasing tension force is a result of spring, as detailed above.

FIG. 20A depicts an embodiment that utilizes two plugs 50 and 50', each located on a portion of loop 82, with a single toggle 30. An exemplary embodiment of such a configuration provides utility in that two plugs may better seal a relatively large puncture. In this regard, some punctures will extend a relatively great distance about the artery wall in a direction normal to the longitudinal axis thereof. For example, the puncture may extend over an arc that extends about 20, 25, 30, 35, 40, 45, 50, 55, 60, 65, 70, 80, 90, 100, 110, 120, 130, 140, 150, 160 170 and/or about 180 degrees or more and/or angles in between these in one degree increments. A single plug may bunch at the apex of the puncture, thus leaving portions of the large puncture exposed on either side of the plug. The use of two plugs covers more area, and thus can cover more of the puncture. By way of example, a single plug may cover a puncture extending over an arc of 10 or 20 degrees, whereas two plugs may cover a puncture extending over an arc of about 25, or 30 or 35 or 40 or more degrees. Along these lines, the use of two holes 31 for the filament spread relatively far apart can space the plugs over the full area of the puncture.

It is noted that the washer 500 detailed above can be used to spread out the filament 80 so as to avoid or otherwise reduce the tendency of the plug to bunch at the apex of the puncture in a manner the same as or similar to the manner by which the more widely spaced holes 31 prevents or otherwise reduces the bunching tendency.

FIG. 20B depicts a cross-sectional view of a closure device according to the embodiment of FIG. 20A after delivery.

As can be seen in FIG. 20A, the exemplary embodiment utilizing two plugs 50 and 50' can include two tampers 70 and 70' to tamp locks 60 and 60'. Use of these additional components may correspond to the teachings detailed above, albeit sequentially (tamping lock 60 first with tamper 70, and then tamping lock 60' with tamper 70').

Still referring to FIG. 20A, an exemplary embodiment includes an alternate embodiment of a tensioner apparatus. Specifically, FIG. 20A depicts a tensioning apparatus 400. In an exemplary embodiment, tensioning apparatus 400 corresponds to a spring that is biased such that the ends 401 and 402 of the spring are separated as shown in FIG. 20A. Specifically, ends 401 and 402 can be wrapped about filament 80 as conceptually shown, or otherwise may include devices at the ends that permits the filament 80 to slide relative therethrough while holding the filament 80. Upon tensioning the filament 80 as detailed herein, the two portions of filament 80 between element 81 and the toggle 30 will tend to move towards each other. The tensioning apparatus 400 will resist this movement owing to the spring bias just mentioned. The more tension applied to the filament 80, the greater the tendency for these portions of filament 80 to move towards each other, thus compressing the spring/moving the ends 401 and 402 closer together. Accordingly, a user can view the degree of closure of the spring/movement of ends 401 and 402 closer to one another, and thereby determine or otherwise estimate/gauge how much tension is being applied. In an exemplary embodiment, a gauge may be included with tensioning apparatus 400 that permits the user to read the tension on the filament 80 owing to the location of the ends 401 and 402 (or the arms that support the ends) relative to the gauge. In yet an alternate embodiment, a spacer element may be present between the ends (or arms) that functionally permits the spring to bottom out in a manner akin to that detailed above with respect to spring 1120/150, and thus having the functionality/utilitarian value of that configuration.

FIG. 21 depicts a variation of the embodiment of FIG. 20A, where instead of two separate tampers, a single tamper 75 is present that includes two lumens through which the two sides of the filament that forms loop 82 extends the same embodiment with a double lumen tamper used to include the double sutures.

Figure 22:
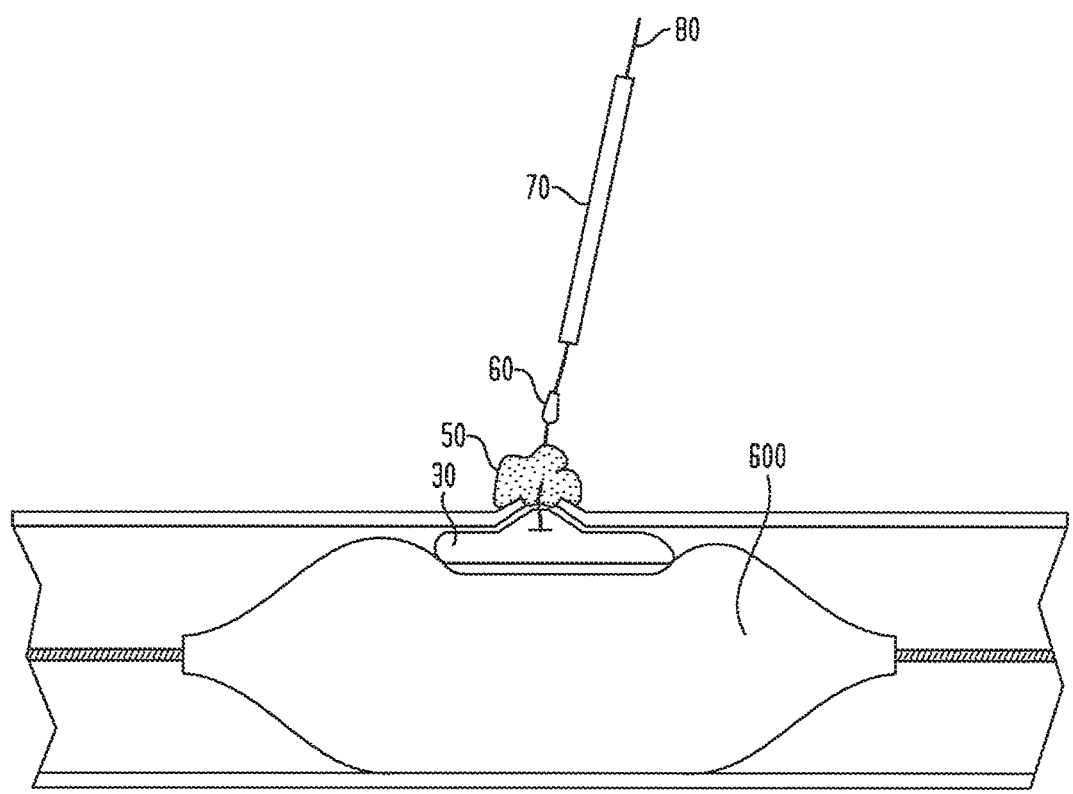
FIG. 22-23 depict use of an occlusion balloon to hold a toggle against an artery wall.

In another embodiment, the occlusion balloon 600 is moved distally from the occlusive position to the puncture site, whereby the occlusive balloon 600 is utilized to assist with positioning the toggle 30 and/or the plug 50 and sealing the puncture. Such is depicted by way of example and not by way of limitation in FIG. 22. Exemplary actions associated with such a procedure can include first position toggle intra-arterially as detailed herein and/or variations thereof in general, and, in particular, with respect to FIG. 6. Once the toggle 30 is positioned proximate the puncture, the occlusion balloon is deflated. Next, the occlusion balloon 600 is moved from its occlusion position to a location corresponding to a longitudinally proximate position of the puncture. After this, the occlusion balloon 600 is re-inflated to occluding pressure and/or another pressure that will enable the teachings detailed herein and/or variations thereof to be practiced. This can push the toggle 30 against the interior of the artery as shown in FIG. 22. The user can then double check the final position of the toggle 30 (using fluoroscopy or the like) and/or make adjustments to the tension or positioning of the plug 50 before deflating the balloon 600. (Before deflating the balloon, the closure device 20 may be secured in place according to the teachings detailed herein and/or variations thereof, or such may be done after deflating the balloon.) FIG. 22 depicts an action of this method, where it can be seen how the balloon 600 covers the toggle 30 and puncture site. This action associated with FIG. 22 can allow for full compaction of the plug 50 without any risk of or otherwise significantly statistically reducing the chances of reinsertion of the plug within the artery as compared to that which would exist without use of the balloon 600.

Figure 23:
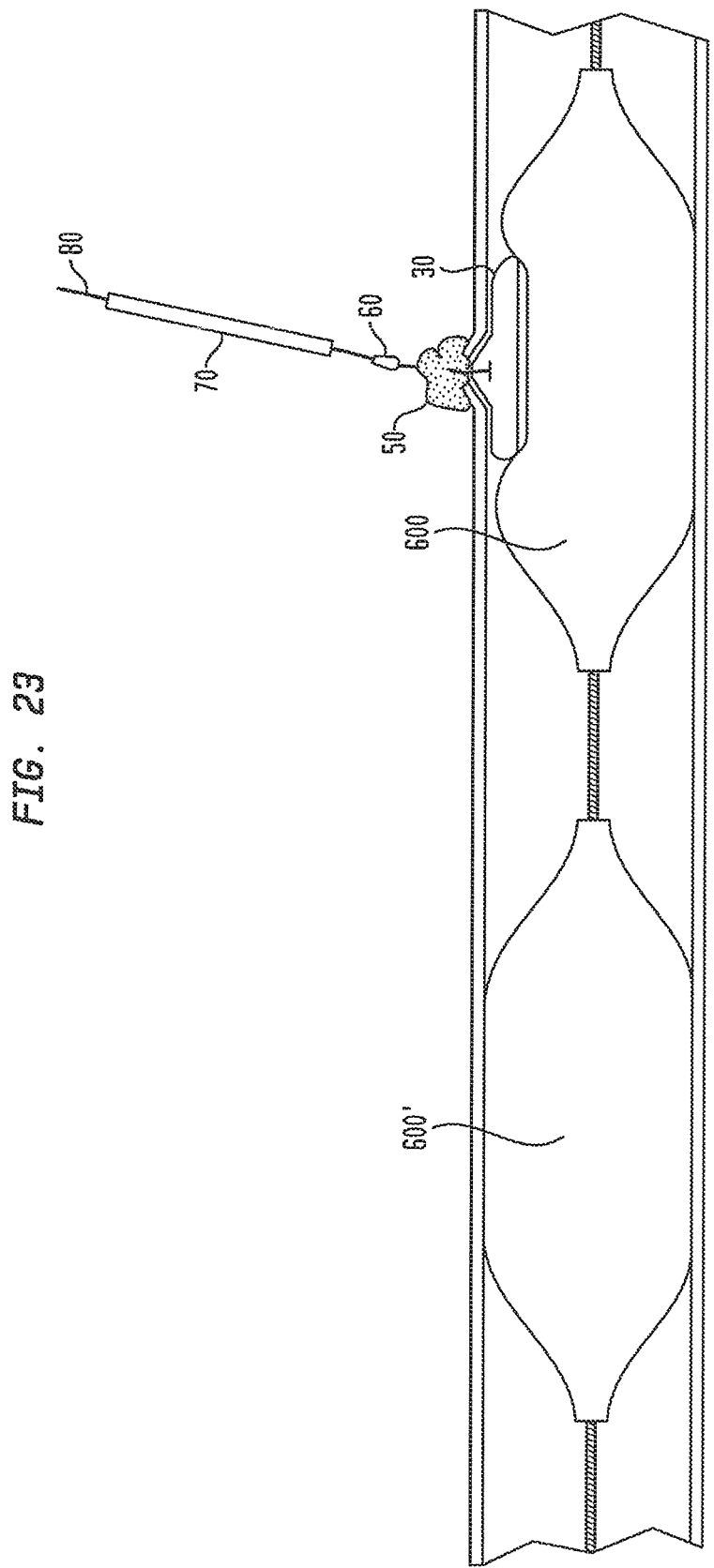

An exemplary embodiment includes the use of a double balloon catheter, where the proximal balloon serves to occlude flow, while the second, and moveable (slideable) balloon is utilized to assist with toggle and collagen placement as above. FIG. 23 depicts an action associated with a method of such an embodiment, where balloon 600' is the occluding balloon and balloon 600 is the balloon that is used to position the toggle 30.

FIGS. 24A, 24B and 24C depict an alternate embodiment of a toggle. Specifically, these FIGS. depict a toggle 135 having hinged wings or flaps 136 and 137 via hinge features 136A and 137A. Hinge features may be barrel hinges or may be areas of relative weakness that enables the wings to hingedly move (or flap). Toggle 135 has a width W1 that is larger than the maximum internal diameter of the sheath 10 on a plane normal to the longitudinal axis thereof. In this regard, wings 136 and 137 of the toggle 135 (e.g., portions outboard of the dashed lines seen in FIGS. 24A-24C), are located outboard of the inboard portion of the toggle represented by main body 138. In an exemplary embodiment, the outboard portions are flexibly connected or otherwise hingedly connected to the rest of the toggle 135.

In an exemplary embodiment, the toggle 135 is configured to elastically deform at the areas of the hinges and/or thereabouts. By way of example, width W1 of FIG. 24A is a first value, corresponding to any of the values detailed above with respect to the tip to tip distance and/or variations thereof, and this value corresponds to the value when the toggle 135 is in the relaxed state. Upon the application of a force to the wings, the value of W1 increases, by about 4 mm (about 2 mm for each wing), although in alternate embodiments, the value W1 increases by about 0.5 mm, 0.75, 1, 1.25, 1.5, 1.75, 2, 2.25, 2.5, 2.75, 3, 3.25, 3.5, 3.75, 4, 4.25, 2.4, 4.75, 5, 5.25, 5.5, 5.75, 6, 6.25, 6.5, 6.75 and/or any value in between these values and/or any ranges encompassing some or all of these values (including ranges being bounded by the in between values).

This increase in value of W1, or at least a portion thereof, elastically deforms the toggle 135, such that it retains the new value of W1 or something close to that or something in between, depending on the elastic properties that come into play associated with the plastic properties.

Figure 24D:
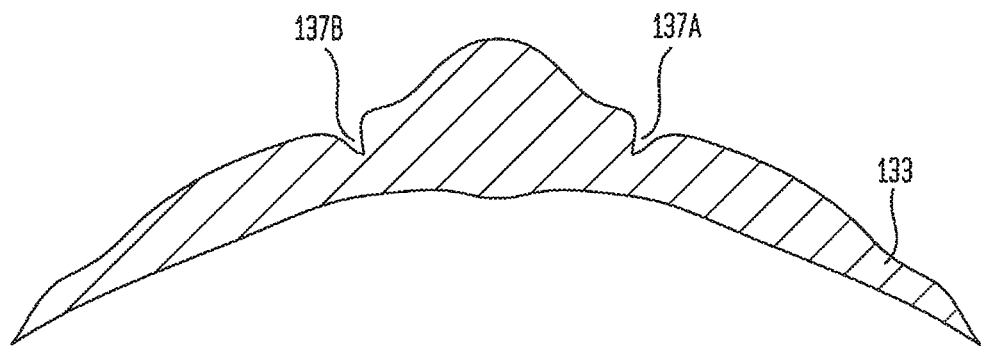

FIG. 24D depicts a cross-sectional view of toggle 135 through section A-A of FIG. 24C. As can be seen, hinge features 136A and 137A are notched sections in the top surface of the toggle 135. In an alternate embodiment, the notches are located in the bottom surface. In an alternative embodiment, the notches are located both above and below. In an exemplary embodiment, hinge feature 136A is a notch located on the top and hinge feature 137A is a notch located on the bottom, or visa-versa. (The holes 31 are not depicted in the cross-sectional view of FIG. 24D.)

Any device, system and/or method that enables the folding functions detailed herein and/or variations thereof with respect to the wings may be utilized in some embodiments.

In an exemplary embodiment, the toggle 135 is such that the resistance to flexture of the toggle along lines 136A and/or 137A is substantially and/or effectively less than resistance to flexture of the toggle at locations generally proximately inboard and outboard thereof. In an exemplary embodiment, the toggle 135 is such that the elastic modulus of the toggle along lines 136A and/or 137A is substantially and/or effectively less than that of the toggle at locations generally proximately inboard and outboard thereof.

As noted above, the wings may expand upon the application of sufficient force thereto. In this regard, an exemplary embodiment of the toggle 135 is utilized in conjunction with a balloon 600 in a manner similar to and/or the same as that detailed above with respect to FIG. 22. More particularly, FIGS. 25A, 25B and 25C schematically illustrate a sequence according to an exemplary embodiment combining the above teachings. FIG. 25A depicts the toggle 135 positioned at the puncture, with the wings 136 and 137 drooping downward prior to applying tension to the filament beyond about that which is used to hold the toggle 135 against the puncture (e.g., prior to cinching the loop 80, etc.) Balloon 600 is depicted in a deflated or semi-deflated state, and is located longitudinally proximally to the puncture (and toggle 135).

FIG. 25B depicts inflation of the balloon 600. As the balloon expands outward, wings 136 and 137 are forced outward towards the wall of the artery 1026. FIG. 25C depicts the balloon 600 inflated to at least about its maximum inflation dimensions. As can be seen, the wings 136 and 137 are trapped against the wall of the artery between the wall and the balloon 600. At this time, additional tension is applied to the filament 80 to move the plug 50 (not shown) towards the toggle 135, etc. More particularly, FIG. 25C depicts how balloon 600 (single or double embodiment) may be used to orient the wings 136 and 137 of the toggle 135 to assist with internal closure.

Exemplary embodiments of FIGS. 24A-D and/or 25A-C can be used to substantially and/or effectively statistically reduce the chances of the toggle 135 dislodging and/or passing through the puncture and into the tract relative to the other embodiments detailed herein and/or variations thereof. This statistical phenomenon may be—for example, because the additional area of the toggle 135 owing to the wings because the wings can be folded for insertion into the sheath 10. This as compared to a toggle without folding wings, where the maximum size of the toggle is limited by the internal diameter of the sheath 10.

Exemplary embodiments of FIGS. 24A-D and/or 25A-C can be used in applications where the puncture extends over a larger arcuate distance as compared to toggles having smaller widths. For example, the puncture may extend over an arc that extends about 20, 25, 30, 35, 40, 45, 50, 55, 60, 65, 70, 80, 90, 100, 110, 120, 130, 140, 150, 160 170 and/or about 180 degrees or more and/or angles in between these in one degree increments. The embodiments of FIGS. 24A-C and/or 25A-C can substantially and/or effectively statistically reduce the chances of the toggle 135 dislodging and/or passing through such punctures puncture and into the tract relative to the other embodiments detailed herein and/or variations thereof.

Figure 26A:
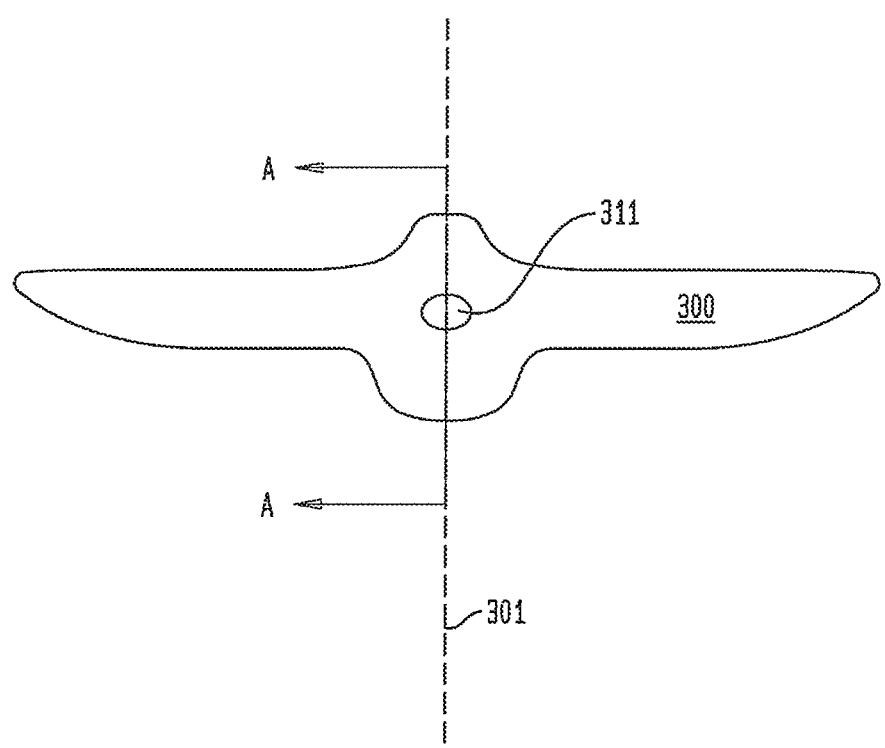
FIGS. 26A-26B depict an alternate embodiment of a toggle.
Figure 26B:
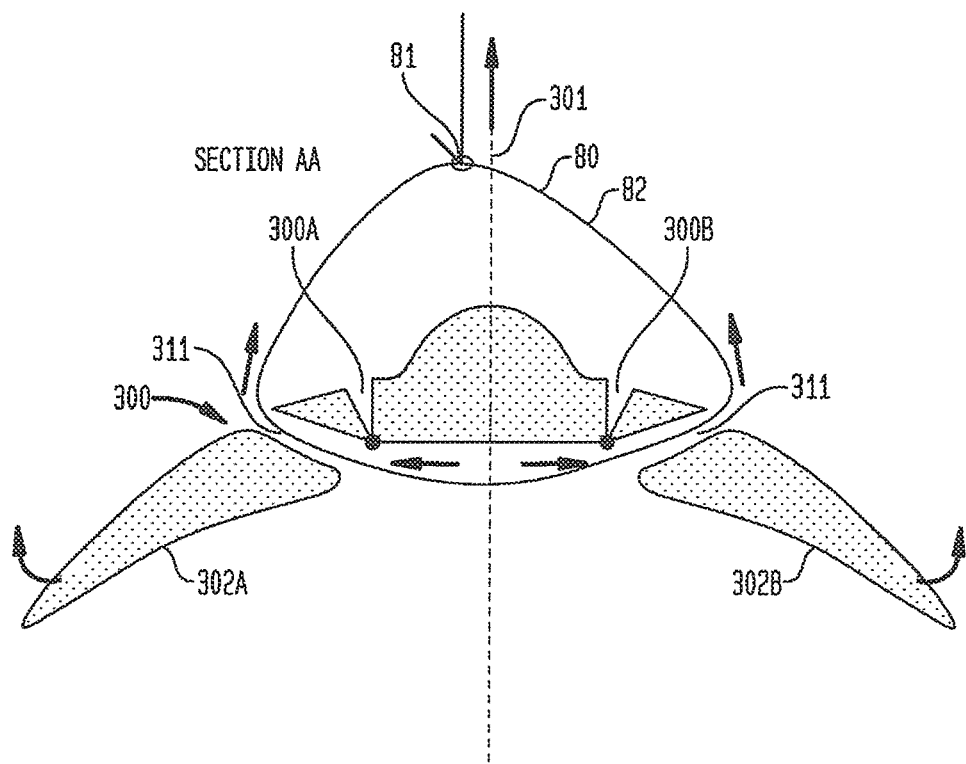

FIGS. 26A and 26B depict another embodiment, where the filament is utilized to apply the above-mentioned force to the wings to expand the wings. In this regard, FIG. 26B is a cross-sectional view of section AA of the toggle 300 depicted in FIG. 26A. In this embodiment, the holes 311 of the toggle 300 for the filament 80 are angled relative to the lateral axis 301 or positioned so as to aid in the support of the widened portion, or 'wings'. In an exemplary embodiment, this can aid in opening the toggle 300, which has hinge sections 300A and 300B extending along the midline. In an exemplary embodiment, loop 82 extends through holes 311 as may be seen. The angle of the holes relative to axis 301 has utility in that as the loop 82 is closed due to the tensioning of filament 80, the filament 80 applies a force onto wings 302A and 302B, lifting the wings upward and against the artery. It is noted that such utility can also be achieved without the angling of the holes 311 relative to axis 301. In this regard, because the holes 311 are outboard of the hinge sections 300A and 300B, the force resulting from the tensioning of the filament 80 is applied to the wings, thus forcing the wings upward and against the artery.

In addition to radiopaque marking schemes mentioned above, some embodiments detailed herein and/or variations thereof may include additional markers to ensure or otherwise substantially and/or effectively statistically improve the chances of utilitarianly deploying the toggles. Radiopaque markings on the tubes can aid in enabling the user to estimate the amount of delivery tube and/or release tube that has been pushed into the vessel. This can help the user avoid unutilitarian advancement of the toggle into the vessel (e.g., too much advancement), thereby obviating any adverse situations during deployment such as catching of the toggle on the inner wall downstream. The delivery tube and/or the release tube may have radiopaque strips or rings at fixed distances. It may also have rings with increasing thicknesses. The gradient may be designed in proportion to a qualitative assessment of distance advanced. The tube(s) may also have dots in place of rings to differentiate between the radiopaque sheath tip and the delivery tube.

Figure 27A:
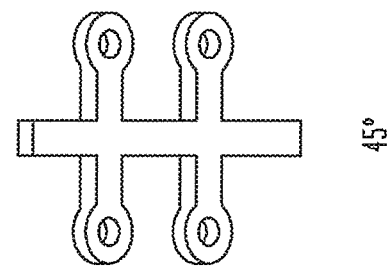
FIGS. 27A-27D depict an exemplary embodiment of a marker.
Figure 27B:
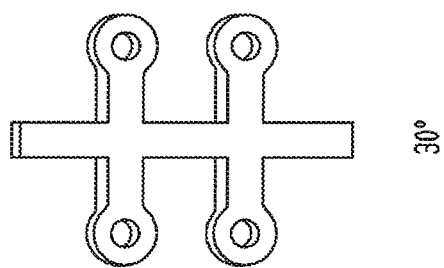
Figure 27C:
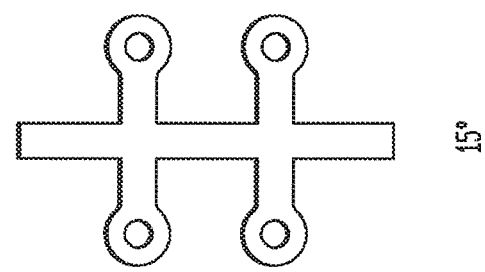
Figure 27D:
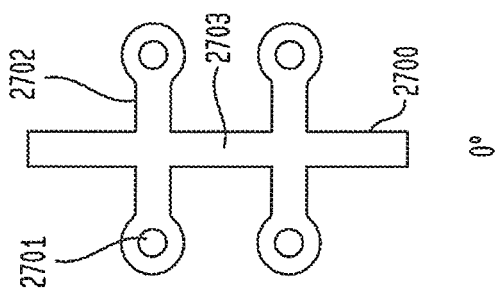

In a similar vein, an exemplary embodiment includes a toggle or other degradable intraluminal sealing member that includes a radiopaque marker. In an exemplary embodiment, one or more or all of the embodiments of toggles detailed herein and/or variations thereof may include therein a relatively thin stainless steel radiopaque marker (thickness of 0.005"-0.010"). In some exemplary embodiments, the marker may have hollow features. FIGS. 27A-D depict such an exemplary embodiment of a marker 2700, having hollow holes 2701 in arms 2702 extending from a core 2703. Embedded in or otherwise attached to a toggle, the hollow features can be utilized to indicate toggle orientation during deployment. By way of example, depending on the orientation of the toggle relative to a viewing perspective, the holes will appear anywhere from circular to highly elliptical. More particularly, under fluoroscopic guidance, the holes appear circular at 0° relative to the viewing perspective (FIG. 27A), elliptical at 15° relative to the viewing perspective (FIG. 27B), more elliptical at 30° relative to the viewing perspective (FIG. 27C) and highly-elliptical and/or closed off completely (i.e., one cannot see through the hole as the wall of the hole blocks the view) at 45° (FIG. 27D). Accordingly, there is a method of fluoroscopically confirming the orientation of the toggle relative to a viewing perspective based on how the holes look relative to a viewing perspective prior to initiating any of the actions detailed herein and/or variations thereof associated with deployment of the toggle.

More particularly, in an exemplary embodiment, during deployment of the toggle, the holes may appear closed (or highly elliptical) as the toggle is released from the delivery instrument and hangs in the intraluminal space. As the toggle is brought closer to the vessel wall as detailed herein, the varying degrees of circularity of the holes relative to a viewing perspective via fluoroscopy can provide the user with a visual confirmation of accurate positioning and/or utilitarian positioning of the toggle.

In an exemplary embodiment, the marker can also be used as a reinforcing element that reinforces the toggle and improves resistance to the tensioning of the filament as detailed above. This can have utilitarian value in that it can substantially and/or effectively statistically increase the likelihood that the toggle stays in contact with the inner wall of the vessel throughout the period of resorption. This as compared to that which would be the case in a similarly situated toggle without the marker. In an exemplary embodiment, the "marker" need never be used as a marker, but instead simply only as a reinforcing device.

Figure 29:
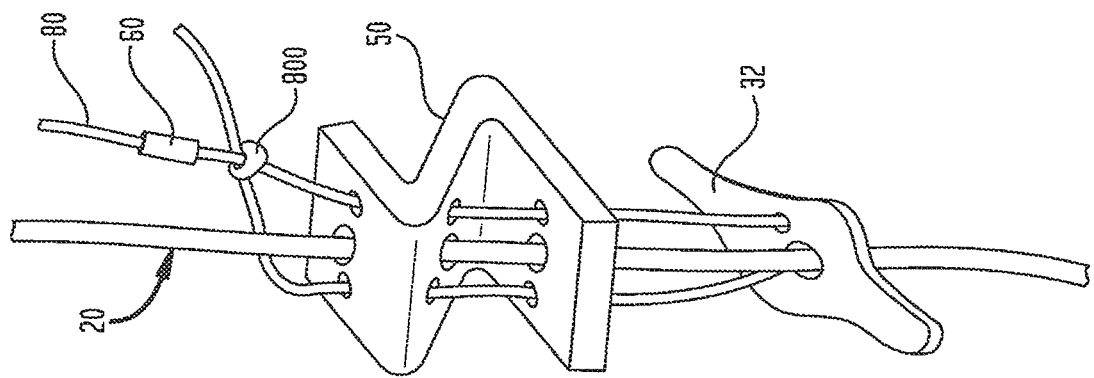
FIGS. 28-30 depict exemplary embodiments of guide wire-plug association.
Figure 28:
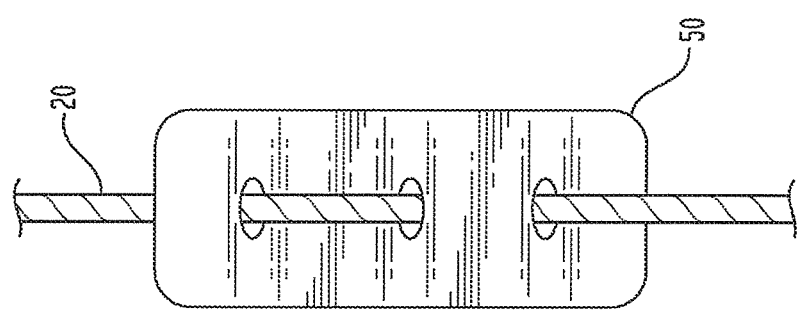
Figure 30:
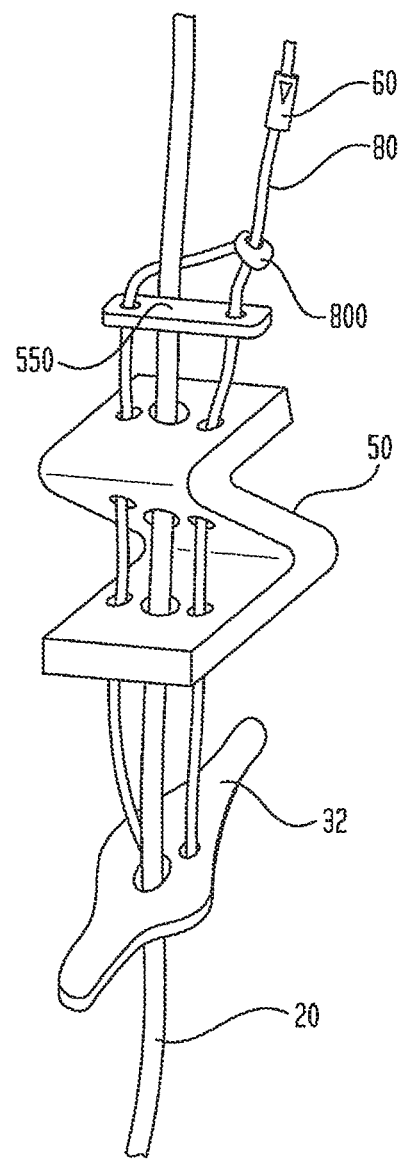

As noted above, an exemplary embodiment includes a guide wire 20 that passes through holes in the plug 50. FIGS. 28, 29 and 30 depict exemplary embodiments, of such a configuration. In a further embodiment, there is an extra luminal sealing component 550, as depicted in FIG. 30, that is in the form of a stainless steel (or any of a variety of implantable or absorbable materials) plate or bar about 0.5" long or less and about 0.010" thick or less placed between the hemostatic pad 50 and the lock 60. The plate 550 can have utilitarian value in that it can increase or otherwise result in utilitarian distribution of compression forces on the plug 50 more evenly in order to achieve statistically and/or effective reliable hemostasis.

Figure 31:
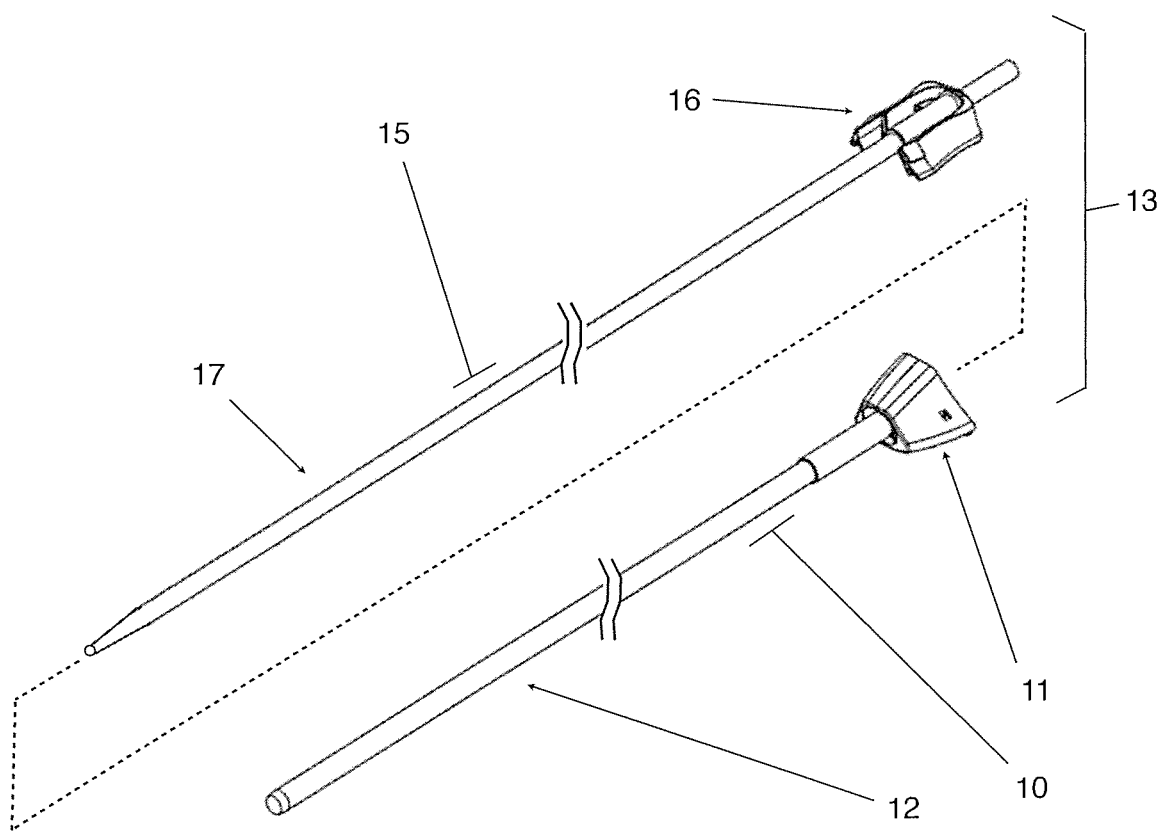
FIG. 31 depicts an exemplary embodiment of an exchange sheath system comprising an accessory sheath and introducer.

FIG. 31 depicts the exchange system 13 intended to improve the delivery of the large bore closure device described herein; namely an accessory introducer 15 and an accessory sheath 10. The accessory introducer 15 and accessory sheath 10 may be assembled together as shown, where the accessory introducer shaft 17 fits inside accessory sheath shaft 12 and accessory introducer hub 15 engages or snaps to accessory sheath hub 11 to keep the two components locked together. Squeezing accessory introducer hub 16 allows for removal of the accessory introducer 15 from accessory sheath 10 as needed. The placement of the exchange system 13 is accomplished following a method termed 'sheath exchange,' whereby a procedure sheath that is in place in the vessel during the interventional procedure is removed from the patient and a new, different sheath is inserted over the procedural guidewire. As is typical on any sheath insertion, an introducer or dilator is required within the sheath to permit easy sheath insertion into the vessel over the procedure wire. Thus, once the interventional procedure is completed, the procedure wire is held in place, and the procedural sheath is removed from the vessel and the slid proximally off the procedure wire. Manual compression is applied to the vessel puncture site to control bleeding while the assembled exchange system 13 is advanced over the procedural guidewire into the existing vessel puncture. Once the exchange system 13 is in place within the vessel, the accessory introducer 15 and procedural guidewire are removed from the accessory sheath 10. The accessory sheath 10 remains in place within the vessel, and as will be described below, is used to facilitate proper placement of the closure device delivery system within the patient.

The accessory sheath 10 also contains a sheath hub 11 that houses a hemostasis valve (not shown). This valve is common in vascular sheaths and is required to avoid blood loss while providing the ability to insert devices and guidewires into sheaths with minimal blood loss. In the case of the accessory sheath 10, the hemostasis valve within the hub is intended to prohibit blood loss from the accessory sheath until and during the time the closure device delivery system can be inserted.

Figure 32:
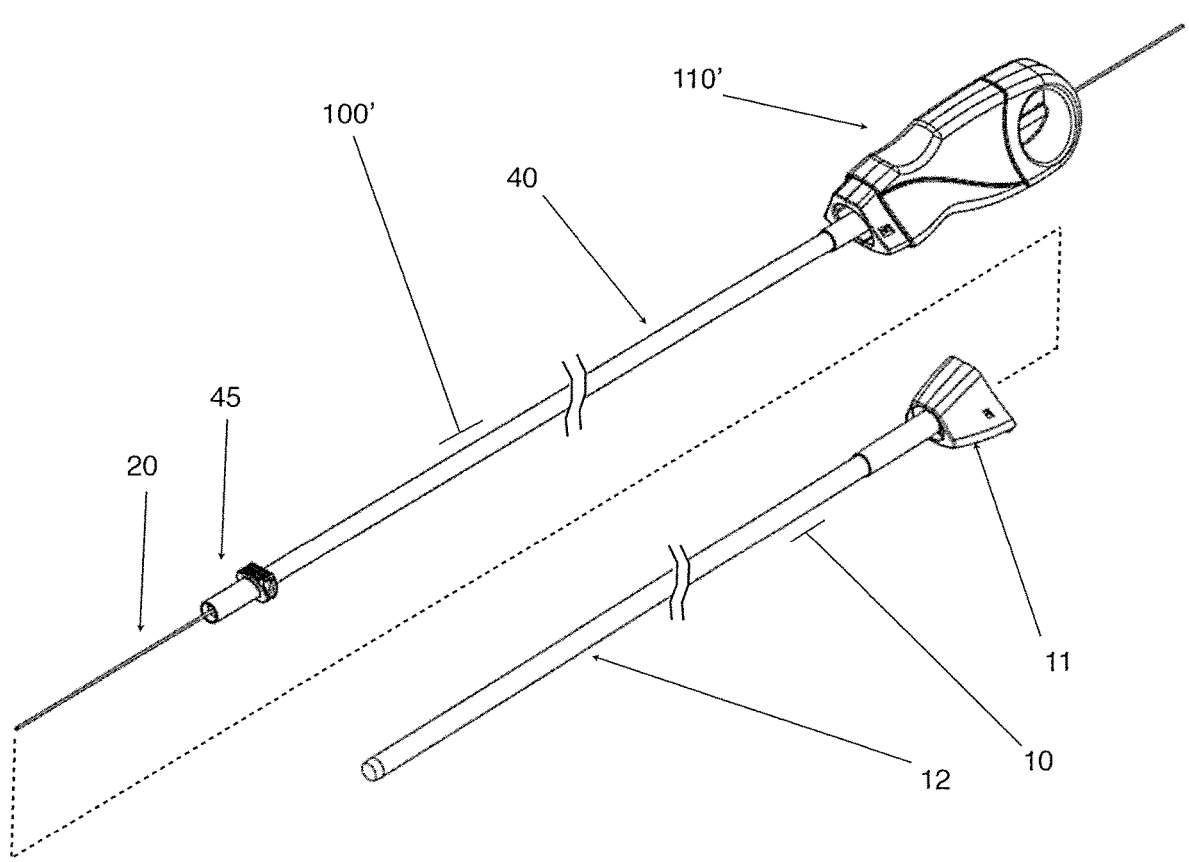
FIG. 32 depicts an exemplary embodiment of the delivery system and the associated accessory sheath.

FIG. 32 depicts an embodiment of the closure device delivery system 100' containing the closure device (not shown) and a guidewire 20, which is also inside the closure device delivery system 100'. As has been previously described previously herein, guidewire 20 is similar in form and function to procedural guidewires, but in combination with the closure delivery system, serves to facilitate placement of the closure device elements around the vessel puncture during deployment of the closure device. To begin the deployment procedure, the guidewire 20 of the closure device delivery system 100' is inserted into and past the hemostasis valve in the sheath hub 11, until the bypass tube 45 of the delivery system 100' enters the accessory sheath hub 11, and is pushed inside the hub to open the hemostasis valve. The delivery system shaft 40 is then slid inside the stationary bypass tube 45, past the opened hemostasis valve, until the delivery system handle 110' abuts the sheath hub 11. On full insertion, the delivery system handle 110' locks to the accessory sheath hub 11, indicating to the user that the delivery system 100' is positioned correctly within the accessory sheath 10. Delivery system shaft 40 is designed to be longer than accessory sheath shaft 12, thus the delivery system shaft 40 extends distally into the vessel beyond the tip of the accessory sheath shaft 12. This is necessary to permit release and deployment of the closure elements in subsequent steps deployment steps previously describe herein.

Figure 33:
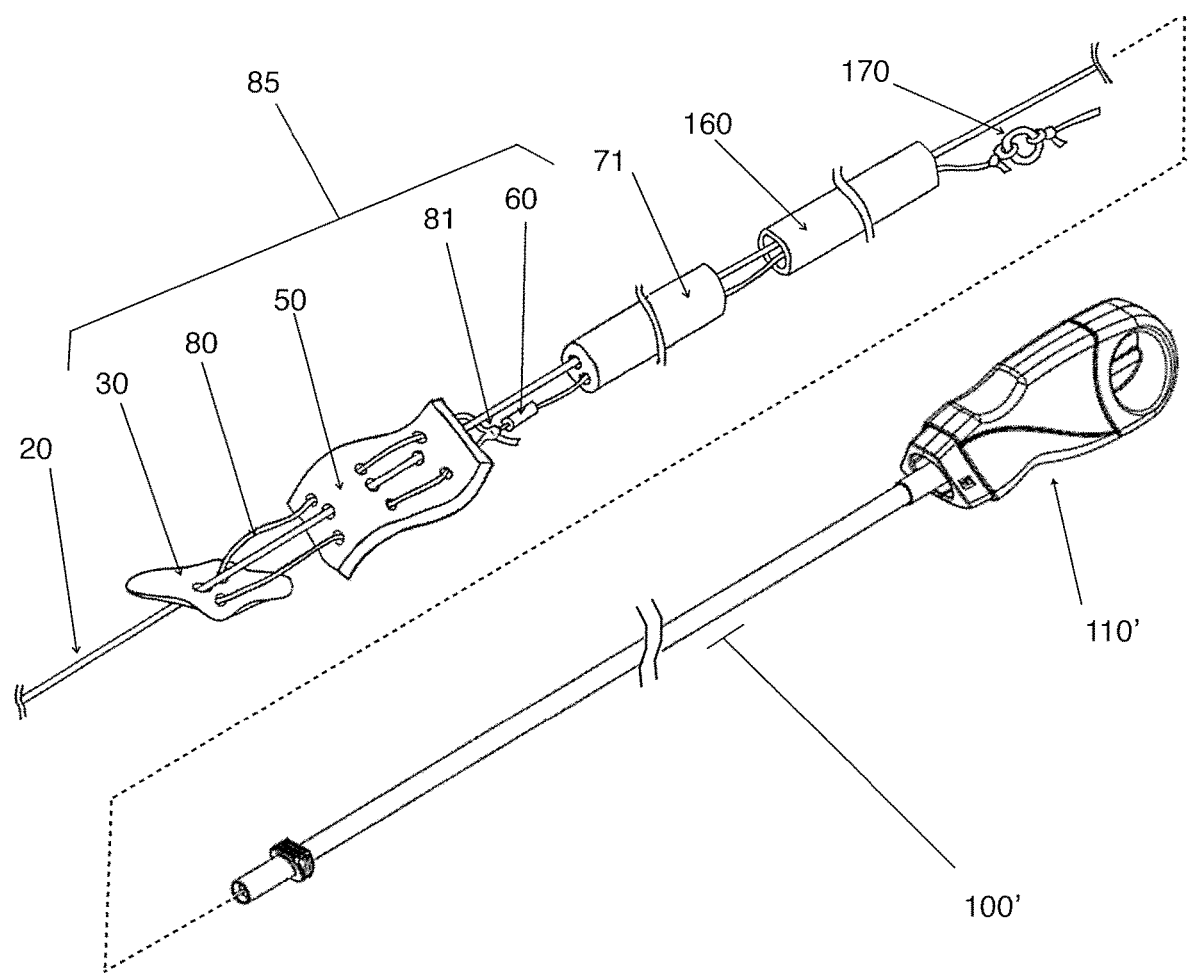
FIG. 33 depicts an exemplary embodiment of the closure device centered on a guidewire and its associated delivery system.

The contents of the closure device delivery system 100' in a preferred embodiment are shown in FIG. 33, and include the guidewire 20, the toggle 30, the collagen pad 50, a slideable knot 81, a lock 60, the tamper tube 71, the connecting suture 80, the tensioning cartridge 160, and a tensioning o-ring 170. These components are housed within the delivery system and have been described previously. Of particular importance is the inclusion of the guidewire 20 within the closure device delivery system 100', central to all components, such that the user of the delivery system is not required to 'thread' the guidewire through the various internal components, but rather it is assembled beforehand. In this manner the closure device delivery system 100' is assembled as shown, containing the guidewire 20. During use the guidewire 20 and closure device delivery system are inserted together in a fixed-wire fashion into the accessory sheath 10, whereby the guidewire 20 is advanced by the action of advancing the closure device delivery system 100'.

Figure 34:
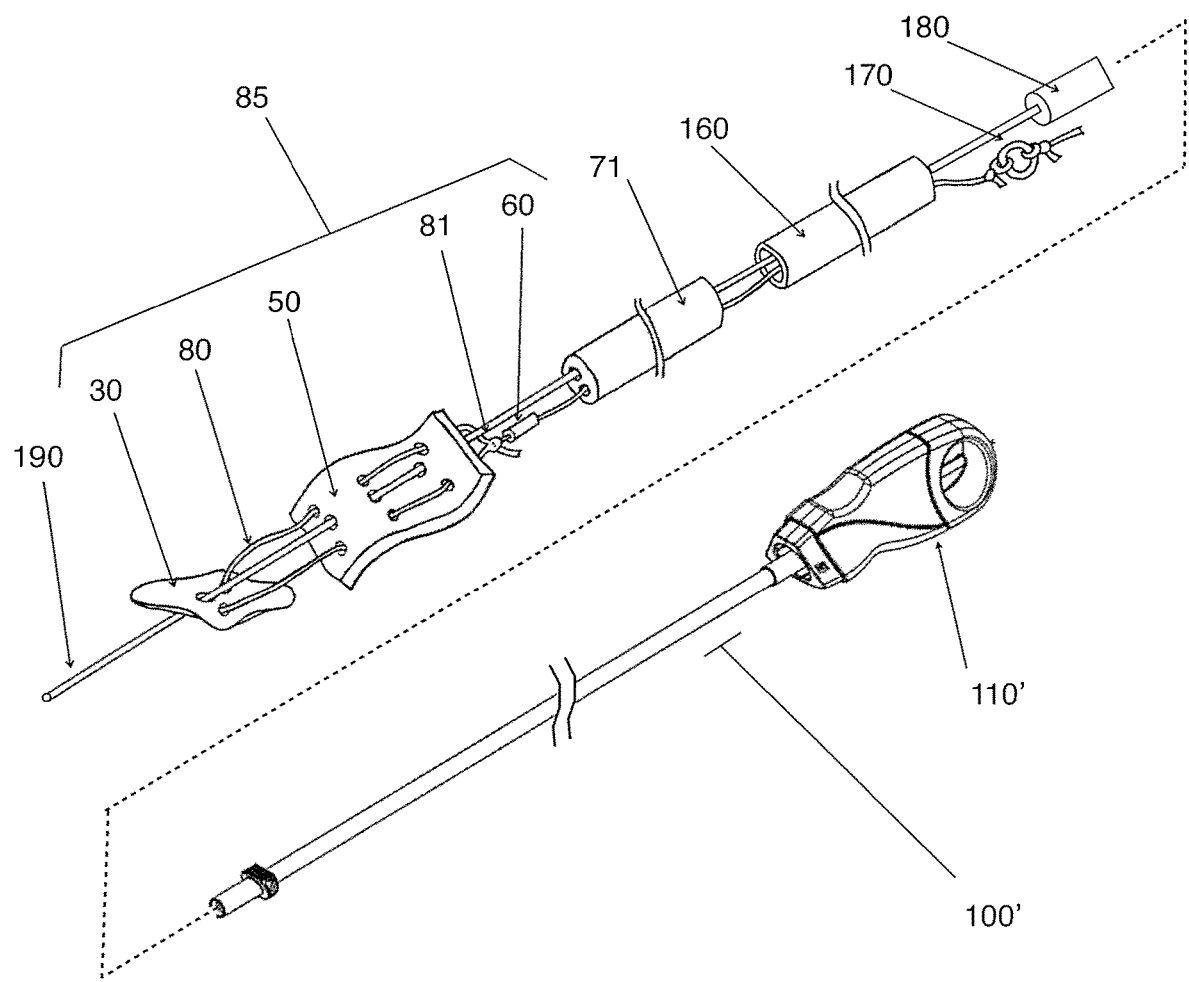
FIG. 34 depicts an exemplary embodiment of the closure device centered on a guidewire lumen and its associated delivery system.

In a previous description, the tensioning o-ring 170 was described to encircle the tensioning cartridge and provide drag against the internal surface of the delivery system shaft 40. As shown in FIGS. 33 and 34, the o-ring 170 alternatively can be tethered to the cartridge and pulled along behind the cartridge during deployment, achieving similar drag when the outside diameter of o-ring 170 is larger than the inside diameter of delivery system shaft 40. This arrangement provides an excellent system for deployment tension or drag, as the o-ring elongates under tension during deployment, which acts to regulate the drag forces, making this design arrangement less dependent upon tight dimensional specifications.

In some instances it would also be preferable to advance the closure device system over the procedural guidewire, rather than utilizing guidewire 20 as part of the assembly. An alternate embodiment is shown in FIG. 34 that utilizes a tube 190 that defines a guidewire lumen and includes a hub 180 as a substitute for guidewire 20 during the manufacturing assembly process. In this embodiment, a closure device system 100' can include a toggle 30 configured to engage an interior surface of the vessel wall, a plug or collagen pad 50 configured to engage an exterior surface of the vessel wall, and a suture 80 that extends through the plug 50 and through the toggle 70 along at least a first direction so as to couple the toggle 70 to the plug 50 such that the plug 50 is proximal to the toggle 70. The tube 190 extends or otherwise passes through some or all of the closure device elements. As shown, the tube 190 extends through the plug 50 and through the toggle 70 along the first direction such that a distal end of the tube 190 is disposed distally to the toggle 70. The guidewire lumen of the tube 190 extends therethrough along the first direction and is configured to receive a guidewire such that the plug 50, toggle 70, and tube 190 are slidable along the guidewire toward the vessel wall.

To facilitate guidewire insertion into the guidewire lumen of the tube 190, the tube 190 extends beyond the toggle 30 so that the user can access the distal end of the tube 190 without difficulty. The extension of the tube 190 can be approximately 1 cm or as long as 2-3 cm, or longer from the toggle 70.

With continued reference to FIG. 34, the system 100' can further include a tamper 71 that is proximal to the plug 50 and a lock 60 coupled to the suture 80 between the plug 50 and tamper 71. The tamper 71 is configured to contact and move the lock 60 against the plug 50 to thereby compress the plug against the vessel wall such that the compressed plug 50 is held against the vessel wall by the toggle 70 and the lock 60.

The tamper 71 defines a suture lumen that extends therethrough along the first direction and tamper guidewire lumen that extends therethrough along the first direction. As shown in FIG. 34, the tube 190 extends through the tamper guidewire lumen and the suture 80 extends through the suture lumen such that the plug 50, toggle 70, tube 190, and tamper 71 are slidable along the guidewire toward the vessel wall. In particular, the suture 80 extends from the suture lumen of the tamper 71, through the plug 50 and through the toggle 70 along the first direction so as to define a first portion of suture. The suture 80 then loops back through the toggle 70 and through the plug 50 along a second direction that is opposite the first direction so as to define a second portion of suture 80. The second portion of suture terminates in a knot 81 between the lock 60 and the plug 50 such that the suture 80 forms a loop that begins and ends at the knot 81. The tube 190 preferably extends through the plug 50 between the first and second portions of the suture 80. It should be appreciated, however, that the tube 190 can extend through other portions of the plug 50 relative to the suture 80, as desired.

As shown in FIG. 34, the hub 180 is attached within the deployment device handle 110', and the tube 190 passes through a delivery tube 40 of the deployment device. The delivery tube is configured to hold the closure device including the plug 50, toggle 70, and tamper 71 when the closure device is in a pre-deployment state. Also within the delivery tube 40 is a tensioning cartridge 160 that receives the suture 80 such that when the deployment device is pulled proximally the tensioning cartridge 160 increases the tension in the suture and subsequently provides a feedback indicating that the suture is fully tensioned. The tube 190 extends through the tube 40, through the cartridge 160, and also through the portions of the closure device while the device is in the pre-deployment state. Thus, a tube is contained within some or all the closure device elements and subsequently permits insertion of a guidewire and easy advancement of the closure device delivery system 100' over a procedural guidewire rather than over the guidewire 20 as shown in FIG. 33.

In operation a guidewire is inserted into the body passageway such that the guidewire extends from outside the body passageway, through the puncture, and into the body passageway. The guidewire is then inserted into the guidewire lumen of the tube 190 and the closure system 100' is moved along the guidewire such that the toggle 70 enters the body passageway through the puncture. The delivery device is then pulled proximally to thereby deploy the plug 50 and tamper 71. Further pulling will also pull the tube 190 proximally so as to remove the tube 190 from the closure device (e.g. the toggle 70, the plug 50, and the tamper 71).

Embodiments disclosed herein and variations thereof include various interventional cardiology procedures which utilize large access sheaths to accommodate large devices. Non-exhaustive examples may include methods that include steps of balloon aortic valvuloplasty (BAV) and percutaneous aortic valve replacement (PAVR), both of which are utilized with sheaths ranging from 12-24 F. Closure of access sites involving sheaths this large are accomplished with the closure devices and deployment instruments disclosed herein and variations thereof, as well as methods for closing such access sites disclosed herein (which includes those disclosed in the above referenced applications, scaled for such closure) instead of and/or in addition to surgical closure procedures and/or the use of multiple traditional vascular closure devices. In an exemplary embodiment, the devices and methods disclosed herein and variations thereof reduce by 50%, 75%, 90%, 95%, and/or 99% or more the failure rates associated with closure of access sites of the just-mentioned procedures (i) such as those disclosed by, for example, Herrmann et al, discusses the successful use of multiple 8 F Angio-Seal devices (St Jude Medical, Minnetonka, Minn.) to close the arterial access site from BAV procedures, combating historical vascular complication rates from various studies ranging from 11-23%, (ii) and/or such as those disclosed by the Ramy et al2 report on the use three Perclose devices utilized for the closure of PAVR arterial access sites, suggesting deployment of the devices at 60 degree offsets to completely close the arteriotomy around the periphery.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with any future claims and their equivalents.

What is claimed:

1. A closure device system for sealing a percutaneous puncture in a vessel wall, the closure device system comprising:
   a toggle configured to engage an interior surface of the vessel wall, the toggle having a first end, a second end, a length that extends from the first end to the second, a lower surface, a wall engaging surface opposite the lower surface, a thickness that extends from the wall engaging surface to the lower surface, and an opening that extends from the wall engaging surface to the lower surface, wherein the thickness is perpendicular to the length;
   a plug configured to engage an exterior surface of the vessel wall;
   a suture that extends through the plug and through the toggle along at least a first direction so as to couple the toggle to the plug such that the plug is proximal to the toggle along the first direction; and
   a tube having a proximal end, a distal end opposite the proximal end along the first direction, and a guidewire lumen that extends therethrough along the first direction, the tube extending through the plug and through the opening of the toggle along the thickness such that the distal end of the tube is disposed distal to the lower surface of the toggle along the first direction, wherein the guidewire lumen is configured to receive a guidewire that protrudes from the vessel wall such that the plug, toggle, and tube are slidable along the guidewire toward the vessel wall.

2. The closure device system of claim 1, further comprising a tamper that is proximal to the plug, the tamper defining a suture lumen that extends therethrough along the first direction and a tamper guidewire lumen that extends therethrough along the first direction, wherein the tube extends through the tamper guidewire lumen and the suture extends through the suture lumen, such that the plug, toggle, tube, and tamper are slidable along the guidewire.

3. The closure device system of claim 2, wherein the suture extends (i) through the plug and through the toggle along the first direction, (ii) back through the toggle and through the plug along a second direction that is opposite the first direction, and (iii) terminates in a knot between the tamper and the plug such that the suture forms a loop that begins and ends at the knot.

4. The closure device system of claim 3, wherein (i) the portion of the suture that extends through the plug along the first direction is a first portion of suture and the portion of suture that extends through the plug along the second direction is a second portion of suture, and (ii) the tube extends through the plug and the toggle between the first and second portions of suture.

5. The closure device system of claim 4, further comprising a lock coupled to the suture proximal to the plug, wherein the tamper is configured to contact and move the lock against the plug to thereby compress the plug against the vessel wall such that the compressed plug is held against the vessel wall by the toggle and the lock.

6. The closure device system of claim 5, wherein the knot is disposed between the lock and the plug.

7. The closure device system of claim 1, wherein the tube is configured to be pulled proximally along the guidewire relative to the toggle and the plug.

8. The closure device system of claim 1, wherein (i) the toggle defines a notch at its periphery, and (ii) the tube extends through the notch.

9. The closure device system of claim 1, wherein the distal end of the tube is spaced from the toggle by a distance of at least 1 cm.

10. A closure device system for sealing a percutaneous puncture in a vessel wall, the closure device system comprising:
a closure device configured to seal the puncture, the closure device having a toggle configured to engage an interior surface of the vessel wall, a plug configured to engage an exterior surface of the vessel wall; and a suture that extends through the plug and through the toggle along at least a distal direction so as to couple the toggle to the plug such that the plug is proximal to the toggle; and
a deployment device including:
 a) a tension cartridge coupled to the suture;
 b) a delivery tube configured to hold the closure device in a pre-deployment state, the delivery tube having a rearward end and a forward end spaced from the rearward end along the distal direction, and
 c) a guidewire tube within the delivery tube, the guidewire tube having a proximal end, a distal end spaced from the proximal end along the distal direction, and a guidewire lumen that extends from the proximal end to the distal end, the guidewire tube positioned in the delivery tube and extending through the plug, the toggle, and the tensioning cartridge, along the distal direction such that the distal end of the guidewire tube extends outward from the forward end of the delivery tube in the distal direction, wherein the guidewire tube is moveable relative to the closure device as the closure device is deployed from the delivery tube, wherein the lumen is configured to receive a guidewire that protrudes from the vessel wall such that the closure device and deployment device are together slidable along the guidewire toward the vessel wall.

11. The closure device system of claim 10, further comprising a tamper that is proximal to the plug, the tamper defining a suture lumen that extends therethrough along the first direction and a tamper guidewire lumen that extends therethrough along the first direction, wherein the guidewire tube extends through the tamper guidewire lumen and the suture extends through the suture lumen, such that the plug, toggle, guidewire tube, and tamper are slidable along the guidewire.

12. The closure device system of claim 11, wherein the deployment device is configured to be pulled proximally along the guidewire relative to the closure device.

13. The closure device of claim 11, wherein when the deployment device is pulled proximally the tension cartridge increases the tension in the suture and subsequently provides a feedback indicating that the suture is tensioned.

14. The closure device system of claim 11, wherein the distal end of the guidewire tube is spaced from the toggle by a distance of at least 1 cm.

15. A closure device system for sealing a percutaneous puncture in a vessel wall, the closure device comprising:
a toggle configured to engage an interior surface of the vessel wall, the toggle having a thickness, a first opening, and a second opening separate from the first opening;
a plug configured to engage an exterior surface of the vessel wall, the plug having a first plug opening and a second plug opening separate from the first plug opening;
a suture that extends through the first plug opening of the plug and through the first opening of the toggle to couple the toggle to the plug such that the plug is disposed relative to the toggle in a proximal direction; and
a tube having a proximal end, a distal end opposite the proximal end in a distal direction that is opposite to the proximal direction, and a guidewire lumen that extends therethrough along the first direction, the tube extending through the second plug opening of the plug and through the second opening of the toggle along the first direction such that the distal end of the tube is disposed distal to the toggle along the first direction, the guidewire lumen being configured to receive a guidewire such that the plug, the toggle, and the tube are slidable along the guidewire, wherein the tube is movable relative to the toggle so that the distal end of the tube is removable from the second opening of the toggle in the proximal direction.

16. The closure device system of claim 15, further comprising a tamper that is proximal to the plug, the tamper defining a suture lumen that extends therethrough along the first direction and a tamper guidewire lumen that extends therethrough along the first direction, wherein the tube extends through the tamper guidewire lumen and the suture extends through the suture lumen, such that the plug, toggle, tube, and tamper are slidable along the guidewire.

17. The closure device system of claim 16, wherein the suture extends (i) through the plug and through the toggle along the first direction, (ii) back through the toggle and through the plug along a second direction that is opposite the first direction, and (iii) terminates in a knot between the tamper and the plug such that the suture forms a loop that begins and ends at the knot.

18. The closure device system of claim 17, wherein (i) the portion of the suture that extends through the plug along the first direction is a first portion of suture and the portion of suture that extends through the plug along the second direction is a second portion of suture, and (ii) the tube extends through the plug and the toggle between the first and second portions of suture.

* * * * *